US012577281B2

(12) United States Patent
Cohen et al.

(10) Patent No.: US 12,577,281 B2
(45) Date of Patent: Mar. 17, 2026

(54) MITOCHONDRIAL-DERIVED PEPTIDES AND ANALOGS THEREOF FOR USE AS A THERAPY FOR AGE-RELATED DISEASES INCLUDING CANCER

(71) Applicant: University of Southern California, Los Angeles, CA (US)

(72) Inventors: Pinchas Cohen, Los Angeles, CA (US); Kelvin Yen, Los Angeles, CA (US); Su-Jeong Kim, Los Angeles, CA (US)

(73) Assignee: University of Southern California, Los Angeles, CA (US)

( * ) Notice: Subject to any disclaimer, the term of this patent is extended or adjusted under 35 U.S.C. 154(b) by 725 days.

(21) Appl. No.: 17/921,577

(22) PCT Filed: May 14, 2021

(86) PCT No.: PCT/US2021/032641
§ 371 (c)(1),
(2) Date: Oct. 26, 2022

(87) PCT Pub. No.: WO2021/231988
PCT Pub. Date: Nov. 18, 2021

(65) Prior Publication Data
US 2023/0167161 A1 Jun. 1, 2023

Related U.S. Application Data

(60) Provisional application No. 63/025,495, filed on May 15, 2020.

(51) Int. Cl.
*C07K 14/47* (2006.01)
*A61P 29/00* (2006.01)

(52) U.S. Cl.
CPC .............. *C07K 14/47* (2013.01); *A61P 29/00* (2018.01)

(58) Field of Classification Search
CPC .......... C07K 14/47; A61P 29/00; A61P 35/00; A61K 38/1709
See application file for complete search history.

(56) References Cited

U.S. PATENT DOCUMENTS

| | | |
|---|---|---|
| 11,124,551 B2 | 9/2021 | Cohen et al. |
| 2017/0088852 A1 | 3/2017 | Dangoor et al. |
| 2018/0360910 A1 | 12/2018 | Cohen et al. |

FOREIGN PATENT DOCUMENTS

| | | |
|---|---|---|
| WO | 0181581 A2 | 11/2001 |
| WO | 2017223533 A1 | 12/2017 |
| WO | 2021231988 A2 | 11/2021 |

OTHER PUBLICATIONS

International Search Report and Written Opinion for PCT/US2021/032641, dated Nov. 26, 2021, 13 pages.
Kim et al., Mitochondrially derived peptides as novel regulators of metabolism, The Journal of Physiology, 2017, vol. 595(21), pp. 6613-6621.
Supplementary European Search Report for EP 21802909, dated Apr. 4, 2024, 8 pages.
Zuccato et al., Mitochondrial-derived peptide humanin as therapeutic target in cancer and degeneratie diseases, Expert Opinion on Therapeutic Targets, 2018, vol. 23(2), pp. 117-126.
Office Action for Application No. P6002399/2022 dated Mar. 12, 2025, 6 Pages.
Lee et al., The Mitochondrial-Derived Peptide MOTS-c Promotes Metabolic Homeostasis and Reduces Obesity and Insulin Resistance, Cell Metabolism, 2015, vol. 21, pp. 443-454.
Cobb et al., Naturally occurring mitochondrial-derived peptides are age-dependent regulators of apoptosis, insulin sensitivity, and inflammatory markers, Aging, 2016, vol. 8(4), pp. 796-809.
Yen et al., "Mitochondrial-derived microproteins: from discovery to function." Trends in Genetics 41.2 (2025): 132-145.
European Examination Report from the European Patent Office for Application No. 21 802 909.9-1111, mailed Dec. 11, 2024 (5 pages).

*Primary Examiner* — Elly-Gerald Stoica
(74) *Attorney, Agent, or Firm* — Nixon Peabody LLP; Linda B. Huber; Suwei Zhu

(57) ABSTRACT

Described herein is a new mitochondrial peptide. This small peptide is capable of modulating cancer, through a variety of mechanisms including autophagy/apoptosis, reduction of tumor cell viability, inducing inflammatory response in senescent cells and conversion of macrophage cell type. Administration of the peptide, its analogs and derivatives thereof, are likely to be effective treatments for cancer therapy, including generation of synthetic analogs that further enhance or abrogate activity relative to the peptide.

5 Claims, 19 Drawing Sheets

Specification includes a Sequence Listing.

Body Weight

Food Intake

Basal Metabolic Rate

Myc 1hr ratio

Fibroblast 30min ratio

MITOCHONDRIAL-DERIVED PEPTIDES AND ANALOGS THEREOF FOR USE AS A THERAPY FOR AGE-RELATED DISEASES INCLUDING CANCER

CROSS-REFERENCE TO RELATED APPLICATIONS

This application is a National Phase of International Application No. PCT/US2021/032641, filed May 14, 2021, which designated the U.S. and that International Application was published under PCT Article 21 (2) in English, which claims priority to and benefit of U.S. provisional patent application No. 63/025,495, filed May 15, 2020, the entirety of which is hereby incorporated by reference.

STATEMENT REGARDING FEDERALLY-SPONSORED RESEARCH OR DEVELOPMENT

This invention was made with government support under Grant Nos. AG034430 and GM090311 awarded by National Institutes of Health. The government has certain rights in the invention.

REFERENCE TO SEQUENCE LISTING

The Sequence Listing submitted May 14, 2021 as a text file named "SequenceListing-065715-000103WO00_ST25" created on May 14, 2021 and having a size of 82,684 bytes, is hereby incorporated by reference.

FIELD OF THE INVENTION

Described herein are methods and compositions related to mitochondrial peptides, analogs and derivatives thereof for use as a therapy for age-related diseases, including cancer.

BACKGROUND

Mitochondrial peptides represent a new class of molecules for treatment of human diseases. It is now well-established that mitochondria are key actors in generating energy and regulating cell death. Mitochondria communicate back to the cell via retrograde signals that are encoded in the nuclear genome, or are secondary products of mitochondrial metabolism. More recently, mitochondrial-derived peptides that are encoded by the mitochondrial genome have been identified as important actors in these regulatory processes. It is widely believed that mitochondrial-derived retrograde signal peptides will aid in the identification of genes and peptides with therapeutic and diagnostic to treat human diseases.

Therefore, it is an objective of the present invention to provide compositions based on mitochondrial-derived peptides for treatment of age-related diseases, including cancer.

BRIEF DESCRIPTION OF THE FIGURES

FIGS. 5A and 5B are based on MTT assay. FIG. 5C is 10 μM NOSH treatment for 24 hr in non-senescent (NS) and senescent cells. Alternative representations of FIGS. 5A and 5B are shown in FIGS. 5D and 5E, respectively.

FIG. 8A depicts viability of J82 cells, OVCAR3 cells, SHSY5Y cells, HepG2 cell. FIG. 8B depicts viability of HCT116 cells and MCF7 cells (upper row: 10 μM for 24 hours; lower row: 100 μM).

DETAILED DESCRIPTION OF THE INVENTION

Figure 1:
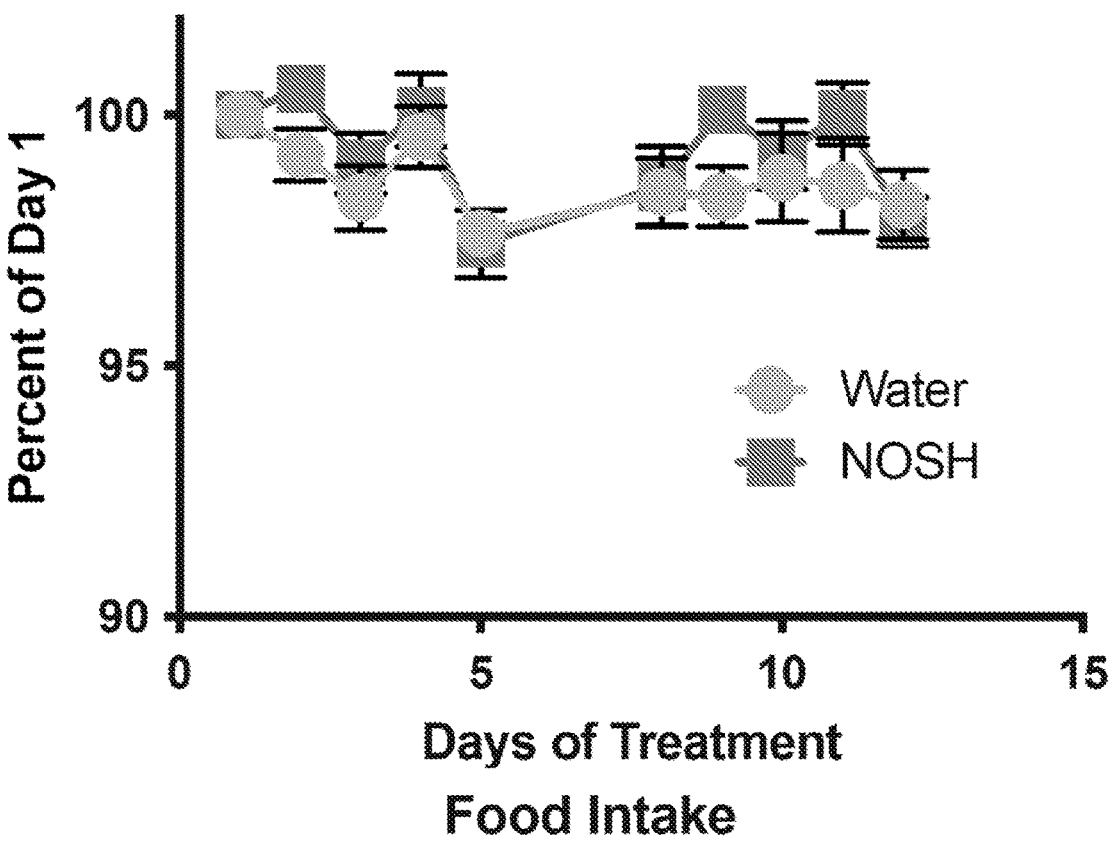
FIG. 1. NOSH (ND-One short open reading frames (sORF) in Humans) is safe in mice. NOSH has a sequence of MRLFGLLLAVRRSGRSLSLMLTLIRGLSKRLG (SEQ ID NO:215).
Figure 1:
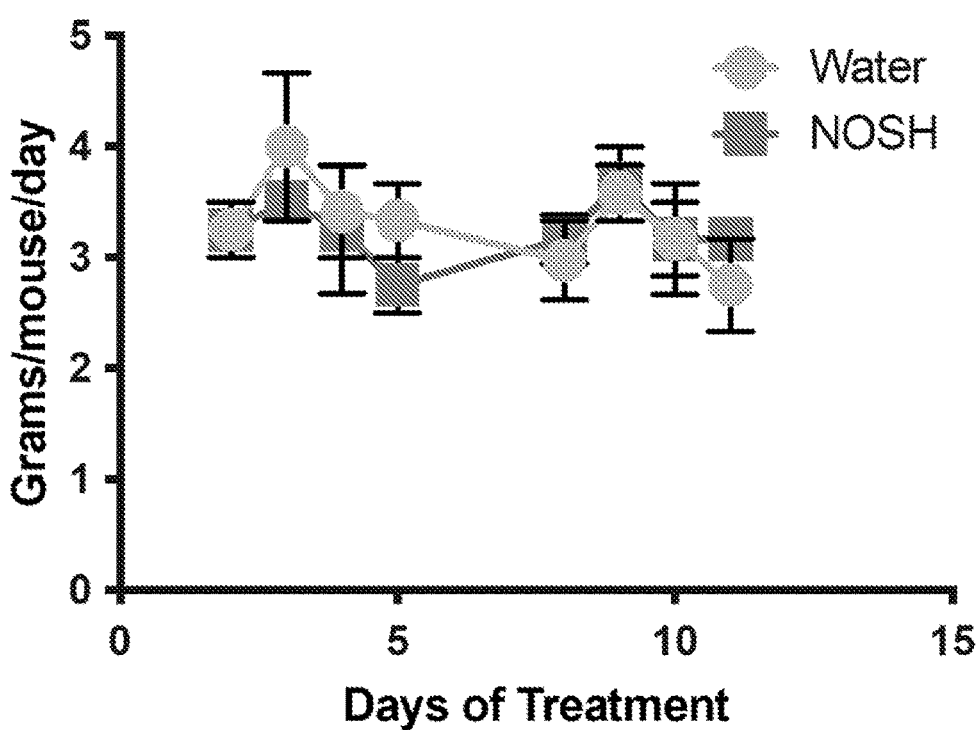

All references cited herein are incorporated by reference in their entirety as though fully set forth. Unless defined otherwise, technical and scientific terms used herein have the same meaning as commonly understood by one of ordinary skill in the art to which this invention belongs. Singleton et al., *Dictionary of Microbiology and Molecular Biology* 3$^{rd}$ ed., Revised, J. Wiley & Sons (New York, NY 2006); and Sambrook and Russel, *Molecular Cloning: A Laboratory Manual* 4$^{th}$ ed., Cold Spring Harbor Laboratory Press (Cold Spring Harbor, NY 2012), provide one skilled in the art with a general guide to many of the terms used in the present application.

One skilled in the art will recognize many methods and materials similar or equivalent to those described herein, which could be used in the practice of the present invention. Indeed, the present invention is in no way limited to the methods and materials described.

"Administering" and/or "administer" as used herein refer to any route for delivering a pharmaceutical composition to a patient. Routes of delivery may include non-invasive peroral (through the mouth), topical (skin), transmucosal (nasal, buccal/sublingual, vaginal, ocular and rectal) and inhalation routes, as well as parenteral routes, and other methods known in the art. Parenteral refers to a route of delivery that is generally associated with injection, including intraorbital, infusion, intraarterial, intracarotid, intracapsular, intracardiac, intradermal, intramuscular, intraperitoneal, intrapulmonary, intraspinal, intrasternal, intrathecal, intrauterine, intravenous, subarachnoid, subcapsular, subcutaneous, transmucosal, or transtracheal. Via the parenteral route, the compositions may be in the form of solutions or suspensions for infusion or for injection, or as lyophilized powders.

"Modulation" or "modulates" or "modulating" as used herein refers to upregulation (i.e., activation or stimulation), down regulation (i.e., inhibition or suppression) of a response or the two in combination or apart.

"Pharmaceutically acceptable excipients" refer to an excipient that is useful in preparing a pharmaceutical composition that is generally safe, non-toxic, and desirable, and includes excipients that are acceptable for veterinary use as well as for human pharmaceutical use. Such excipients may be solid, liquid, semisolid, or, in the case of an aerosol composition, gaseous. Examples of excipients include but are not limited to starches, sugars, microcrystalline cellulose, diluents, granulating agents, lubricants, binders, disintegrating agents, wetting agents, emulsifiers, coloring agents, release agents, coating agents, sweetening agents, flavoring agents, perfuming agents, preservatives, antioxidants, plasticizers, gelling agents, thickeners, hardeners, setting agents, suspending agents, surfactants, humectants, carriers, stabilizers, pH buffering agents and combinations thereof.

"Promote" and/or "promoting" as used herein refer to an augmentation in a particular behavior of a cell or organism.

"Subject", "individual", or "patient", as used herein includes all animals, including mammals and other animals, including, but not limited to, companion animals, farm animals and zoo animals. The term "animal" can include any living multi-cellular vertebrate organisms, a category that includes, for example, a mammal, a bird, a simian, a dog, a cat, a horse, a cow, a rodent, and the like. Likewise, the term "mammal" includes both human and non-human mammals. In various embodiments, a subject, individual or patient refers to a human being.

A "patient in need of" or "subject in need" of treatment for a particular disease, disorder, or condition may be a subject suspected of having that disease, disorder, or condition, diagnosed as having that disease, disorder, or condition, already treated or being treated for that disease, disorder, or condition, not treated for that disease, disorder, or condition, or at risk of developing that disease, disorder, or condition.

"Therapeutically effective amount" as used herein refers to the quantity of a specified composition, or active agent in the composition, sufficient to achieve a desired effect in a subject being treated. A therapeutically effective amount may vary depending upon a variety of factors, including but not limited to the physiological condition of the subject (including age, sex, disease type and stage, general physical condition, responsiveness to a given dosage, desired clinical effect) and the route of administration. One skilled in the clinical and pharmacological arts will be able to determine a therapeutically effective amount through routine experimentation.

"Treat," "treating" and "treatment" as used herein refer to both therapeutic treatment and prophylactic or preventative measures, wherein the object is to prevent or slow down (lessen) the targeted condition, disease or disorder (collectively "ailment") even if the treatment is ultimately unsuccessful. Those in need of treatment may include those already with the ailment as well as those prone to have the ailment or those in whom the ailment is to be prevented.

"Senescence" occurs when a cell is too damaged to continue dividing and therefore its growth is curtailed. Senescent cells may begin leaching out harmful proteins and other compounds that can damage cells around them, leading to inflammation and eventually cell death. Senolytics are a class of drugs which selectively induce death of senescent cells. In some embodiments, senoytics reverse damages done by senescent cells.

"Retrograde signaling" refers to a process where a signal travels backwards from a target source to its original source. For example, mitochondrial retrograde signaling is a pathway of communication from mitochondria to the nucleus.

Mitochondria are thought to have transferred their genome to the host nucleus, leaving chromosomal "doppelgangers", through the process of Nuclear Mitochondrial DNA-Transfer or nuclear insertions of mitochondrial origin (NUMTs). NUMTS come in various sizes from all parts of the mitochondrial DNA (mtDNA) with various degrees of homology with the original sequences. Entire mtDNA can be found in the nuclear genome, although in most cases with substantial sequence degeneration. Most NUMTs are small insertions of <500 bp and only 12.85% are >1500 bp. The percentage identity is inversely correlated with size and the mean percentage between NUMTs and mtDNA is 79.2% with a range of 63.5% to 100% identity.

Mitochondrial DNA (mtDNA) replication and transcription starts are regulated by nuclear-encoded proteins and is thought to be transcribed as a single polycistronic precursor that is processed into individual genes by excising the strategically positioned 22 tRNAs (tRNA punctuation model), giving rise to two rRNAs and 13 mRNA.

The human mitochondrion has two promoters in the heavy strand (major and minor) in close proximity, and one in the light strand, thereby giving rise to three different single polycistronic transcripts. The heavy major promoter is responsible for 80% of all mitochondrial RNA (mtRNA) transcripts. Although the entire gene is thought to be transcribed as a single transcript, the abundance of individual rRNA, tRNA, and mRNA transcripts varies greatly, and the rRNAs are the most abundant. This processing structure indicates an unexplored class of posttranscriptional processing in the mitochondria.

Importantly, many of the mRNA species identified from the mitochondria are discrete smaller length ones that do not map to the traditional mitochondrial protein encoding genes. For example, multiple such mRNAs are observed from the 16S rRNA. Parallel analysis of RNA ends (PARE) reveals a plethora of cleavage sites for the mitochondria. The majority of tRNAs and mRNA have distinct dominant cleavage sites at the 5' termini, but intragenic cleavage sites are especially abundant in rRNAs. Notably, there is compelling evidence from the emerging field of small peptides showing biologi-
cally active peptides of 11-32 amino acids in length which
are encoded by small open reading frames (sORFs) from a
polycistronic mRNA.

Described herein are methods and compositions of new
mitochondrial-derived peptides and synthetic analogs
thereof and methods of using them in cancerous cells,
inflammatory cells, or subjects with a cancer and/or an
inflammatory disease. While looking for biologically active
small, mitochondrially derived peptides (also referred to
mitochondrial-derived peptides or mitochondrial peptides),
the Inventors identified NOSH (ND-One sORF in Humans)
with a potent biological activity against cancer cells while
being safe for healthy cells. NOSH (ND-One sORF in
Humans) is a mitochondrially encoded open reading frame
that leads to the production of a new polypeptide that we call
NOSH, which has biological effects affecting mitochondria,
cell growth, and cell death. This peptide is implicated in
cancer, senescence, and aging. As such, NOSH as well as
synthetic NOSH analogues could be used in slower the
progression of cancer, reducing tumor sizes, and treating
other age-related diseases such as inflammatory diseases,
obesity, and metabolic disorders. These peptides are key
factors in retrograde mitochondrial signaling as well as
mitochondrial gene expression. Compared to the human
nuclear genome, mitochondria have a modest sized circular
genome of ~16,570 bp, which ostensibly includes only 13
protein coding genes, which are all structural components of
the electron transport chain system.

This invention includes the composition of matter of a
family of peptide analogues of NOSH. This invention
includes methods of use for these peptides in these indica-
tions. The invention also includes antibodies and assays for
the detection of the levels of the NOSH peptide in the
circulation and tissues of humans.

Various embodiments provide a composition comprising
a mitochondrial-derived peptide or a synthetic or recombi-
nant analog thereof. In some embodiments, a composition
comprises a mitochondrial-derived peptide that comprises,
or consists of, a peptide with an amino acid sequence of SEQ
ID NO:215, or set forth in SEQ ID NO:215. In some
embodiments, a composition comprises two or more mito-
chondrial-derived peptides selected from SEQ ID NOs:
1-214. In some embodiments, a composition includes a
peptide analog of SEQ ID NO:215, a peptide derivative of
SEQ ID NO:215, or a combination thereof.

In one embodiment, the mitochondrial peptide is about
12-65, 14-40, 16-35, 18-32, 20-32, or 25-32 amino acids in
length. In a particular embodiment, the mitochondrial pep-
tide is about 32 amino acids in length. In one embodiment,
the mitochondrial peptide includes a synthetic amino acid.
In one embodiment, the mitochondrial peptide possesses at
least 25%, 25%, 30%, 35%, 40%, 45%, 50%, 55%, 60%,
65%, 70%, 75%, 80%, 85%, 90%, 95% or more percentage
identity to MRLFGLLLAVRRSGRSLSLMLTLIRGL-
SKRLG (SEQ ID NO:215). In some embodiments, the
mitochondrial peptide possesses at least 87.5% identity to
SEQ ID NO:215; or, the mitochondrial peptide is 28-36
amino acids in length or contains no more than four amino
acids difference (including substitution, deletion, and/or
insertion) compared to SEQ ID NO: 215. In some embodi-
ments, the mitochondrial peptide possesses at least 93%
identity to SEQ ID NO:215; or, the mitochondrial peptide is
30-34 amino acids in length or contains no more than two
amino acids difference (including substitution, deletion,
and/or insertion) compared to SEQ ID NO: 215. In some
embodiments, the mitochondrial peptide possesses at least 80% identity to SEQ ID NO:215; or, the mitochondrial
peptide is 26-38 amino acids in length or contains no more
than six amino acids difference (including substitution,
deletion, and/or insertion) compared to SEQ ID NO: 215. In
some embodiments, amino acids 3-11 and amino acids
18-30 are not replaced or deleted in SEQ ID NO:215. In
various embodiments, substitution of amino acids that dis-
rupt the alpha-helixes (glycine, proline) are bad for activity;
and therefore, in some aspects, the amino acid residues of
SEQ ID NO:215 are not replaced with glycine, not replaced
with proline, or not replaced with either glycine or proline;
and in further aspects, the amino acid residues 3 through 11
and residues 18 through 30 of SEQ ID NO:215 are not
replaced with glycine, not replaced with proline, or not
replaced with either glycine or proline. In various embodi-
ments, replacement with alpha-helix enhancers (alanine,
leucine) improve activity of NOSH (SEQ ID NO:215); and
therefore in some aspects, one or more residues of SEQ ID
NO:215 are independently replaced with alanine, leucine, or
both; and in further aspects, one or more residues 3 through
11 and residues 18 through 30 of SEQ ID NO:215 are
independently replaced with alanine, leucine, or both.

Mitochondrial-derived peptide of SEQ ID NO: 215, in
some embodiments, can be considered as an analog of one
or more peptides of SEQ ID NOs: 1-214. In some embodi-
ments, a composition comprising a peptide of any of SEQ ID
NOs: 1-214 is provided, as well as its analogs or derivatives.
In one embodiment, a composition includes a peptide of
SEQ ID NO:1, and/or a peptide that possesses at least 25%,
25%, 30%, 35%, 40%, 45%, 50%, 55%, 60%, 65%, 70%,
75%, 80%, 85%, 90%, 95% or more percentage identity to
(SEQ ID NO:1). In one embodiment, a composition includes
a peptide of SEQ ID NO:2, and/or a peptide that possesses
at least 25%, 25%, 30%, 35%, 40%, 45%, 50%, 55%, 60%,
65%, 70%, 75%, 80%, 85%, 90%, 95% or more percentage
identity to (SEQ ID NO:2).

One of ordinary skill in the art can establish percentage
identity according to methods known in the art, including
establishing a comparison window between a reference
amino acid sequence and a second amino sequence, to
establish the degree of percentage identity.

In some aspects, the mitochondrial-derived peptide and/or
its analogs possesses a post-translational modification or
other type of modification such as an artificial modification.
In various embodiments, this includes for example, pegy-
lation, fatty-acid conjugation lipidation, repeat polypeptide
extension, the fragment crystallizable region of immuno-
globulin G (IgG-Fc), camptothecin (CPT), human serum
albumin (HAS), elastin-like polypeptide (ELP), transferrin,
or albumin modification, among others.

In various embodiments described herein is a peptide, and
the peptide is 12-65 amino acids in length. In various
embodiments, the peptide at position 1 (i.e., first N-terminal
amino acid) is X1, position 2 is (X2) and so on (X3, X4, X5,
X6, etc.), wherein X1, X2, X3, X4, X5, X6, etc. is inde-
pendently selected from a group consisting of a natural or
synthetic amino acid. In some embodiments, the mitochon-
drial peptide (e.g., SEQ ID NO:215) possesses a post-
translational modification or other type of modification such
as an artificial modification. For example, modifications
could include formylation, phosphorylation, acetylation at
corresponding X1, X2, X3, X4, X5, and/or X6, etc. positions
in analogs thereof. In various embodiments, the peptide
possesses at least 25%, 25%, 30%, 35%, 40%, 45%, 50%,
55%, 60%, 65%, 70%, 75%, 80%, 85%, 90%, 95% or more
percentage identity to MRLFGLLLAVRRSGRSLSLMLT-
LIRGLSKRLG (SEQ ID NO:215). In various embodiments, the peptide is 75%, 80%, 85%, 90%, 95% or more percentage identity to a portion of MRLFGLLLAVRRS-GRSLSLMLTLIRGLSKRLG (SEQ ID NO:215), including for example, three or more, five or more, ten or more, fifteen or more, twenty or more, twenty five or more amino acids of MRLFGLLLAVRRSGRSLSLMLTLIRGLSKRLG (SEQ ID NO:215), wherein the portion begins at X1, X2, X3, X4, etc. This includes, any of the sequences in Table 1. In various embodiments, the peptide includes one or more of the aforementioned portions of MRLFGLLLAVRRS-GRSLSLMLTLIRGLSKRLG (SEQ ID NO:215), further including about 6-9 amino acids of X11 to X18 of MRLFGLLLAVRRSGRSLSLMLTLIRGLSKRLG (SEQ ID NO:215).

Various embodiments provide methods of treating a disease and/or condition using a mitochondrial-derived peptide and/or analogs, derivatives thereof including administering a quantity of the mitochondrial-derived peptide and/or analogs, derivative thereof, e.g., in a pharmaceutical composition with one or more pharmaceutically acceptable excipient, to a subject in need of treatment. In one embodiment, the mitochondrial peptide is a MRLFGLLLAVRRS-GRSLSLMLTLIRGLSKRLG (SEQ ID NO:215), an analog or derivative thereof. In one embodiment, the peptide is about 12-65 amino acids in length. In one embodiment, the mitochondrial peptide is about 32 amino acids in length. In other embodiments, the peptide administered possesses at least 80%, 87.5%, 90%, 93% sequence identity to SEQ ID NO:215. In one embodiment, the peptide administered is selected from Table 1.

In one embodiment, the quantity of the mitochondrial peptide administered is a therapeutically effective amount of the mitochondrial peptide. In one embodiment, the subject is a mammal. In one embodiment, the subject is a human.

In various embodiments, administration of NOSH or its analogs decreases mitochondrial function.

In various embodiments, administration of NOSH and/or its analogues decreases cancer cell viability.

In various embodiments, administration of NOSH or its analogs to healthy mice has no grossly toxic effects.

In various embodiments, administration of NOSH or its analogs induces autophagy.

In various embodiments, one or more NOSH and its analogs are administered as a senolytic drug, which selectively kills cells that are senescent.

In various embodiments, one or more of NOSH and its analogs are administered as an immunomodulator, increasing the immune response.

In various embodiments, the disease and/or condition suitable for treatment with the mitochondrial peptide or analogue composition described includes cancer. In various embodiments, cancers are lung cancer, prostate cancer, colorectal cancer, stomach cancer, breast cancer, colorectal cancer, cervical cancer, melanoma, skin cancer, among others.

In various embodiments, disease and/or condition suitable for treatment with the mitochondrial peptide or analogue composition described includes cancer. In various embodiments, cancers are lung cancer, prostate cancer, colorectal cancer, stomach cancer, breast cancer, colorectal cancer, cervical cancer, melanoma, skin cancer, among others. In some embodiments, the cancer for treatment with the mitochondrial peptide or analogue composition described includes prostate cancer. In some embodiments, the cancer for treatment with the mitochondrial peptide or analogue composition described includes ovarian cancer. In some embodiments, the cancer for treatment with the mitochondrial peptide or analogue composition described includes glioblastoma; or a malignant glioblastoma (e.g., grade IV). In some embodiments, the cancer for treatment with the mitochondrial peptide or analogue composition described includes neuroblastoma. In some embodiments, the cancer for treatment with the mitochondrial peptide or analogue composition described includes bladder cancer. In some embodiments, the cancer for treatment with the mitochondrial peptide or analogue composition described includes liver cancer. In some embodiments, the cancer for treatment with the mitochondrial peptide or analogue composition described includes colon cancer. In some embodiments, the cancer for treatment with the mitochondrial peptide or analogue composition described includes breast cancer.

In some embodiments, a subject suitable for treatment with the mitochondrial peptide or analogue composition described has, suffers from, or has been diagnosed with one or more of ovarian cancer, glioblastoma, neuroblastoma, bladder cancer, liver cancer, colon cancer, and breast cancer.

In other embodiments, a subject suitable for treatment with the mitochondrial peptide or analogue composition described has, suffers from, or has been diagnosed with one or more of prostate cancer, glioblastoma, neuroblastoma, bladder cancer, liver cancer, and colon cancer.

In further embodiments, a subject suitable for treatment with the mitochondrial peptide or analogue composition described, or a subject in need of a treatment, a diagnosis, and/or an assay described, is a human at an age above 40 years old, above 50 years old, above 55 years old, above 60 years old, above 65 years old, above 70 years old, above 75 years old, above 80 years old, or above 85 years old.

In further embodiments, he disease and/or condition suitable for treatment with the mitochondrial peptide or analogue composition described includes an inflammatory disease. In some embodiments, the inflammatory disease is inflammatory bowel disease, pelvic inflammatory disease, Crohn's disease, costochondritis, conjunctivitis, bursitis, contact dermatitis, sarcoidosis, bronchiolitis, seroma, or chronic simusitis. In other embodiments, the inflammatory disease is in the nervous system, cardiovascular system, respiratory system, digestion system, accessory digestive organs, integumentary system, musculoskeletal system, urine system, reproductive system, endocrine system, or lymphatic system.

In additional embodiments, disease and/or condition suitable for treatment with the mitochondrial peptide or analogue composition described includes age-related disease or condition. In various embodiments, age-related diseases or conditions are neurodegenerative disorders. In some embodiments, age-related diseases are atherosclerosis and cardiovascular disease, arthritis, cataracts, osteoporosis, type 2 diabetes, hypertension, or Alzheimer's disease.

In various embodiments, the subject does not express the peptide MRLFGLLLAVRRSGRSLSLMLTLIRGLSKRLG (SEQ ID NO:215). In various embodiments, the subject expresses low amounts of MRLFGLLLAVRRS-GRSLSLMLTLIRGLSKRLG (SEQ ID NO:215) relative to a healthy normal subject. In other embodiments, the subject possesses a metabolic signature of low NOSH activity. In other embodiments, the subject possesses a metabolic signature of high or abberrant NOSH activity. In various embodiments, the subject is administered a dominant negative analog and/or derivative of NOSH. A dominant negative analog or derivative generally refers to an analog or derivative with a mutation/substitution/modification resulting in an adverse effect on the normal, wild-type molecule within the same cell. This usually occurs if the product can still interact with the same elements as the wild-type product, but block some aspect of its function.

Described herein is a method of diagnosing an individual for a disease and/or condition. In various embodiments, the method includes selecting a subject, detecting the presence, absence, or expression level of one or more biomarkers, and diagnosing the subject for a disease and/or condition, based on the presence, absence, or expression level of the one or more biomarkers. In various embodiments, the biomarker includes a mitochondrial peptide. In various embodiments, the biomarker includes MRLFGLLLAVRRSGRSLSLMLT-LIRGLSKRLG (SEQ ID NO:215), or any of those peptides in SEQ ID NOs: 1-214. For example, the subject may be diagnosed if expressing a low, high, or aberrant amount of MRLFGLLLAVRRSGRSLSLMLTLIRGLSKRLG (SEQ ID NO:215) relative to a healthy normal subject. In various embodiments, detection of the presence, absence, or expression level of the biomarker includes antibody detection of the one of or more biomarkers, including the use of, for example, a monoclonal antibody, polyclonal antibody, antisera, other immunogenic detection, and mass spectrometry detection methods.

In another embodiment, the biomarker includes a single nucleotide polymorphism (SNP). One of ordinary skill in the art is apprised of the methods capable of SNP detection.

The present invention further provides a method of enhancing efficacy of a treatment disease and/or condition using a mitochondrial peptide, including the steps of selecting a subject in need of treatment, and administering a quantity of the mitochondrial peptide to a subject receiving treatment a disease and/or condition, wherein the mitochondrial peptide enhancing the efficacy of the disease and/or condition, thereby enhancing efficacy of the treatment. In one embodiment, the mitochondrial peptide is administered simultaneously with a composition capable of treating a cancer. In one embodiment, the mitochondrial peptide is administered sequentially, before or after administration, of a composition capable of treating a disease and/or condition. In one embodiment, the subject is a human. For example, the mitochondrial peptides and analog compositions of the invention can be co-administered with other therapeutic agents for the treatment of cancer, including for example cancers such as lung cancer, prostate cancer, colorectal cancer, stomach cancer, breast cancer, colorectal cancer, cervical cancer, melanoma, skin cancer, among others. Co-administration can be simultaneous, e.g., in a single pharmaceutical composition or separate compositions. The compositions of the invention can also be administered separately from the other therapeutic agent(s), e.g., on an independent dosing schedule.

In various embodiments, the present invention further provides a pharmaceutical composition. In one embodiment, the pharmaceutical composition includes a mitochondrial peptide and a pharmaceutically acceptable carrier. In one embodiment, the mitochondrial peptide is MRLFGLL-LAVRRSGRSLSLMLTLIRGLSKRLG (SEQ ID NO:215). In various embodiments, the peptide is 75%, 80%, 85% or more percentage identity to a portion of MRLFGLL-LAVRRSGRSLSLMLTLIRGLSKRLG (SEQ ID NO:215), including for example, three or more, five or more, ten or more, fifteen or more, twenty or more, twenty-five or more amino acids of MRLFGLLLAVRRSGRSLSLMLTLIRGL-SKRLG (SEQ ID NO:215), wherein the portion begins at X1, X2, X3, X4, etc. This includes, any of the sequences in Table 1. In various embodiments, the peptide includes one or more of the aforementioned portions of MRLFGLL-LAVRRSGRSLSLMLTLIRGLSKRLG (SEQ ID NO:215), further including about 6-9 amino acids of X11 to X18 of MRLFGLLLAVRRSGRSLSLMLTLIRGLSKRLG (SEQ ID NO:215).

In some embodiments, the bioactive mitochondrial peptide is as small as about 6-9 amino-acids, about 9-15 amino acids, about 15-20 amino acid, about 20-25 amino acids, about 25-35 amino acids, about 30-40 amino acids, as well as some that are about 12-65 amino acids in length. In one embodiment, the mitochondrial peptide is about 32 amino acids in length. In one embodiment, the mitochondrial peptide in the pharmaceutical composition includes a therapeutically effective amount of the mitochondrial peptide. In one embodiment, pharmaceutical composition includes one or more mitochondrial peptides and a pharmaceutically acceptable carrier. In some embodiments, an amount of the mitochondrial-derived peptide of 0.1-20 μM is administered or added to a sample containing tumor cells. In some embodiments, an amount of 0.1-0.5, 0.5-1, 1-2, 2-3, 3-4, 4-5, 5-6, 6-7, 7-8, 8-9, 9-10, 10-12, 12-14, 14-16, 16-18, or 18-20 μM, or any range comprising an upper end and a lower end selected from these numbers, is administered or added to a sample. In some embodiments, a pharmaceutical composition includes a mitochondrial-derived peptide at 1-10 mg, 10-50 mg, 50-100 mg, 100-300 mg, 300-500 mg, 500 mg-1 g, 1 g-5 g, or 5 g-10 g. In some embodiments, the amount of a mitochondrial-derived peptide is administered at a dose 0.1-1 mg/kg, 1-10 mg/kg, 10-50 mg/kg, 50-100 mg/kg, 100-200 mg/kg, 200-300 mg/kg, 300-400 mg/kg, 400-500 mg/kg, 500-600 mg/kg, 600-700 mg/kg, 700-800 mg/kg, 800-900 mg/kg, 0.9-1 g/kg, 1-5 g/kg, 5-10 g/kg to a subject.

In various embodiments, the present invention further provides a method of manufacturing a mitochondrial peptide. In one embodiment, the method of manufacturing includes the steps of providing one or more polynucleotides encoding a mitochondrial peptide, expressing the one or more polynucleotides in a host cell, and extracting the mitochondrial peptide from the host cell. In one embodiment, the method of manufacturing includes the steps of expressing the one or more polynucleotides in a host cell, and extracting the mitochondrial peptide from the host cell. In one embodiment, the one or more polynucleotides are a sequence encoding MRLFGLLLAVRRSGRSLSLMLTLIR-GLSKRLG (SEQ ID NO:215), or a mitochondrial peptide possessing at least 25%, 25%, 30%, 35%, 40%, 45%, 50%, 55%, 60%, 65%, 70%, 75%, 80%, 85%, 90%, 95% or more percentage identity to MRLFGLLLAVRRSGRSLSLMLT-LIRGLSKRLG (SEQ ID NO:215). In various embodiments, the peptide is 75%, 80%, 85%, 90%, 95% or more percentage identity to a portion of MRLFGLLLAVRRS-GRSLSLMLTLIRGLSKRLG (SEQ ID NO:215), including for example, three or more, five or more, ten or more, fifteen or more, twenty or more, twenty five or more amino acids of MRLFGLLLAVRRSGRSLSLMLTLIRGLSKRLG (SEQ ID NO:215), wherein the portion begins at X1, X2, X3, X4, etc.

In another embodiment, the method of manufacturing includes the steps of peptide synthesis using liquid-phase synthesis or solid-phase synthesis. In one embodiment, the solid-phase synthesis is Fmoc or BOC synthesis.

EXAMPLES

Described herein are non-limiting examples of the claimed invention.

Example 1

A family of new peptide analogues were prepared for use as a therapy for age-related diseases, including cancer.

While looking for biologically active small, mitochondrially derived peptides, the Inventors found NOSH (ND-One sORF in Humans) that had potent biological activity.

Example 2

Preliminary Results

Figure 2:
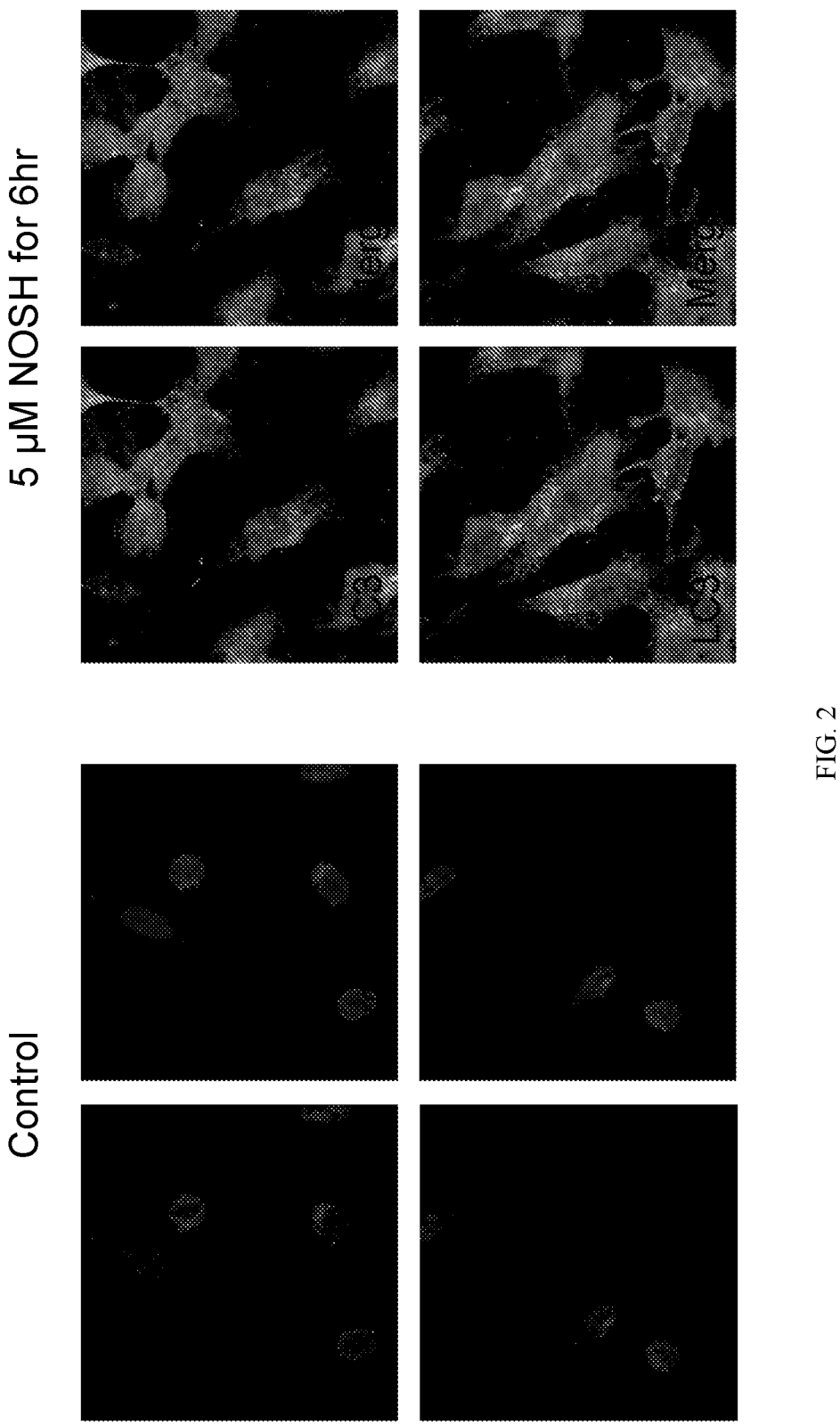
FIG. 2. NOSH increases autophagy. The level of LC3 is increased in PC3 cells treated with 5 μM NOSH for 6 hours.

AS shown in FIG. 1. NOSH was safe in mice. Further, NOSH increased autophagy. The level of autophagy-related protein microtubule-associated protein 1 light chain 3 (LC3) was increased in PC3 cells treated with 5 μM NOSH for 6 h. FIG. 2.

Example 3

Mitochondrial Function

Figure 3:
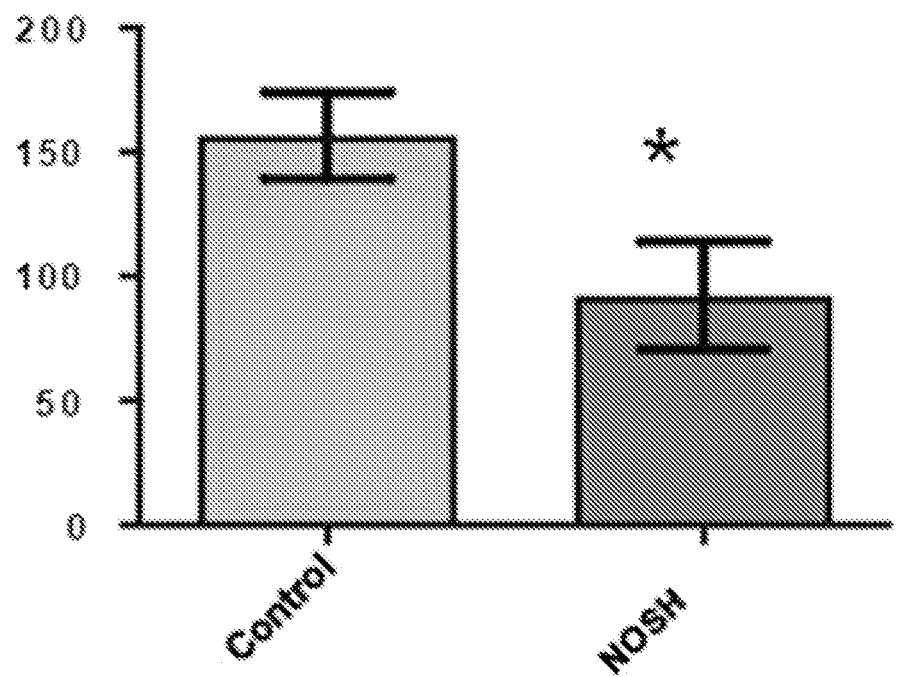
FIG. 3. NOSH alters mitochondrial function. Membrane potential was measured by JC-1 staining.
Figure 3:
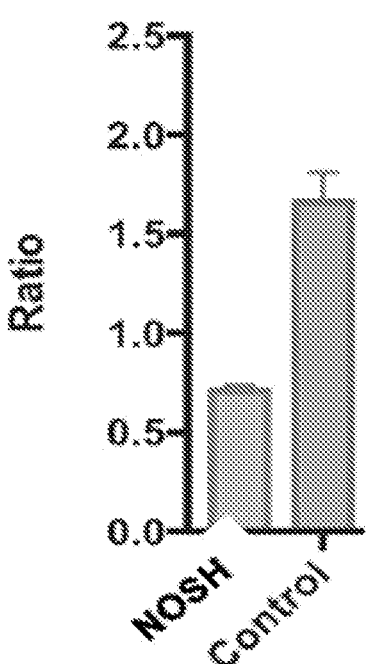

Without being bound by any theory, preliminary results showed that Nosh altered mitochondrial function. This was further confirmed by measurements of membrane potential by JC-1 staining. FIG. 3.

Figure 4:
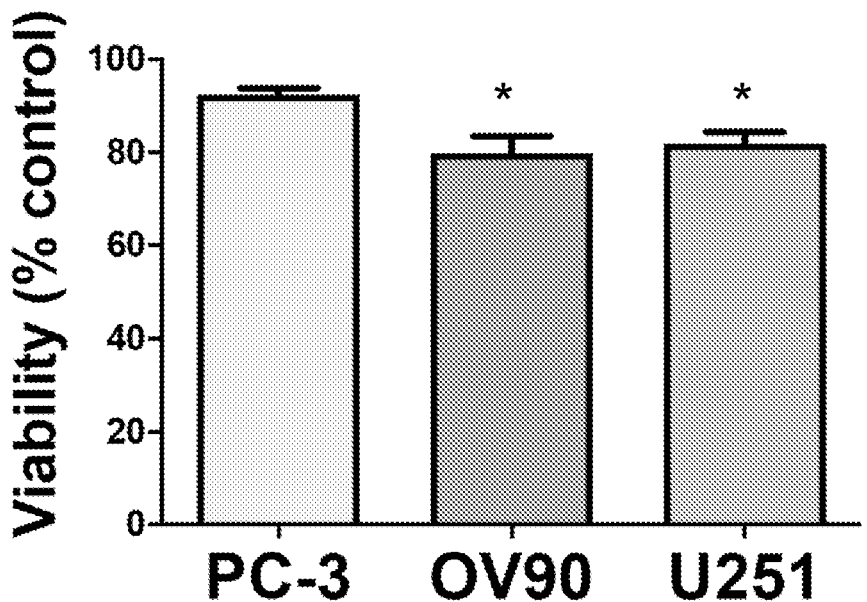
FIG. 4. NOSH reduces viability of tumor cells. Viability was measured by LDH release into the media.

Moreover, as measured by lactate dehydrogenase (LDH) release into the media, NOSH reduced Cell Viability in Tumor Cells. FIG. 4. PC-3 is a human prostate cancer cell line. OV90 is an ovarian cancer cells. U251 cell line was derived from a malignant glioblastoma tumor.

Example 4

Functional Properties

Figure 5A:
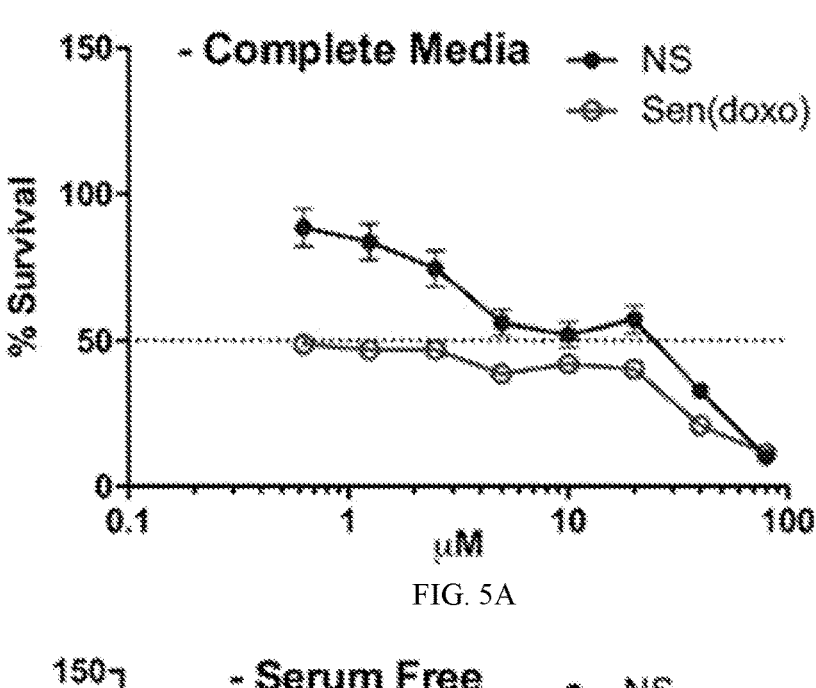
FIG. 5A-5E depict that NOSH acts as a senolytic peptide, preferentially reducing viability of senescent cells.
Figure 5B:
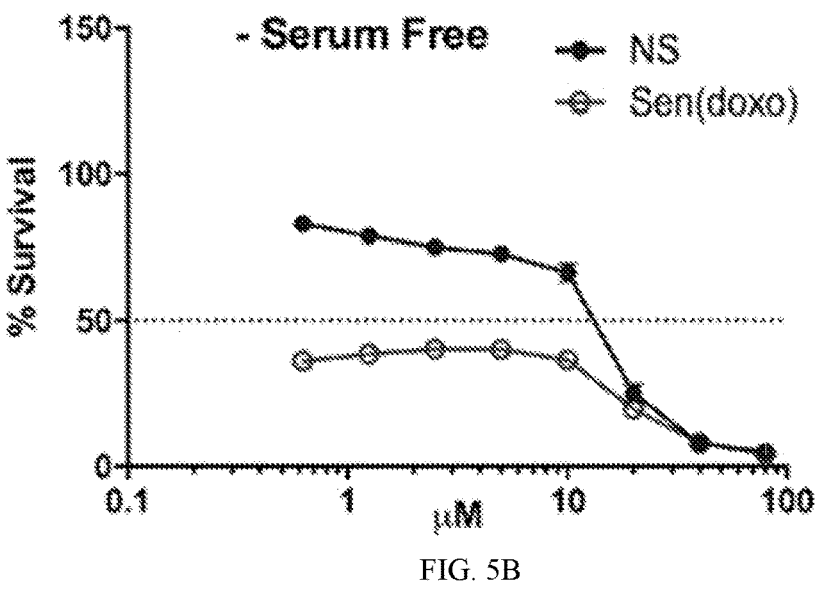
Figure 5C:
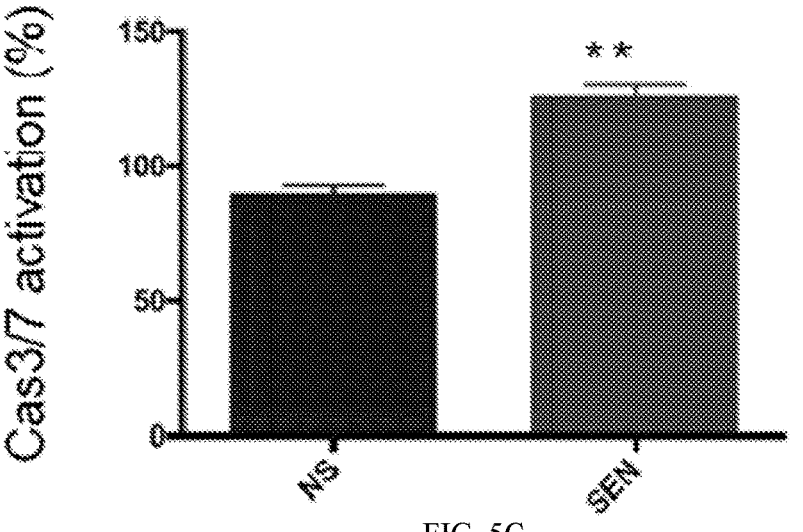
Figure 5D:
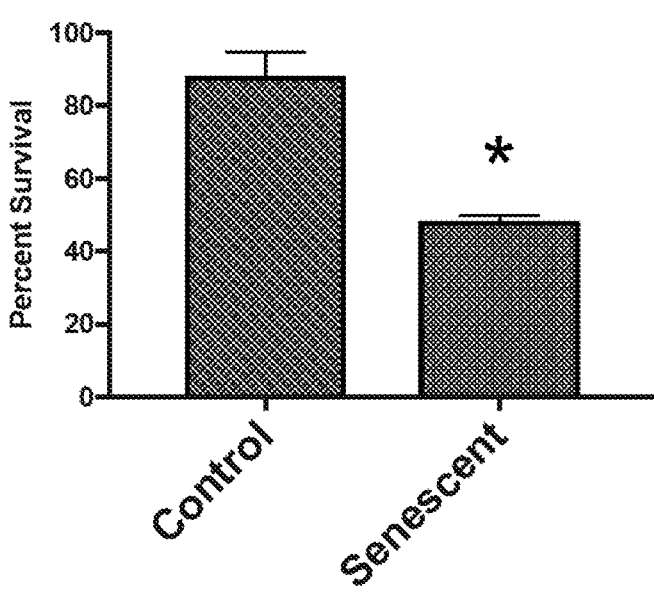
Figure 5E:
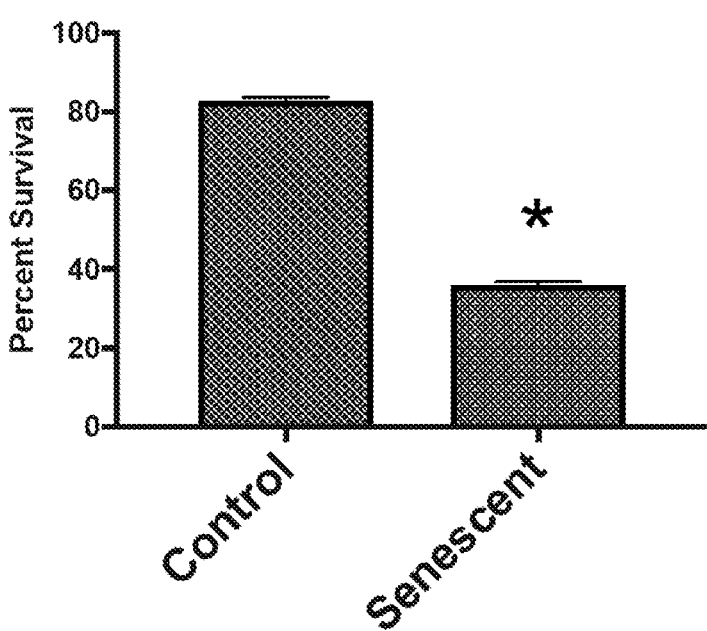

NOSH acts as a senolytic peptide, preferentially reducing viability of senescent cells. FIG. 5A and FIG. 5B. Treatment with 10 μM NDDP4 for 24 hr in non-senescent (NS) and senescent cells showed a higher caspase-3/7 activation in senescent cells than in non-senescent cells. Activation of caspase-3 is an essential event during apoptosis. FIG. 5C.

Figure 6:
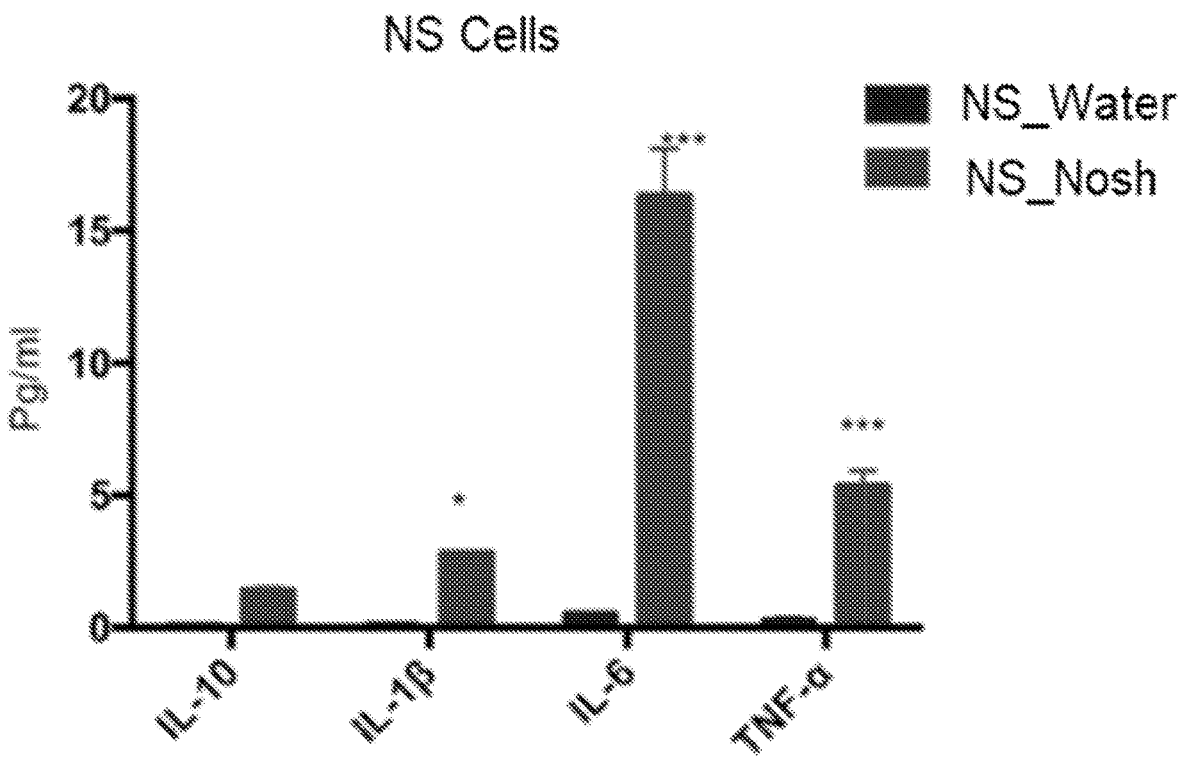
FIG. 6. NOSH induces an inflammatory response in senescent cells (primary dermal fibroblast (HDFa)). Doxorubicin induced the senescent cells. The non-senescent cells and senescent cells were treated with 10 μM NOSH for 24 hr. After 24 hr, conditioned media were collected and measured for the cytokine levels by meso scale discovery (MSD) assay.
Figure 6:
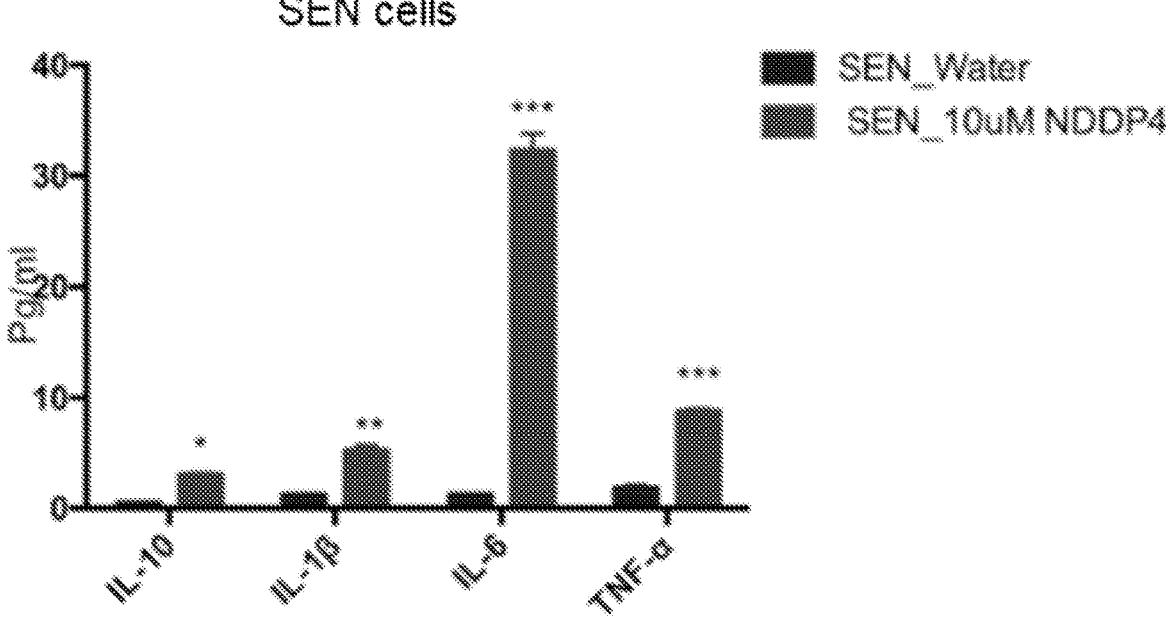

NOSH induced an inflammatory response in senescent cells, for example in doxorubin induced senescent primary dermal fibroblast (HDFa). 10 μM NOSH were incubated for 24 hr in both non senescent cells and senescent cells. After 24 hr, conditioned media collected and measured the cytokine levels by meso scale discovery (MSD) assay. FIG. 6.

Example 5

Analogs

Figure 7:
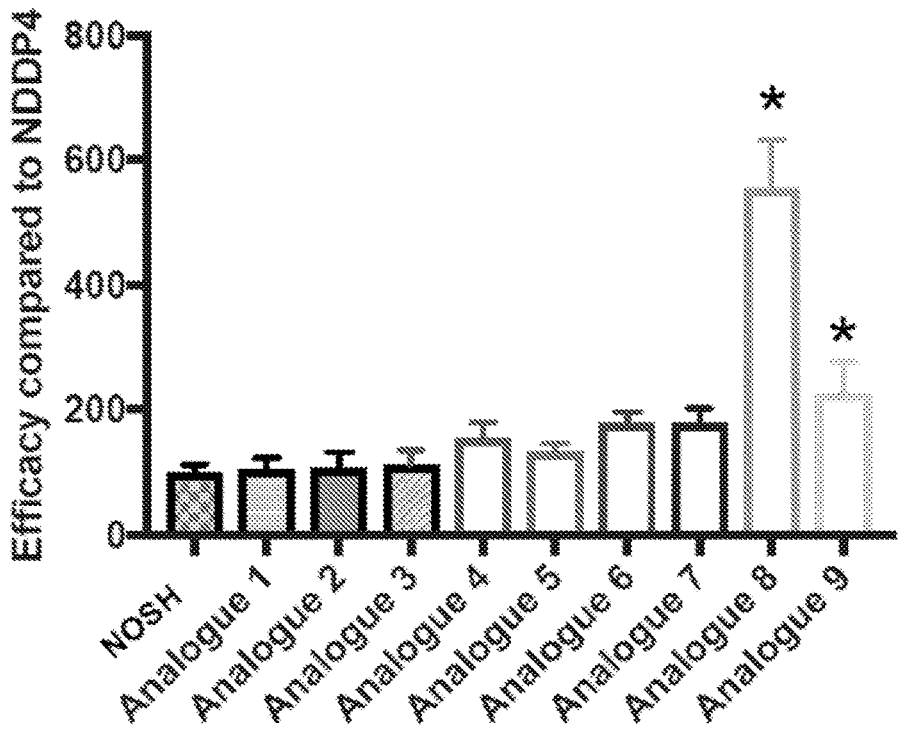
FIG. 7. NOSH analogues with increased efficacy.
Figure 7:
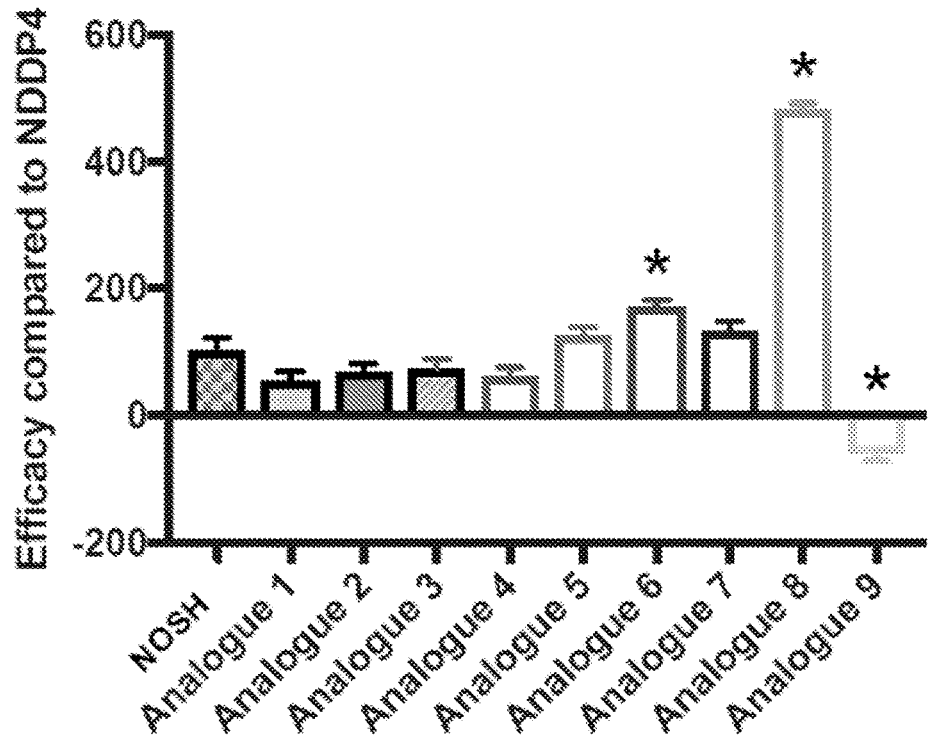

Modifications allowed for generation of NOSH Analogues with increased efficacy. FIG. 7. A table of analogs, along with sequences are shown in Table 1. These analogs were applied in the platforms described herein.

Example 6

Role in Cancer Biology

Figure 8A:
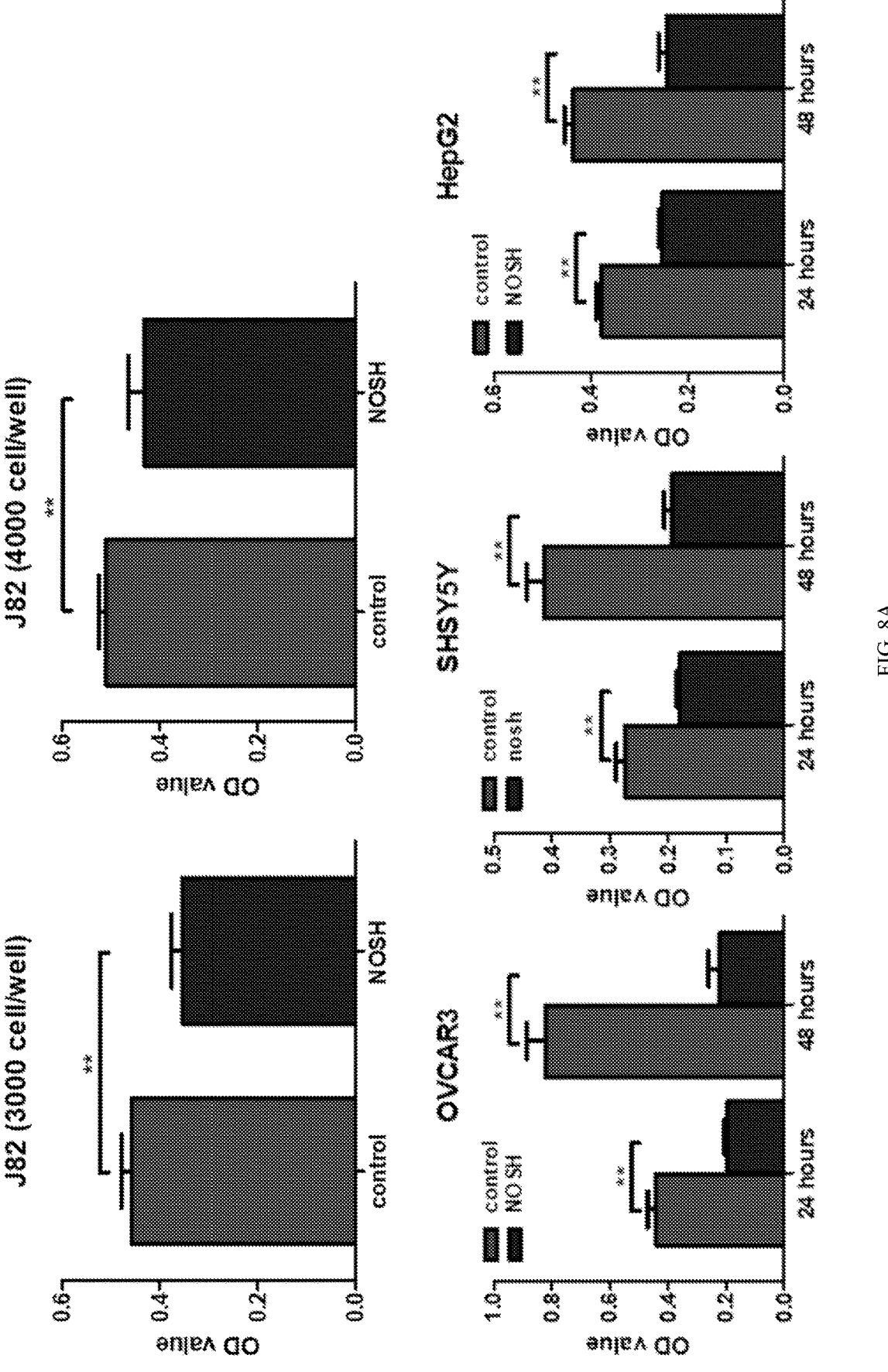
FIGS. 8A and 8B depict that NOSH is effective in decreasing viability of a number of different cancer cell lines.
Figure 8B:
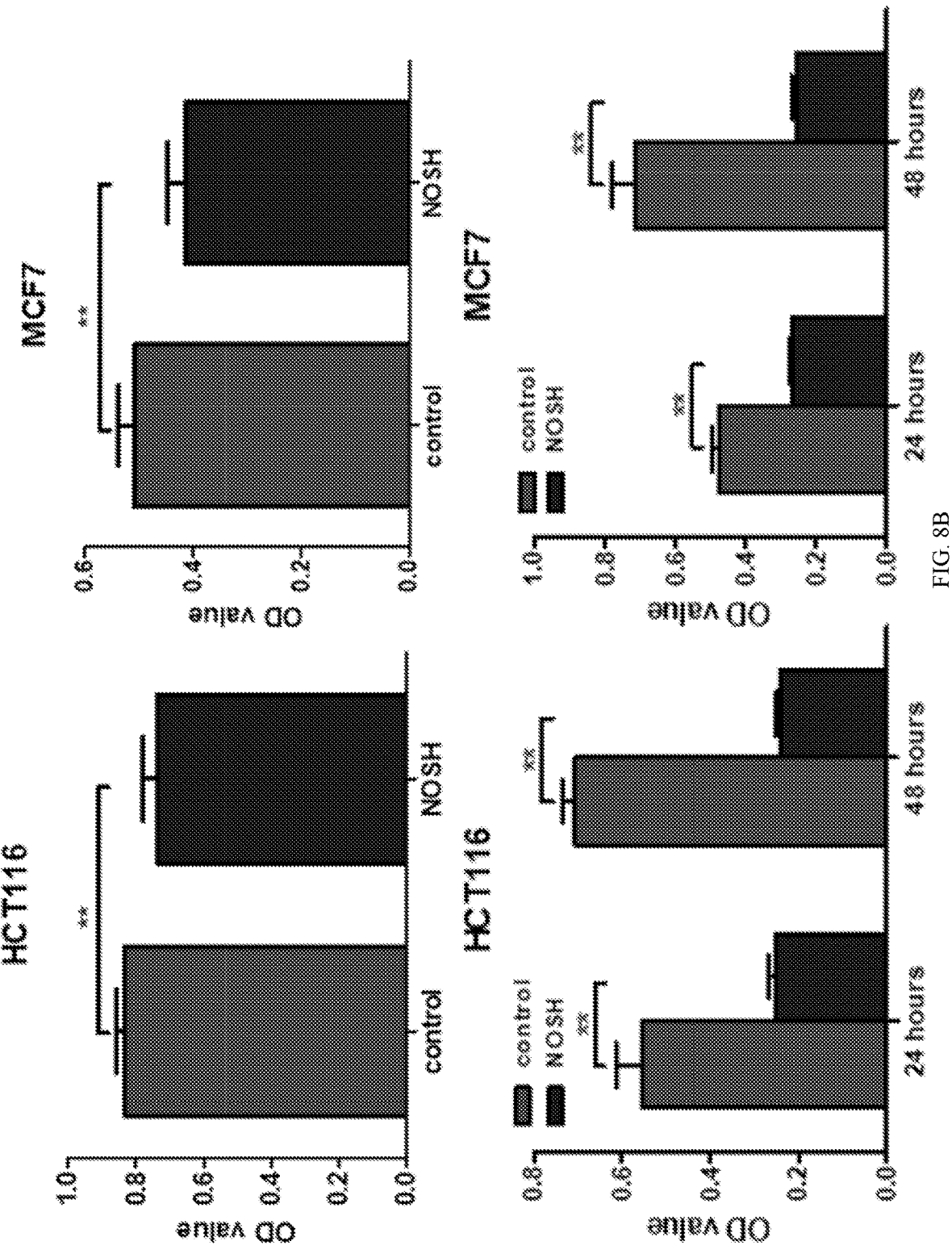
Figure 9:
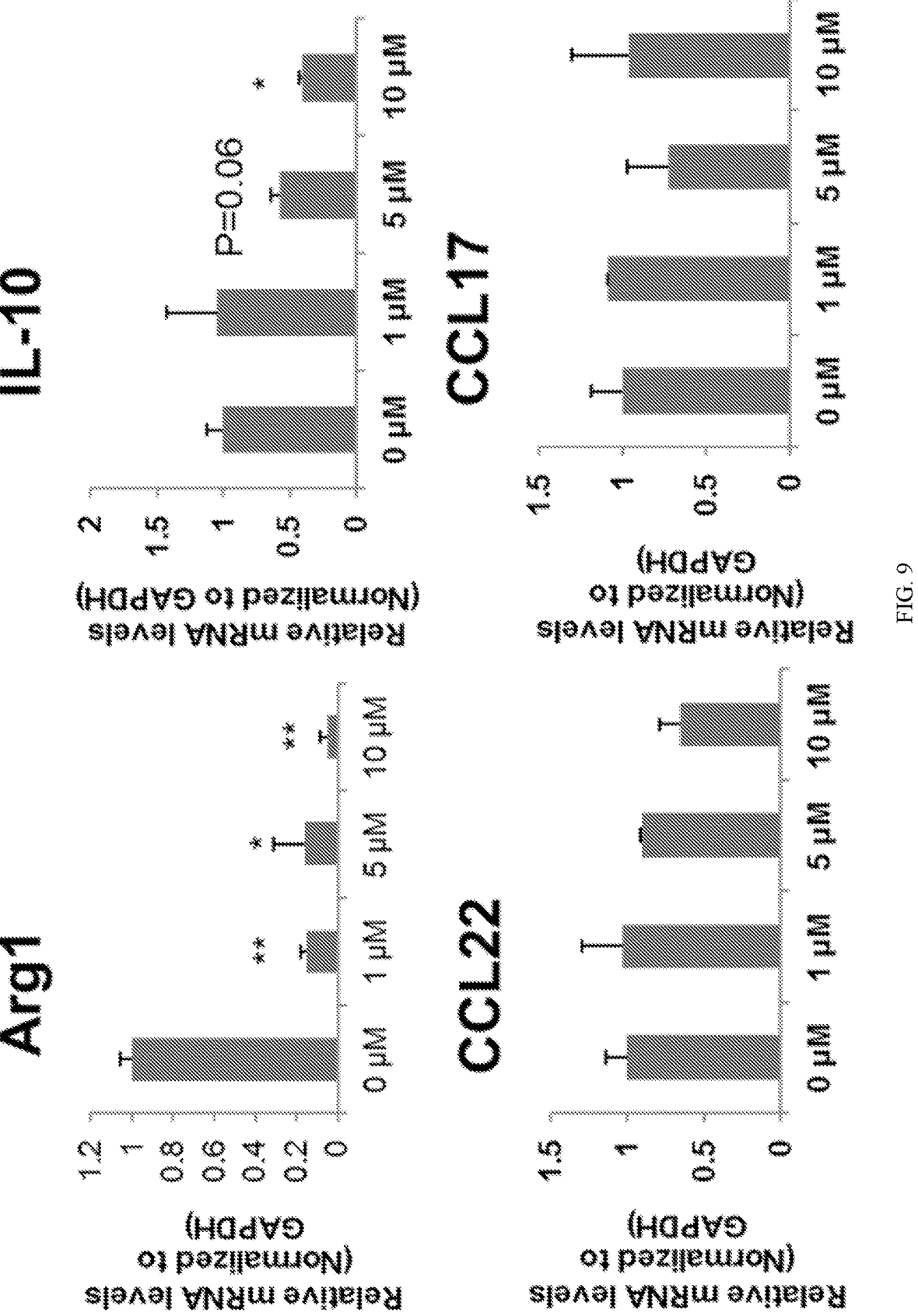
FIG. 9 depicts gene expression in M2 macrophages, demonstrating that NOSH converts M2 Macrophages to M1 Macrophages. THP-1 cells were treated in PMA (200 ng/ml) for 24 hours. Subsequently, medium was changed and PMA was removed. Cells were washed with PBS for three times. Cells were then treated with LPS (100 ng/ml) or IL-4 (20 ng/ml), with different doses of NOSH for 24 hours.
Figure 10:
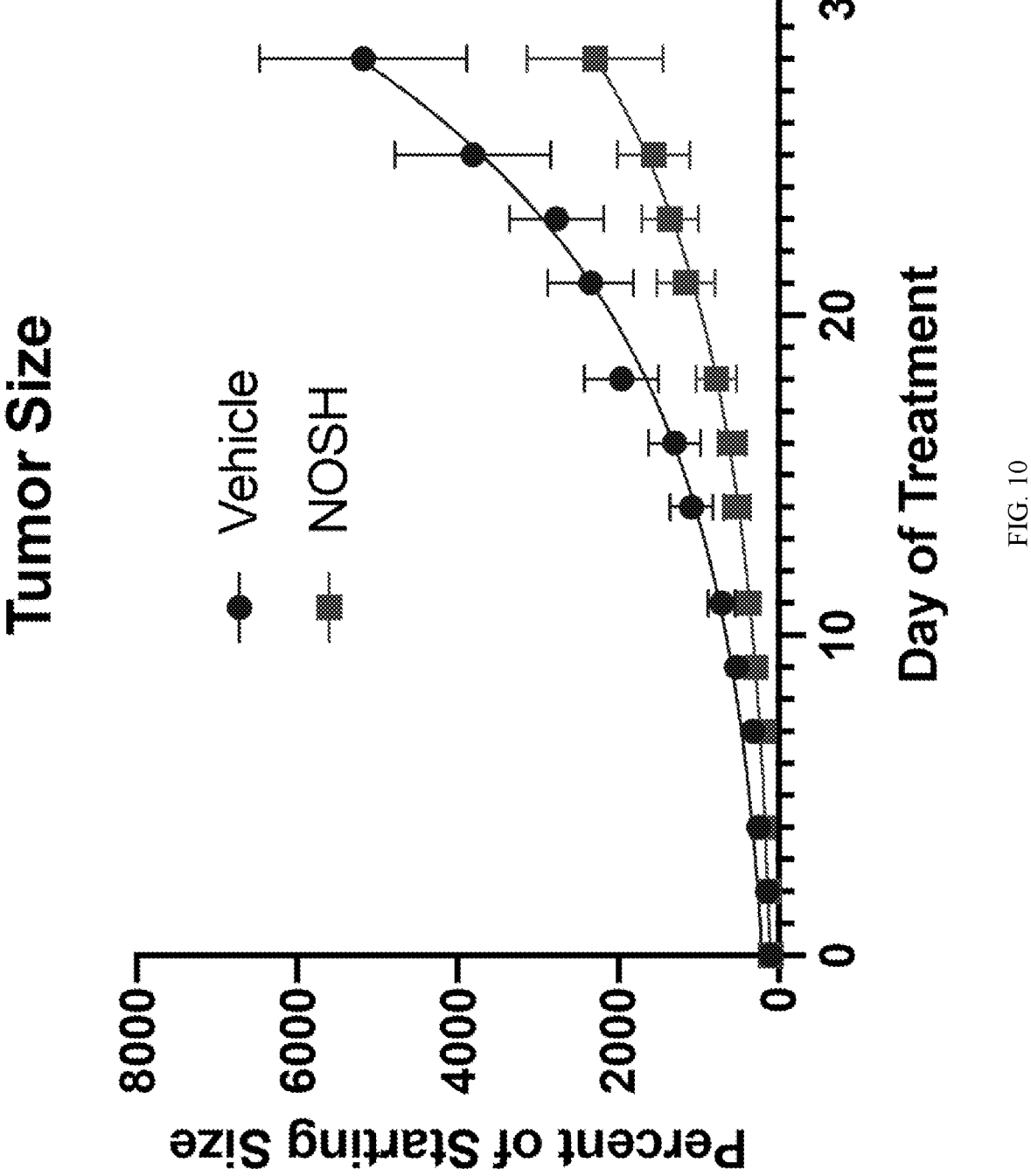
FIG. 10. NOSH reduces tumor size in mice.

As described, NOSH was effective in decreasing viability in a number of different cancer cell lines. FIGS. 8A and 8B. J82 cells are human bladder cancer cells; OVCAR3 is a cell line modeling ovarian carcinoma; SHSYSY is a thrice-subcloned cell line derived from the SK-N-SH neuroblastoma cell line; HepG2 is a human liver cancer cell line; HCT116 is HCT116 is a human colon cancer cell line; and MCF7 is a breast cancer cell line isolated from a 69-year-old woman. Moreover, NOSH converted M2 Macrophages to M1 Macrophages, measured by gene expression in M2 macrophages. Monocytic cells derived from a acute monocytic leukemia patient, i.e., THP-1 cells, were treated with phorbol 12-myristate 13-acetate (PMA) (200 ng/ml) for 24 hours. PMA at this concentration induces differentiation of THP-1 monocytes into macrophages. Medium was changed and PMA removed. Cells were washed with PBS for three times. Cells were then treated with lipopolysaccharide (LPS) (100 ng/ml) or IL-4 (20 ng/ml), with different doses of NOSH for 24 hours. FIG. 10.

Figure 11A:
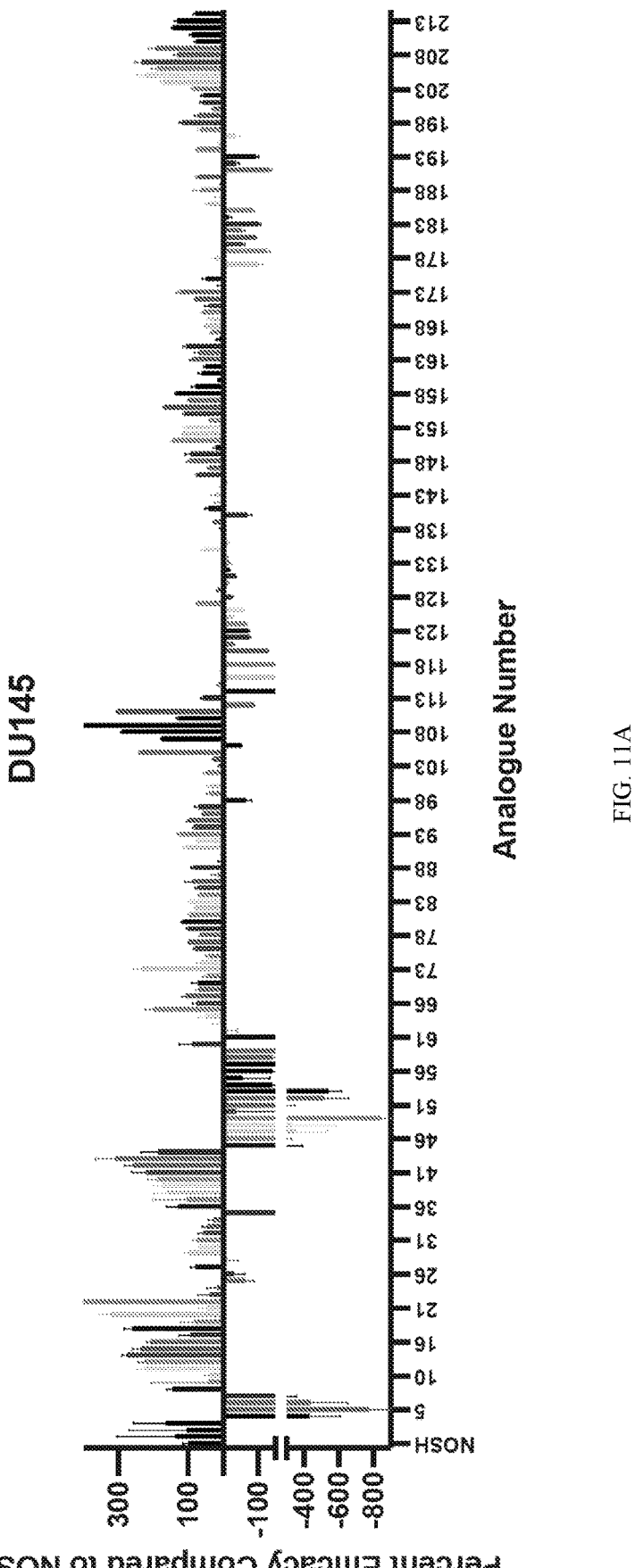
FIG. 11A is a graph depicting efficacy of 214 NOSH analogues in DU145 cells compared to NOSH.
Figure 11B:
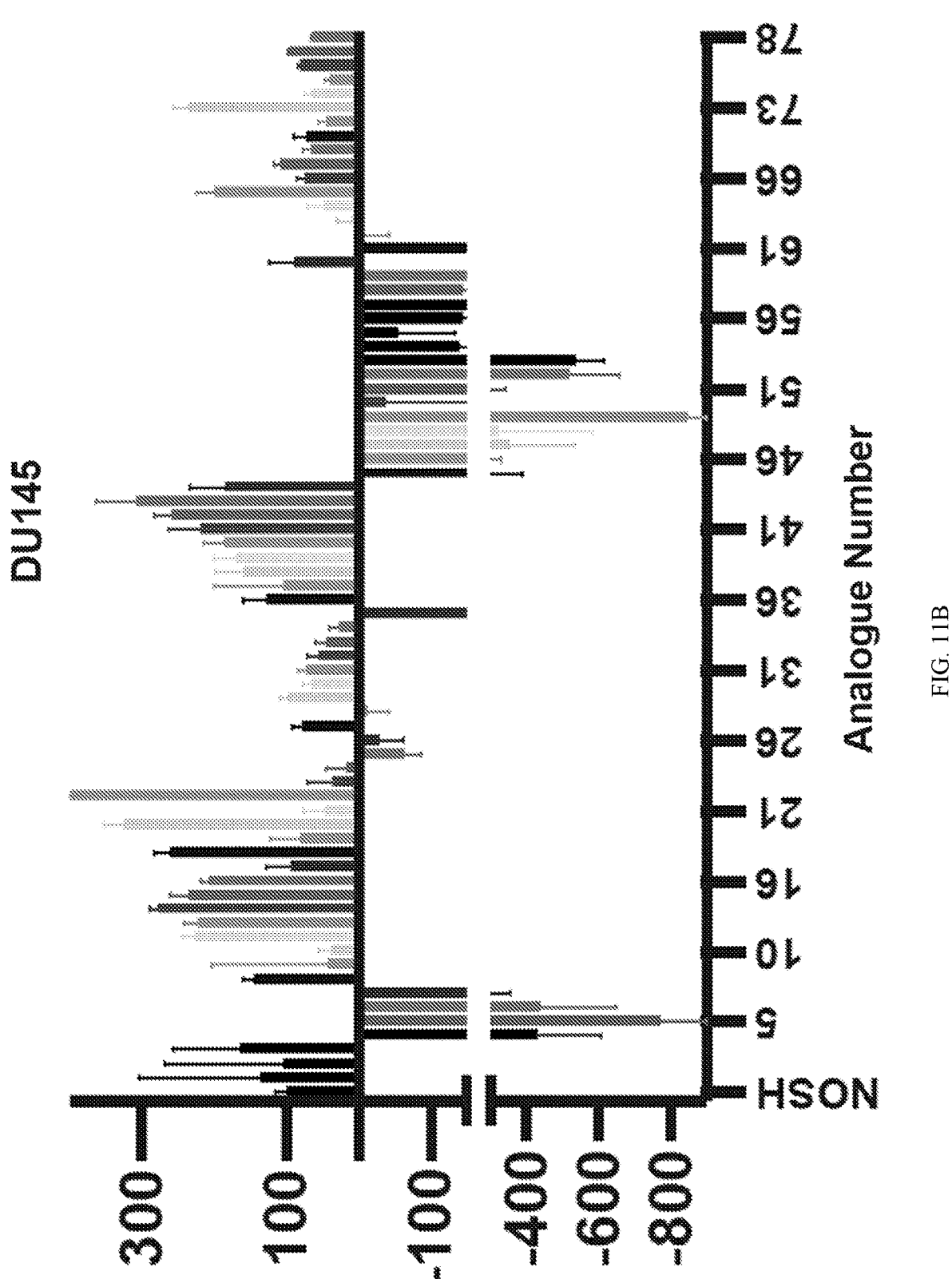
FIG. 11B depicts the efficacy of NOSH analogs (from NOSH-1 to NOSH-78) in DU145 cells compared to NOSH, an enlarged version of relevant data in FIG. 11A.
Figure 11C:
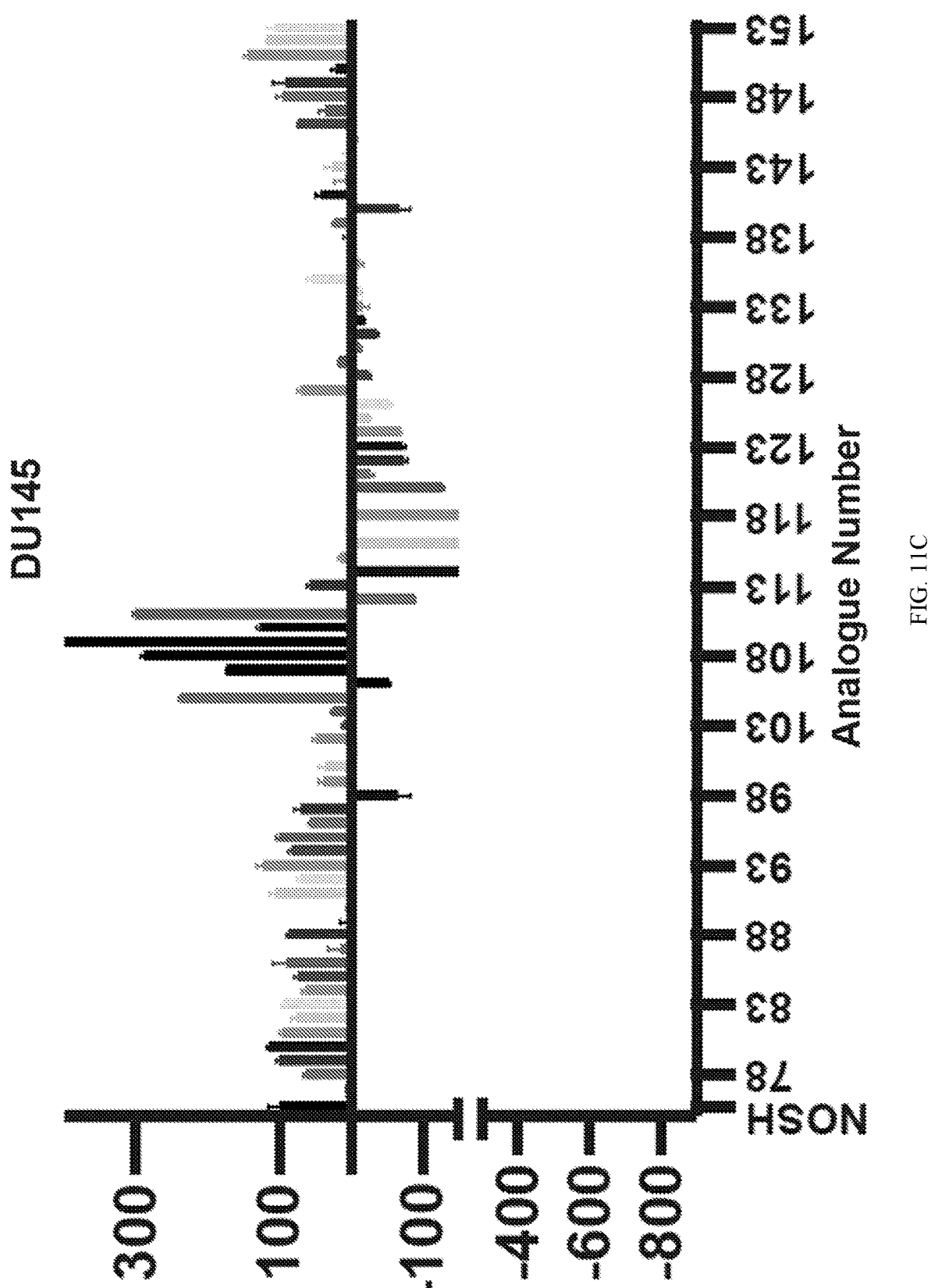
FIG. 11C depicts the efficacy of NOSH analogs (from NOSH-78 to NOSH-153) in DU145 cells compared to NOSH, an enlarged version of relevant data in FIG. 11A.
Figure 11D:
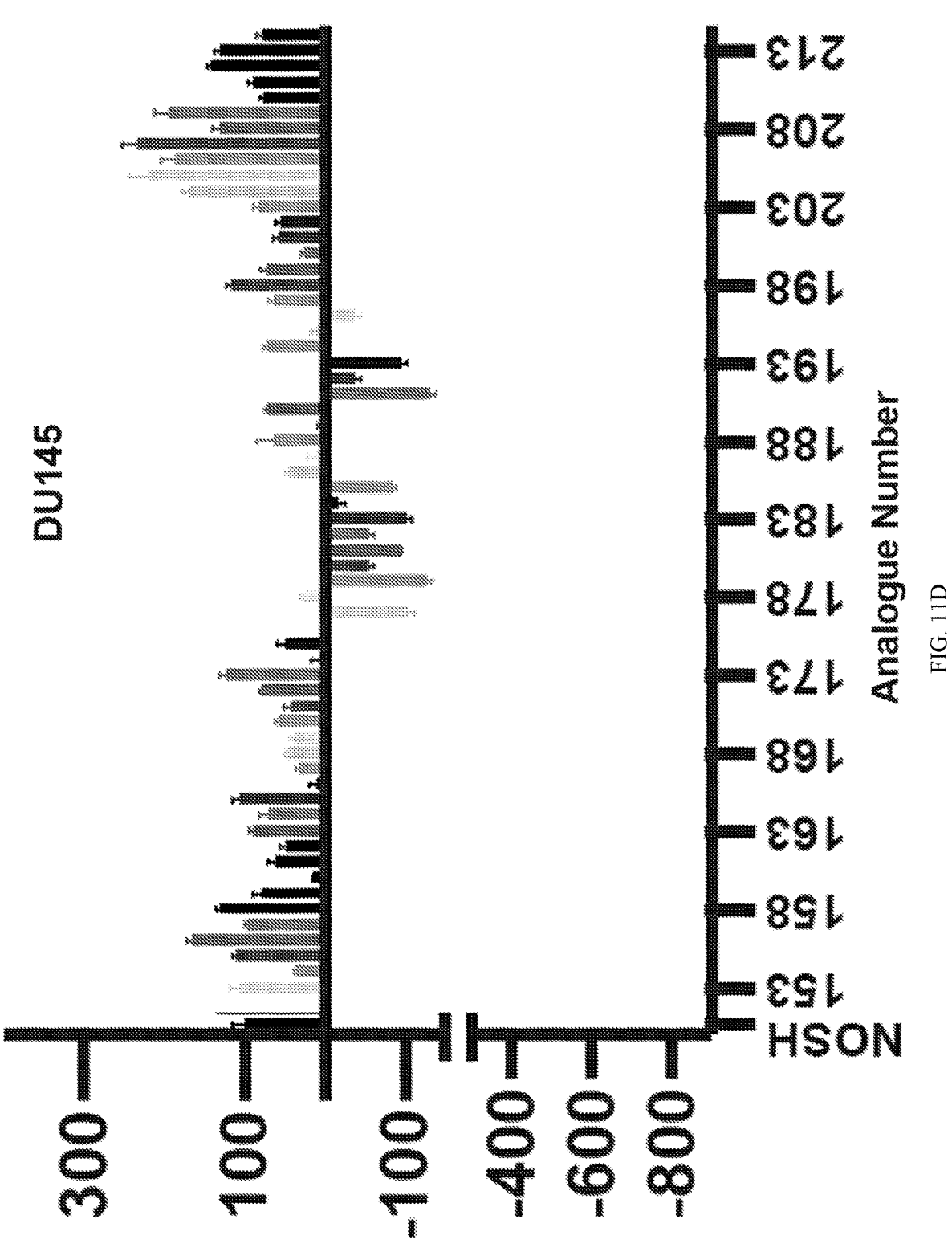
FIG. 11D depicts the efficacy of NOSH analogs (from NOSH-153 to NOSH-214) in DU145 cells compared to NOSH, an enlarged version of relevant data in FIG. 11A.
Figure 12:
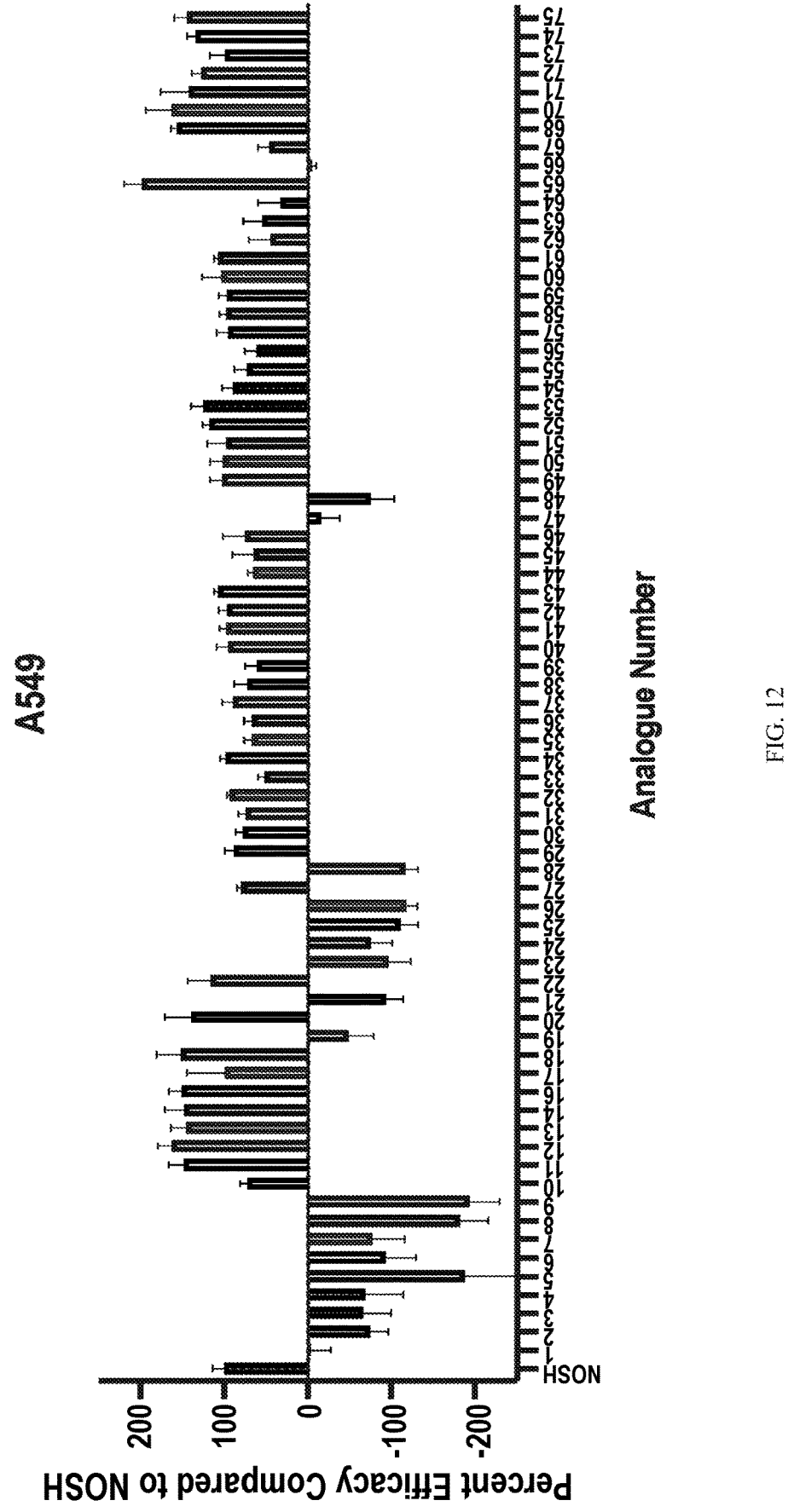
FIG. 12. NOSH analogues efficacy in A549 Cells

These results were affirmed by observations that NOSH reduces tumor size in mice. FIG. 11A. When applied across cell lines, one could observe the effects of NOSH analogs in difference cell lines, including NOSH Analogues in DU145 Cells and NOSH Analogues in A549 Cells. FIGS. 11A and 12, respectively.

Example 7

NOSH Biochemical Structure

Figure 13:
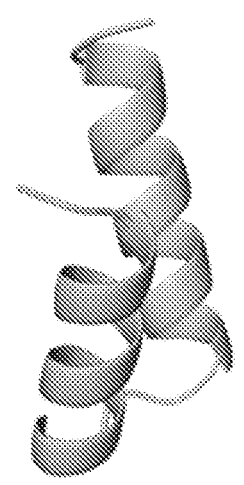
FIG. 13. NOSH structure. NOSH has a predicted double alpha-helix structure where the alpha-helices are predicted to be in amino acids 3-11 and amino acids 18-30. The hinge region between the helices seems to be of importance as mutations in this region significantly alter function.
Figure 13:
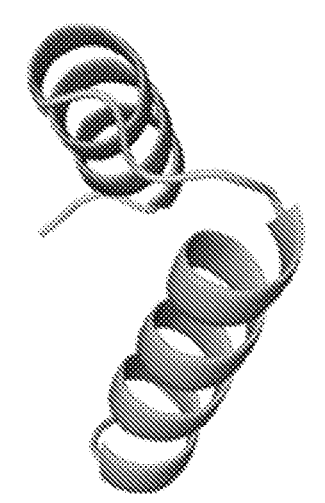
Figure 13:
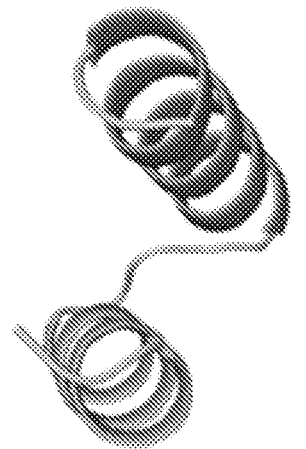

FIG. 13 depicts NOSH structure. NOSH has a predicted double alpha-helix structure where the alpha-helices are predicted to be in AA 3-11 and AA 18-30. The hinge region between the helices seem to be of importance as mutations in this region significantly alter function.

Example 8

NOSH Inhibits Inflammatory Markers

Figure 14:
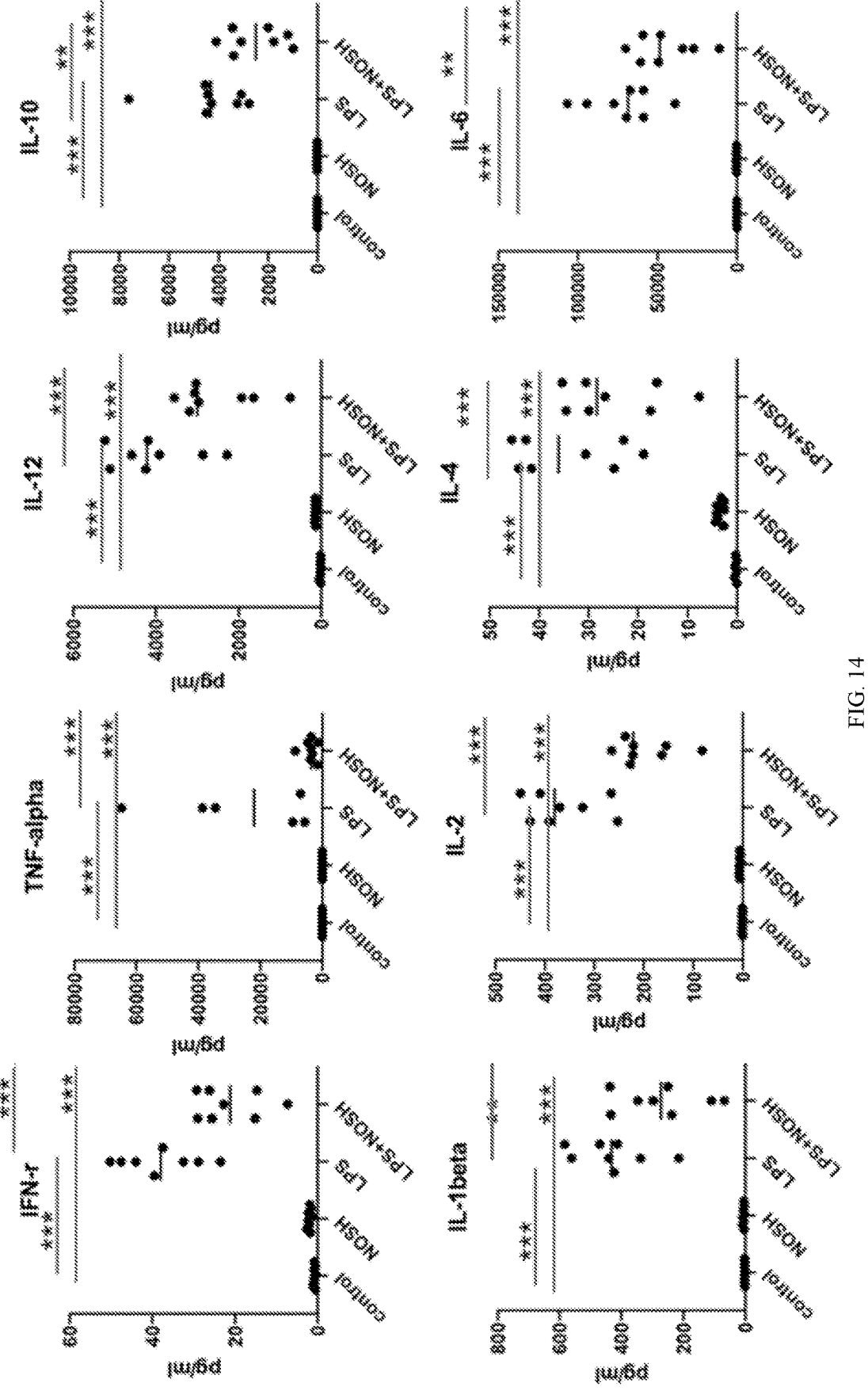
FIG. 14 depicts that NOSH potently inhibits induced inflammatory markers, showing mouse plasma levels of IFNγ, TNF-α, IL-12, IL-10, IL-1β, IL-2, IL-4 and IL-6. 10-week old, male, C57B16/J mice were treated with water or NOSH (10 mg/kg), with or without LPS (10 mg/kg) treatment (n=8/group), and plasma was collected 2 hour later.

FIG. 14 depicts the plasma levels of inflammatory markers induced in mice following LPS (10 mg/kg) administration with or without NOSH (10 mg/kg). Compared to LPS-treated mice, mice administered with NOSH following/concurrently with LPS had a statistically significantly lowered level of inflammatory markers.

TABLE 1

| NOSH Analogs | | |
|---|---|---|
| NOSH | MRLFGLLLAVRRSGRS LSLMLTLIRGLSKRLG | SEQ ID NO: 215 |
| NOSH-1 | MRLFGLLLAVRRDGRS LSLMLTLIRGLSKRLG | SEQ ID NO: 1 |
| NOSH-2 | MRLFGLLLAVRRSGRS LSLMLTLIRGLDKRLG | SEQ ID NO: 2 |
| NOSH-3 | MRLFGLLLAVRRDGRS LSLMLDLIRGLDKRLG | SEQ ID NO: 3 |
| NOSH-4 | GLLLAVRRSGRSLDLM LTLI | SEQ ID NO: 4 |
| NOSH-5 | MRLFGLLLAVRRSGRS | SEQ ID NO: 5 |
| NOSH-6 | LSLMLTLIRGLSKRLG | SEQ ID NO: 6 |
| NOSH-7 | MRLFGLLLAVGGSGRS LSLMLTLIRGLSKRLG | SEQ ID NO: 7 |
| NOSH-8 | MRLFGLLLAVGGSGGS LSLMLTLIRGLSKRLG | SEQ ID NO: 8 |
| NOSH-9 | formylated-MRLFG LLLAVRRSGRSLSLML TLIRGLSKRLG | SEQ ID NO: 9 |
| NOSH-10 | MRLFGLLLAVRRDGRD LDLMLDLIRGLDKRLG | SEQ ID NO: 10 |
| NOSH-11 | MRLFGLLLAVRRDGRD LDLMLDLIRGLSKRLG | SEQ ID NO: 11 |
| NOSH-12 | MRLFGLLLAVRRSGRD LDLMLDLIRGLDKRLG | SEQ ID NO: 12 |

TABLE 1-continued

| NOSH Analogs | | |
|---|---|---|
| NOSH-13 | MRLFGLLLAVRRDGRS LDLMLDLIRGLDKRLG | SEQ ID NO: 13 |
| NOSH-14 | MRLFGLLLAVRRDGRD LSLMLDLIRGLDKRLG | SEQ ID NO: 14 |
| NOSH-15 | MRLFGLLLAVRRDGRD LDLMLTLIRGLDKRLG | SEQ ID NO: 15 |
| NOSH-16 | MRLFGLLLAVRRDGRD LDLMLTLIRGLSKRLG | SEQ ID NO: 16 |
| NOSH-17 | MRLFGLLLAVRRDGRD LSLMLDLIRGLSKRLG | SEQ ID NO: 17 |
| NOSH-18 | MRLFGLLLAVRRDGRD LSLMLTLIRGLDKRLG | SEQ ID NO: 18 |
| NOSH-19 | MRLFGLLLAVRRDGRS LDLMLDLIRGLSKRLG | SEQ ID NO: 19 |
| NOSH-20 | MRLFGLLLAVRRDGRS LDLMLTLIRGLDKRLG | SEQ ID NO: 20 |
| NOSH-21 | MRLFGLLLAVRRSGRD LDLMLDLIRGLSKRLG | SEQ ID NO: 21 |
| NOSH-22 | MRLFGLLLAVRRSGRD LDLMLTLIRGLDKRLG | SEQ ID NO: 22 |
| NOSH-23 | MRLFGLLLAVRRSGRD LSLMLDLIRGLDKRLG | SEQ ID NO: 23 |
| NOSH-24 | MRLFGLLLAVRRSGRS LDLMLDLIRGLDKRLG | SEQ ID NO: 24 |
| NOSH-25 | MRLFGLLLAVRRDGRD LSLMLTLIRGLSKRLG | SEQ ID NO: 25 |
| NOSH-26 | MRLFGLLLAVRRDGRS LDLMLTLIRGLSKRLG | SEQ ID NO: 26 |
| NOSH-27 | MRLFGLLLAVRRDGRS LSLMLDLIRGLSKRLG | SEQ ID NO: 27 |
| NOSH-28 | MRLFGLLLAVRRDGRS LSLMLTLIRGLDKRLG | SEQ ID NO: 28 |
| NOSH-29 | MRLFGLLLAVRRSGRD LDLMLTLIRGLSKRLG | SEQ ID NO: 29 |
| NOSH-30 | MRLFGLLLAVRRSGRD LSLMLDLIRGLSKRLG | SEQ ID NO: 30 |
| NOSH-31 | MRLFGLLLAVRRSGRD LSLMLTLIRGLDKRLG | SEQ ID NO: 31 |
| NOSH-32 | MRLFGLLLAVRRSGRS LDLMLDLIRGLSKRLG | SEQ ID NO: 32 |
| NOSH-33 | MRLFGLLLAVRRSGRS LDLMLTLIRGLDKRLG | SEQ ID NO: 33 |
| NOSH-34 | MRLFGLLLAVRRSGRS LSLMLDLIRGLDKRLG | SEQ ID NO: 34 |
| NOSH-35 | ARLFGLLLAVRRSGRS LSLMLTLIRGLSKRLG | SEQ ID NO: 35 |
| NOSH-36 | MALFGLLLAVRRSGRS LSLMLTLIRGLSKRLG | SEQ ID NO: 36 |
| NOSH-37 | MRAFGLLLAVRRSGRS LSLMLTLIRGLSKRLG | SEQ ID NO: 37 |
| NOSH-38 | MRLAGLLLAVRRSGRS LSLMLTLIRGLSKRLG | SEQ ID NO: 38 |

TABLE 1-continued

| NOSH Analogs | | |
|---|---|---|
| NOSH-39 | MRLFALLLAVRRSGRS LSLMLTLIRGLSKRLG | SEQ ID NO: 39 |
| NOSH-40 | MRLFGALLAVRRSGRS LSLMLTLIRGLSKRLG | SEQ ID NO: 40 |
| NOSH-41 | MRLFGLALAVRRSGRS LSLMLTLIRGLSKRLG | SEQ ID NO: 41 |
| NOSH-42 | MRLFGLLAAVRRSGRS LSLMLTLIRGLSKRLG | SEQ ID NO: 42 |
| NOSH-43 | MRLFGLLLAARRSGRS LSLMLTLIRGLSKRLG | SEQ ID NO: 43 |
| NOSH-44 | MRLFGLLLAVARSGRS LSLMLTLIRGLSKRLG | SEQ ID NO: 44 |
| NOSH-45 | MRLFGLLLAVRASGRS LSLMLTLIRGLSKRLG | SEQ ID NO: 45 |
| NOSH-46 | MRLFGLLLAVRRAGRS LSLMLTLIRGLSKRLG | SEQ ID NO: 46 |
| NOSH-47 | MRLFGLLLAVRRSARS LSLMLTLIRGLSKRLG | SEQ ID NO: 47 |
| NOSH-48 | MRLFGLLLAVRRSGAS LSLMLTLIRGLSKRLG | SEQ ID NO: 48 |
| NOSH-49 | MRLFGLLLAVRRSGRA LSLMLTLIRGLSKRLG | SEQ ID NO: 49 |
| NOSH-50 | MRLFGLLLAVRRSGRS ASLMLTLIRGLSKRLG | SEQ ID NO: 50 |
| NOSH-51 | MRLFGLLLAVRRSGRS LALMLTLIRGLSKRLG | SEQ ID NO: 51 |
| NOSH-52 | MRLFGLLLAVRRSGRS LSAMLTLIRGLSKRLG | SEQ ID NO: 52 |
| NOSH-53 | MRLFGLLLAVRRSGRS LSLALTLIRGLSKRLG | SEQ ID NO: 53 |
| NOSH-54 | MRLFGLLLAVRRSGRS LSLMATLIRGLSKRLG | SEQ ID NO: 54 |
| NOSH-55 | MRLFGLLLAVRRSGRS LSLMLALIRGLSKRLG | SEQ ID NO: 55 |
| NOSH-56 | MRLFGLLLAVRRSGRS LSLMLTAIRGLSKRLG | SEQ ID NO: 56 |
| NOSH-57 | MRLFGLLLAVRRSGRS LSLMLTLARGLSKRLG | SEQ ID NO: 57 |
| NOSH-58 | MRLFGLLLAVRRSGRS LSLMLTLIAGLSKRLG | SEQ ID NO: 58 |
| NOSH-59 | MRLFGLLLAVRRSGRS LSLMLTLIRALSKRLG | SEQ ID NO: 59 |
| NOSH-60 | MRLFGLLLAVRRSGRS LSLMLTLIRGASKRLG | SEQ ID NO: 60 |
| NOSH-61 | MRLFGLLLAVRRSGRS LSLMLTLIRGLAKRLG | SEQ ID NO: 61 |
| NOSH-62 | MRLFGLLLAVRRSGRS LSLMLTLIRGLSARLG | SEQ ID NO: 62 |
| NOSH-63 | MRLFGLLLAVRRSGRS LSLMLTLIRGLSKALG | SEQ ID NO: 63 |
| NOSH-64 | MRLFGLLLAVRRSGRS LSLMLTLIRGLSKRAG | SEQ ID NO: 64 |

TABLE 1-continued

| NOSH Analogs | | |
|---|---|---|
| NOSH-65 | MRLFGLLLAVRRSGRS LSLMLTLIRGLSKRLA | SEQ ID NO: 65 |
| NOSH-66 | RLFGLLLAVGGSGGSL SLMLTLIRGLSK | SEQ ID NO: 66 |
| NOSH-67 | RLFGLLLAVGGLSLML TLIRGLSK | SEQ ID NO: 67 |
| NOSH-68 | RLFGLLLAVGGSGGSG GLSLMLTLIRGLSK | SEQ ID NO: 68 |
| NOSH-69 | MRLFGLLLAVGGSGGS | SEQ ID NO: 69 |
| NOSH-70 | GGSGGSLSLMLTLIRG LSKRLG | SEQ ID NO: 70 |
| NOSH-71 | LLAVGGSGGSLSLMLT L | SEQ ID NO: 71 |
| NOSH-72 | LLLAVGGSGGSLSLML TLIRGLSK | SEQ ID NO: 72 |
| NOSH-73 | MRLFGLLLAVPGSGGS LSLMLTLIRGLSKRLG | SEQ ID NO: 73 |
| NOSH-74 | MRLFGLLLAVPGSGPS LSLMLTLIRGLSKRLG | SEQ ID NO: 74 |
| NOSH-75 | MRLFGLLLAVRRSGGS LSLMLTLIRGLSKRLG | SEQ ID NO: 75 |
| NOSH-76 | LLLAVGGSGGDLDLML TLIRGLDK | SEQ ID NO: 76 |
| NOSH-77 | MPLFGLLLAVRRSGRS LSLMLTLIRGLSKRLG | SEQ ID NO: 77 |
| NOSH-78 | MRPFGLLLAVRRSGRS LSLMLTLIRGLSKRLG | SEQ ID NO: 78 |
| NOSH-79 | MRLPGLLLAVRRSGRS LSLMLTLIRGLSKRLG | SEQ ID NO: 79 |
| NOSH-80 | MRLFPLLLAVRRSGRS LSLMLTLIRGLSKRLG | SEQ ID NO: 80 |
| NOSH-81 | MRLFGPLLAVRRSGRS LSLMLTLIRGLSKRLG | SEQ ID NO: 81 |
| NOSH-82 | MRLFGLPLAVRRSGRS LSLMLTLIRGLSKRLG | SEQ ID NO: 82 |
| NOSH-83 | MRLFGLLPAVRRSGRS LSLMLTLIRGLSKRLG | SEQ ID NO: 83 |
| NOSH-84 | MRLFGLLLPVRRSGRS LSLMLTLIRGLSKRLG | SEQ ID NO: 84 |
| NOSH-85 | MRLFGLLLAPRRSGRS LSLMLTLIRGLSKRLG | SEQ ID NO: 85 |
| NOSH-86 | MRLFGLLLAVPRSGRS LSLMLTLIRGLSKRLG | SEQ ID NO: 86 |
| NOSH-87 | MRLFGLLLAVRPSGRS LSLMLTLIRGLSKRLG | SEQ ID NO: 87 |
| NOSH-88 | MRLFGLLLAVRRPGRS LSLMLTLIRGLSKRLG | SEQ ID NO: 88 |
| NOSH-89 | MRLFGLLLAVRRSPRS LSLMLTLIRGLSKRLG | SEQ ID NO: 89 |
| NOSH-90 | MRLFGLLLAVRRSGPS LSLMLTLIRGLSKRLG | SEQ ID NO: 90 |

TABLE 1-continued

| NOSH Analogs | | |
|---|---|---|
| NOSH-91 | MRLFGLLLAVRRSGRP LSLMLTLIRGLSKRLG | SEQ ID NO: 91 |
| NOSH-92 | MRLFGLLLAVRRSGRS PSLMLTLIRGLSKRLG | SEQ ID NO: 92 |
| NOSH-93 | MRLFGLLLAVRRSGRS LPLMLTLIRGLSKRLG | SEQ ID NO: 93 |
| NOSH-94 | MRLFGLLLAVRRSGRS LSPMLTLIRGLSKRLG | SEQ ID NO: 94 |
| NOSH-95 | MRLFGLLLAVRRSGRS LSLPLTLIRGLSKRLG | SEQ ID NO: 95 |
| NOSH-96 | MRLFGLLLAVRRSGRS LSLMPTLIRGLSKRLG | SEQ ID NO: 96 |
| NOSH-97 | MRLFGLLLAVRRSGRS LSLMLPLIRGLSKRLG | SEQ ID NO: 97 |
| NOSH-98 | MRLFGLLLAVRRSGRS LSLMLTPIRGLSKRLG | SEQ ID NO: 98 |
| NOSH-99 | MRLFGLLLAVRRSGRS LSLMLTLPRGLSKRLG | SEQ ID NO: 99 |
| NOSH-100 | MRLFGLLLAVRRSGRS LSLMLTLIPGLSKRLG | SEQ ID NO: 100 |
| NOSH-101 | MRLFGLLLAVRRSGRS LSLMLTLIRPLSKRLG | SEQ ID NO: 101 |
| NOSH-102 | MRLFGLLLAVRRSGRS LSLMLTLIRGPSKRLG | SEQ ID NO: 102 |
| NOSH-103 | MRLFGLLLAVRRSGRS LSLMLTLIRGLPKRLG | SEQ ID NO: 103 |
| NOSH-104 | MRLFGLLLAVRRSGRS LSLMLTLIRGLSPRLG | SEQ ID NO: 104 |
| NOSH-105 | MRLFGLLLAVRRSGRS LSLMLTLIRGLSKPLG | SEQ ID NO: 105 |
| NOSH-106 | MRLFGLLLAVRRSGRS LSLMLTLIRGLSKRPG | SEQ ID NO: 106 |
| NOSH-107 | MRLFGLLLAVRRSGRS LSLMLTLIRGLSKRLP | SEQ ID NO: 107 |
| NOSH-108 | MRLAALLLAARRSGRS LSLMLTLIRGLSKRLG | SEQ ID NO: 108 |
| NOSH-109 | MRLFALLLAARRSGRS LSLMLTLIRGLSKRLG | SEQ ID NO: 109 |
| NOSH-110 | MRLAGLLLAARRSGRS LSLMLTLIRGLSKRLG | SEQ ID NO: 110 |
| NOSH-111 | MRLAALLLAVRRSGRS LSLMLTLIRGLSKRLG | SEQ ID NO: 111 |
| NOSH-112 | MRLFGLLLAVRRSGRS PSPMPTPIPGPSKPPG | SEQ ID NO: 112 |
| NOSH-113 | MRLFGLLLAVRRSGRS PSLMPTPIPGPSKPPG | SEQ ID NO: 113 |
| NOSH-114 | MRLFGLLLAVRRSGRS PSLMPTLIPGPSKPPG | SEQ ID NO: 114 |
| NOSH-115 | MRLFGLLLAVRRSGRS PSLMPTLIPGLSKPPG | SEQ ID NO: 115 |
| NOSH-116 | MRLFGLLLAVRRSGRS PSLMPTLIPGLSKPLG | SEQ ID NO: 116 |

TABLE 1-continued

| NOSH Analogs | | |
| --- | --- | --- |
| NOSH-117 | MRLFGLLLAVRRSGRS LSLMPTLIPGLSKPLG | SEQ ID NO: 117 |
| NOSH-118 | MRLFGLLLAVRRSGRS LSLMPTLIPGLSKRLG | SEQ ID NO: 118 |
| NOSH-119 | MRLFGLLLAVRRSGRS LSLMLTLIPGLSKRLG | SEQ ID NO: 119 |
| NOSH-120 | MRLAALLLAARRSGRS PSPMPTPIPGPSKPPG | SEQ ID NO: 120 |
| NOSH-121 | MRLAALLLAARRSGRS PSLMPTPIPGPSKPPG | SEQ ID NO: 121 |
| NOSH-122 | MRLAALLLAARRSGRS PSLMPTLIPGPSKPPG | SEQ ID NO: 122 |
| NOSH-123 | MRLAALLLAARRSGRS PSLMPTLIPGLSKPPG | SEQ ID NO: 123 |
| NOSH-124 | MRLAALLLAARRSGRS PSLMPTLIPGLSKPLG | SEQ ID NO: 124 |
| NOSH-125 | MRLAALLLAARRSGRS LSLMPTLIPGLSKPLG | SEQ ID NO: 125 |
| NOSH-126 | MRLAALLLAARRSGRS LSLMPTLIPGLSKRLG | SEQ ID NO: 126 |
| NOSH-127 | MRLAALLLAARRSGRS LSLMLTLIPGLSKRLG | SEQ ID NO: 127 |
| NOSH-128 | MRLFALLLAARRSGRS PSPMPTPIPGPSKPPG | SEQ ID NO: 128 |
| NOSH-129 | MRLFALLLAARRSGRS PSLMPTPIPGPSKPPG | SEQ ID NO: 129 |
| NOSH-130 | MRLFALLLAARRSGRS PSLMPTLIPGPSKPPG | SEQ ID NO: 130 |
| NOSH-131 | MRLFALLLAARRSGRS PSLMPTLIPGLSKPPG | SEQ ID NO: 131 |
| NOSH-132 | MRLFALLLAARRSGRS PSLMPTLIPGLSKPLG | SEQ ID NO: 132 |
| NOSH-133 | MRLFALLLAARRSGRS LSLMPTLIPGLSKPLG | SEQ ID NO: 133 |
| NOSH-134 | MRLFALLLAARRSGRS LSLMPTLIPGLSKRLG | SEQ ID NO: 134 |
| NOSH-135 | MRLFALLLAARRSGRS LSLMLTLIPGLSKRLG | SEQ ID NO: 135 |
| NOSH-136 | MRLAGLLLAARRSGRS PSPMPTPIPGPSKPPG | SEQ ID NO: 136 |
| NOSH-137 | MRLAGLLLAARRSGRS PSLMPTPIPGPSKPPG | SEQ ID NO: 137 |
| NOSH-138 | MRLAGLLLAARRSGRS PSLMPTLIPGPSKPPG | SEQ ID NO: 138 |
| NOSH-139 | MRLAGLLLAARRSGRS PSLMPTLIPGLSKPPG | SEQ ID NO: 139 |
| NOSH-140 | MRLAGLLLAARRSGRS PSLMPTLIPGLSKPLG | SEQ ID NO: 140 |
| NOSH-141 | MRLAGLLLAARRSGRS LSLMPTLIPGLSKPLG | SEQ ID NO: 141 |
| NOSH-142 | MRLAGLLLAARRSGRS LSLMPTLIPGLSKRLG | SEQ ID NO: 142 |

TABLE 1-continued

| NOSH Analogs | | |
| --- | --- | --- |
| NOSH-143 | MRLAGLLLAARRSGRS LSLMLTLIPGLSKRLG | SEQ ID NO: 143 |
| NOSH-144 | MRLAALLLAVRRSGRS PSPMPTPIPGPSKPPG | SEQ ID NO: 144 |
| NOSH-145 | MRLAALLLAVRRSGRS PSLMPTPIPGPSKPPG | SEQ ID NO: 145 |
| NOSH-146 | MRLAALLLAVRRSGRS PSLMPTLIPGPSKPPG | SEQ ID NO: 146 |
| NOSH-147 | MRLAALLLAVRRSGRS PSLMPTLIPGLSKPPG | SEQ ID NO: 147 |
| NOSH-148 | MRLAALLLAVRRSGRS PSLMPTLIPGLSKPLG | SEQ ID NO: 148 |
| NOSH-149 | MRLAALLLAVRRSGRS LSLMPTLIPGLSKPLG | SEQ ID NO: 149 |
| NOSH-150 | MRLAALLLAVRRSGRS LSLMPTLIPGLSKRLG | SEQ ID NO: 150 |
| NOSH-151 | MRLAALLLAVRRSGRS LSLMLTLIPGLSKRLG | SEQ ID NO: 151 |
| NOSH-152 | MPLFGLLLPVPPSGRS LSLMLTLIRGLSKRLG | SEQ ID NO: 152 |
| NOSH-153 | MPLFGLLLPVPRSGRS LSLMLTLIRGLSKRLG | SEQ ID NO: 153 |
| NOSH-154 | MPLFGLLLPVRRSGRS LSLMLTLIRGLSKRLG | SEQ ID NO: 154 |
| NOSH-155 | MRLFGLLLAVRRSGRS LSLMLALIRALSKRLA | SEQ ID NO: 155 |
| NOSH-156 | MRLFGLLLAVRRSGRS LSLMLTLIRALSKRLA | SEQ ID NO: 156 |
| NOSH-157 | MRLFGLLLAVRRSGRS LSLMLALIRALSKRLG | SEQ ID NO: 157 |
| NOSH-158 | MRLFGLLLAVRRSGRS LSLMLALIRGLSKRLA | SEQ ID NO: 158 |
| NOSH-159 | MPLFGLLLPVPPSGRS LSLMLALIRALSKRLA | SEQ ID NO: 159 |
| NOSH-160 | MPLFGLLLPVPPSGRS LSLMLTLIRALSKRLA | SEQ ID NO: 160 |
| NOSH-161 | MPLFGLLLPVPPSGRS LSLMLALIRALSKRLG | SEQ ID NO: 161 |
| NOSH-162 | MPLFGLLLPVPPSGRS LSLMLALIRGLSKRLA | SEQ ID NO: 162 |
| NOSH-163 | MPLFGLLLPVPRSGRS LSLMLALIRALSKRLA | SEQ ID NO: 163 |
| NOSH-164 | MPLFGLLLPVPRSGRS LSLMLTLIRALSKRLA | SEQ ID NO: 164 |
| NOSH-165 | MPLFGLLLPVPRSGRS LSLMLALIRALSKRLG | SEQ ID NO: 165 |
| NOSH-166 | MPLFGLLLPVPRSGRS LSLMLALIRGLSKRLA | SEQ ID NO: 166 |
| NOSH-167 | MPLFGLLLPVRRSGRS LSLMLALIRALSKRLA | SEQ ID NO: 167 |
| NOSH-168 | MPLFGLLLPVRRSGRS LSLMLTLIRALSKRLA | SEQ ID NO: 168 |

TABLE 1-continued

| NOSH Analogs | | |
| --- | --- | --- |
| NOSH-169 | MPLFGLLLPVRRSGRS LSLMLALIRALSKRLG | SEQ ID NO: 169 |
| NOSH-170 | MPLFGLLLPVRRSGRS LSLMLALIRGLSKRLA | SEQ ID NO: 170 |
| NOSH-171 | MPLFGLLLPVPPSGRS PSPMPTPIPGPSKPPG | SEQ ID NO: 171 |
| NOSH-172 | MPLFGLLLPVPPSGRS PSLMPTPIPGPSKPPG | SEQ ID NO: 172 |
| NOSH-173 | MPLFGLLLPVPPSGRS PSLMPTLIPGPSKPPG | SEQ ID NO: 173 |
| NOSH-174 | MPLFGLLLPVPPSGRS PSLMPTLIPGLSKPPG | SEQ ID NO: 174 |
| NOSH-175 | MPLFGLLLPVPPSGRS PSLMPTLIPGLSKPLG | SEQ ID NO: 175 |
| NOSH-176 | MPLFGLLLPVPPSGRS LSLMPTLIPGLSKPLG | SEQ ID NO: 176 |
| NOSH-177 | MPLFGLLLPVPPSGRS LSLMPTLIPGLSKRLG | SEQ ID NO: 177 |
| NOSH-178 | MPLFGLLLPVPPSGRS LSLMLTLIPGLSKRLG | SEQ ID NO: 178 |
| NOSH-179 | MPLFGLLLPVPRSGRS PSPMPTPIPGPSKPPG | SEQ ID NO: 179 |
| NOSH-180 | MPLFGLLLPVPRSGRS PSLMPTPIPGPSKPPG | SEQ ID NO: 180 |
| NOSH-181 | MPLFGLLLPVPRSGRS PSLMPTLIPGPSKPPG | SEQ ID NO: 181 |
| NOSH-182 | MPLFGLLLPVPRSGRS PSLMPTLIPGLSKPPG | SEQ ID NO: 182 |
| NOSH-183 | MPLFGLLLPVPRSGRS PSLMPTLIPGLSKPLG | SEQ ID NO: 183 |
| NOSH-184 | MPLFGLLLPVPRSGRS LSLMPTLIPGLSKPLG | SEQ ID NO: 184 |
| NOSH-185 | MPLFGLLLPVPRSGRS LSLMPTLIPGLSKRLG | SEQ ID NO: 185 |
| NOSH-186 | MPLFGLLLPVPRSGRS LSLMLTLIPGLSKRLG | SEQ ID NO: 186 |
| NOSH-187 | MPLFGLLLPVRRSGRS PSPMPTPIPGPSKPPG | SEQ ID NO: 187 |
| NOSH-188 | MPLFGLLLPVRRSGRS PSLMPTPIPGPSKPPG | SEQ ID NO: 188 |
| NOSH-189 | MPLFGLLLPVRRSGRS PSLMPTLIPGPSKPPG | SEQ ID NO: 189 |
| NOSH-190 | MPLFGLLLPVRRSGRS PSLMPTLIPGLSKPPG | SEQ ID NO: 190 |
| NOSH-191 | MPLFGLLLPVRRSGRS PSLMPTLIPGLSKPLG | SEQ ID NO: 191 |
| NOSH-192 | MPLFGLLLPVRRSGRS LSLMPTLIPGLSKPLG | SEQ ID NO: 192 |
| NOSH-193 | MPLFGLLLPVRRSGRS LSLMPTLIPGLSKRLG | SEQ ID NO: 193 |
| NOSH-194 | MPLFGLLLPVRRSGRS LSLMLTLIPGLSKRLG | SEQ ID NO: 194 |

TABLE 1-continued

| NOSH Analogs | | |
| --- | --- | --- |
| NOSH-195 | MRLAALLLAARRSGRS LSLMLALIRALSKRLA | SEQ ID NO: 195 |
| NOSH-196 | MRLAALLLAARRSGRS LSLMLTLIRALSKRLA | SEQ ID NO: 196 |
| NOSH-197 | MRLAALLLAARRSGRS LSLMLALIRALSKRLG | SEQ ID NO: 197 |
| NOSH-198 | MRLAALLLAARRSGRS LSLMLALIRGLSKRLA | SEQ ID NO: 198 |
| NOSH-199 | MRLFALLLAARRSGRS LSLMLALIRALSKRLA | SEQ ID NO: 199 |
| NOSH-200 | MRLFALLLAARRSGRS LSLMLTLIRALSKRLA | SEQ ID NO: 200 |
| NOSH-201 | MRLFALLLAARRSGRS LSLMLALIRALSKRLG | SEQ ID NO: 201 |
| NOSH-202 | MRLFALLLAARRSGRS LSLMLALIRGLSKRLA | SEQ ID NO: 202 |
| NOSH-203 | MRLAGLLLAARRSGRS LSLMLALIRALSKRLA | SEQ ID NO: 203 |
| NOSH-204 | MRLAGLLLAARRSGRS LSLMLTLIRALSKRLA | SEQ ID NO: 204 |
| NOSH-205 | MRLAGLLLAARRSGRS LSLMLALIRALSKRLG | SEQ ID NO: 205 |
| NOSH-206 | MRLAGLLLAARRSGRS LSLMLALIRGLSKRLA | SEQ ID NO: 206 |
| NOSH-207 | MRLAALLLAVRRSGRS LSLMLALIRALSKRLA | SEQ ID NO: 207 |
| NOSH-208 | MRLAALLLAVRRSGRS LSLMLTLIRALSKRLA | SEQ ID NO: 208 |
| NOSH-209 | MRLAALLLAVRRSGRS LSLMLALIRALSKRLG | SEQ ID NO: 209 |
| NOSH-210 | MRLAALLLAVRRSGRS LSLMLALIRGLSKRLA | SEQ ID NO: 210 |
| NOSH-211 | MRLFGLLLAVRRSGRS LSLMLDLIRGLSKRLG | SEQ ID NO: 211 |
| NOSH-212 | MRLFGLLLAVRRSGRS LSLMLRLIRGLSKRLG | SEQ ID NO: 212 |
| NOSH-213 | MRLFGLLLAVRRSGRS LSLMLWLIRGLSKRLG | SEQ ID NO: 213 |
| NOSH-214 | MRLFGLLLAVRRSGRS LSLMLKLIRGLSKRLG | SEQ ID NO: 214 |

The various methods and techniques described above provide a number of ways to carry out the invention. Of course, it is to be understood that not necessarily all objectives or advantages described may be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as may be taught or suggested herein. A variety of advantageous and disadvantageous alternatives are mentioned herein. It is to be understood that some preferred embodiments specifically include one, another, or several advantageous features, while others specifically exclude one, another, or several disadvantageous features, while still others specifically mitigate a present disadvantageous feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be mixed and matched by one of ordinary skill in this art to perform methods in accordance with principles described herein. Among the various elements, features, and steps some will be specifically included and others specifically excluded in diverse embodiments.

Although the invention has been disclosed in the context of certain embodiments and examples, it will be understood by those skilled in the art that the embodiments of the invention extend beyond the specifically disclosed embodiments to other alternative embodiments and/or uses and modifications and equivalents thereof.

Many variations and alternative elements have been disclosed in embodiments of the present invention. Still further variations and alternate elements will be apparent to one of skill in the art. Among these variations, without limitation, are the compositions and methods related to peptides, mitochondrial peptides, their analogs and derivatives thereof s, methods and compositions related to use of the aforementioned compositions, techniques and composition and use of solutions used therein, and the particular use of the products created through the teachings of the invention. Various embodiments of the invention can specifically include or exclude any of these variations or elements.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

In some embodiments, the terms "a" and "an" and "the" and similar references used in the context of describing a particular embodiment of the invention (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

Preferred embodiments of this invention are described herein, including the best mode known to the inventor for carrying out the invention. Variations on those preferred embodiments will become apparent to those of ordinary skill in the art upon reading the foregoing description. It is contemplated that skilled artisans can employ such variations as appropriate, and the invention can be practiced otherwise than specifically described herein. Accordingly, many embodiments of this invention include all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above cited references and printed publications are herein individually incorporated by reference in their entirety.

In closing, it is to be understood that the embodiments of the invention disclosed herein are illustrative of the principles of the present invention. Other modifications that can be employed can be within the scope of the invention. Thus, by way of example, but not of limitation, alternative configurations of the present invention can be utilized in accordance with the teachings herein. Accordingly, embodiments of the present invention are not limited to that precisely as shown and described.

The invention claimed is:

1. A composition comprising:

a mitochondrial-derived peptide, wherein the mitochondrial-derived peptide comprises an amino acid sequence of any of SEQ ID NOs: 1-214, or wherein the mitochondrial-derived peptide comprises an amino acid sequence with at least 95% sequence identity to any of SEQ ID NOs: 1-215 but is different from SEQ ID NO:215.

2. The composition of claim 1, wherein the mitochondrial-derived peptide comprises an amino acid sequence of LLLAVGGSGGSLSLMLTLIRGLSK (SEQ ID NO: 72).

3. The composition of claim 1, wherein the mitochondrial-derived peptide is about 30-34 amino acids in length.

4. The composition of claim 1, wherein the mitochondrial-derived peptide possesses a post-translational or artificial modification, wherein the artificial modification comprises pegylation, fatty-acid conjugation, polypeptide extension, IgG-Fc, camptothecin (CPT), human serum albumin (HSA), elastin-like polypeptide (ELP), transferrin, or albumin modification.

5. A pharmaceutical composition, comprising a mitochondrial-derived peptide of claim 1 and a pharmaceutically acceptable excipient.

* * * * *

SEQUENCE LISTING

```
<160> NUMBER OF SEQ ID NOS: 215

<210> SEQ ID NO 1
<211> LENGTH: 32
<212> TYPE: PRT
<213> ORGANISM: Artificial Sequence
<220> FEATURE:
<223> OTHER INFORMATION: synthetic construct
```

-continued

<400> SEQUENCE: 1

Met Arg Leu Phe Gly Leu Leu Leu Ala Val Arg Arg Asp Gly Arg Ser
1               5                   10                  15

Leu Ser Leu Met Leu Thr Leu Ile Arg Gly Leu Ser Lys Arg Leu Gly
            20                  25                  30

<210> SEQ ID NO 2
<211> LENGTH: 32
<212> TYPE: PRT
<213> ORGANISM: Artificial Sequence
<220> FEATURE:
<223> OTHER INFORMATION: synthetic construct

<400> SEQUENCE: 2

Met Arg Leu Phe Gly Leu Leu Leu Ala Val Arg Arg Ser Gly Arg Ser
1               5                   10                  15

Leu Ser Leu Met Leu Thr Leu Ile Arg Gly Leu Asp Lys Arg Leu Gly
            20                  25                  30

<210> SEQ ID NO 3
<211> LENGTH: 32
<212> TYPE: PRT
<213> ORGANISM: Artificial Sequence
<220> FEATURE:
<223> OTHER INFORMATION: synthetic construct

<400> SEQUENCE: 3

Met Arg Leu Phe Gly Leu Leu Leu Ala Val Arg Arg Asp Gly Arg Ser
1               5                   10                  15

Leu Ser Leu Met Leu Asp Leu Ile Arg Gly Leu Asp Lys Arg Leu Gly
            20                  25                  30

<210> SEQ ID NO 4
<211> LENGTH: 20
<212> TYPE: PRT
<213> ORGANISM: Artificial Sequence
<220> FEATURE:
<223> OTHER INFORMATION: synthetic construct

<400> SEQUENCE: 4

Gly Leu Leu Leu Ala Val Arg Arg Ser Gly Arg Ser Leu Asp Leu Met
1               5                   10                  15

Leu Thr Leu Ile
            20

<210> SEQ ID NO 5
<211> LENGTH: 16
<212> TYPE: PRT
<213> ORGANISM: Artificial Sequence
<220> FEATURE:
<223> OTHER INFORMATION: synthetic construct

<400> SEQUENCE: 5

Met Arg Leu Phe Gly Leu Leu Leu Ala Val Arg Arg Ser Gly Arg Ser
1               5                   10                  15

<210> SEQ ID NO 6
<211> LENGTH: 16
<212> TYPE: PRT
<213> ORGANISM: Artificial Sequence
<220> FEATURE:
<223> OTHER INFORMATION: synthetic construct

<400> SEQUENCE: 6

Leu Ser Leu Met Leu Thr Leu Ile Arg Gly Leu Ser Lys Arg Leu Gly
1               5                   10                  15

<210> SEQ ID NO 7
<211> LENGTH: 32
<212> TYPE: PRT
<213> ORGANISM: Artificial Sequence
<220> FEATURE:
<223> OTHER INFORMATION: synthetic construct

<400> SEQUENCE: 7

Met Arg Leu Phe Gly Leu Leu Leu Ala Val Gly Gly Ser Gly Arg Ser
1               5                   10                  15

Leu Ser Leu Met Leu Thr Leu Ile Arg Gly Leu Ser Lys Arg Leu Gly
            20                  25                  30

<210> SEQ ID NO 8
<211> LENGTH: 32
<212> TYPE: PRT
<213> ORGANISM: Artificial Sequence
<220> FEATURE:
<223> OTHER INFORMATION: synthetic construct

<400> SEQUENCE: 8

Met Arg Leu Phe Gly Leu Leu Leu Ala Val Gly Gly Ser Gly Gly Ser
1               5                   10                  15

Leu Ser Leu Met Leu Thr Leu Ile Arg Gly Leu Ser Lys Arg Leu Gly
            20                  25                  30

<210> SEQ ID NO 9
<211> LENGTH: 32
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (1)..(1)
<223> OTHER INFORMATION: FORMYLATION

<400> SEQUENCE: 9

Met Arg Leu Phe Gly Leu Leu Leu Ala Val Arg Arg Ser Gly Arg Ser
1               5                   10                  15

Leu Ser Leu Met Leu Thr Leu Ile Arg Gly Leu Ser Lys Arg Leu Gly
            20                  25                  30

<210> SEQ ID NO 10
<211> LENGTH: 32
<212> TYPE: PRT
<213> ORGANISM: Artificial Sequence
<220> FEATURE:
<223> OTHER INFORMATION: synthetic construct

<400> SEQUENCE: 10

Met Arg Leu Phe Gly Leu Leu Leu Ala Val Arg Arg Asp Gly Arg Asp
1               5                   10                  15

Leu Asp Leu Met Leu Asp Leu Ile Arg Gly Leu Asp Lys Arg Leu Gly
            20                  25                  30

<210> SEQ ID NO 11
<211> LENGTH: 32
<212> TYPE: PRT
<213> ORGANISM: Artificial Sequence
<220> FEATURE:
<223> OTHER INFORMATION: synthetic construct

<400> SEQUENCE: 11

```
Met Arg Leu Phe Gly Leu Leu Leu Ala Val Arg Arg Asp Gly Arg Asp
1               5                   10                  15

Leu Asp Leu Met Leu Asp Leu Ile Arg Gly Leu Ser Lys Arg Leu Gly
            20                  25                  30
```

<210> SEQ ID NO 12
<211> LENGTH: 32
<212> TYPE: PRT
<213> ORGANISM: Artificial Sequence
<220> FEATURE:
<223> OTHER INFORMATION: synthetic construct

<400> SEQUENCE: 12

```
Met Arg Leu Phe Gly Leu Leu Leu Ala Val Arg Arg Ser Gly Arg Asp
1               5                   10                  15

Leu Asp Leu Met Leu Asp Leu Ile Arg Gly Leu Asp Lys Arg Leu Gly
            20                  25                  30
```

<210> SEQ ID NO 13
<211> LENGTH: 32
<212> TYPE: PRT
<213> ORGANISM: Artificial Sequence
<220> FEATURE:
<223> OTHER INFORMATION: synthetic construct

<400> SEQUENCE: 13

```
Met Arg Leu Phe Gly Leu Leu Leu Ala Val Arg Arg Asp Gly Arg Ser
1               5                   10                  15

Leu Asp Leu Met Leu Asp Leu Ile Arg Gly Leu Asp Lys Arg Leu Gly
            20                  25                  30
```

<210> SEQ ID NO 14
<211> LENGTH: 32
<212> TYPE: PRT
<213> ORGANISM: Artificial Sequence
<220> FEATURE:
<223> OTHER INFORMATION: synthetic construct

<400> SEQUENCE: 14

```
Met Arg Leu Phe Gly Leu Leu Leu Ala Val Arg Arg Asp Gly Arg Asp
1               5                   10                  15

Leu Ser Leu Met Leu Asp Leu Ile Arg Gly Leu Asp Lys Arg Leu Gly
            20                  25                  30
```

<210> SEQ ID NO 15
<211> LENGTH: 32
<212> TYPE: PRT
<213> ORGANISM: Artificial Sequence
<220> FEATURE:
<223> OTHER INFORMATION: synthetic construct

<400> SEQUENCE: 15

```
Met Arg Leu Phe Gly Leu Leu Leu Ala Val Arg Arg Asp Gly Arg Asp
1               5                   10                  15

Leu Asp Leu Met Leu Thr Leu Ile Arg Gly Leu Asp Lys Arg Leu Gly
            20                  25                  30
```

<210> SEQ ID NO 16
<211> LENGTH: 32
<212> TYPE: PRT
<213> ORGANISM: Artificial Sequence
<220> FEATURE:

-continued

<223> OTHER INFORMATION: synthetic construct

<400> SEQUENCE: 16

Met Arg Leu Phe Gly Leu Leu Leu Ala Val Arg Arg Asp Gly Arg Asp
1               5                   10                  15

Leu Asp Leu Met Leu Thr Leu Ile Arg Gly Leu Ser Lys Arg Leu Gly
            20                  25                  30

<210> SEQ ID NO 17
<211> LENGTH: 32
<212> TYPE: PRT
<213> ORGANISM: Artificial Sequence
<220> FEATURE:
<223> OTHER INFORMATION: synthetic construct

<400> SEQUENCE: 17

Met Arg Leu Phe Gly Leu Leu Leu Ala Val Arg Arg Asp Gly Arg Asp
1               5                   10                  15

Leu Ser Leu Met Leu Asp Leu Ile Arg Gly Leu Ser Lys Arg Leu Gly
            20                  25                  30

<210> SEQ ID NO 18
<211> LENGTH: 32
<212> TYPE: PRT
<213> ORGANISM: Artificial Sequence
<220> FEATURE:
<223> OTHER INFORMATION: synthetic construct

<400> SEQUENCE: 18

Met Arg Leu Phe Gly Leu Leu Leu Ala Val Arg Arg Asp Gly Arg Asp
1               5                   10                  15

Leu Ser Leu Met Leu Thr Leu Ile Arg Gly Leu Asp Lys Arg Leu Gly
            20                  25                  30

<210> SEQ ID NO 19
<211> LENGTH: 32
<212> TYPE: PRT
<213> ORGANISM: Artificial Sequence
<220> FEATURE:
<223> OTHER INFORMATION: synthetic construct

<400> SEQUENCE: 19

Met Arg Leu Phe Gly Leu Leu Leu Ala Val Arg Arg Asp Gly Arg Ser
1               5                   10                  15

Leu Asp Leu Met Leu Asp Leu Ile Arg Gly Leu Ser Lys Arg Leu Gly
            20                  25                  30

<210> SEQ ID NO 20
<211> LENGTH: 32
<212> TYPE: PRT
<213> ORGANISM: Artificial Sequence
<220> FEATURE:
<223> OTHER INFORMATION: synthetic construct

<400> SEQUENCE: 20

Met Arg Leu Phe Gly Leu Leu Leu Ala Val Arg Arg Asp Gly Arg Ser
1               5                   10                  15

Leu Asp Leu Met Leu Thr Leu Ile Arg Gly Leu Asp Lys Arg Leu Gly
            20                  25                  30

<210> SEQ ID NO 21
<211> LENGTH: 32
<212> TYPE: PRT
<213> ORGANISM: Artificial Sequence -continued

```
<220> FEATURE:
<223> OTHER INFORMATION: synthetic construct

<400> SEQUENCE: 21

Met Arg Leu Phe Gly Leu Leu Leu Ala Val Arg Arg Ser Gly Arg Asp
1               5                   10                  15

Leu Asp Leu Met Leu Asp Leu Ile Arg Gly Leu Ser Lys Arg Leu Gly
            20                  25                  30

<210> SEQ ID NO 22
<211> LENGTH: 32
<212> TYPE: PRT
<213> ORGANISM: Artificial Sequence
<220> FEATURE:
<223> OTHER INFORMATION: synthetic construct

<400> SEQUENCE: 22

Met Arg Leu Phe Gly Leu Leu Leu Ala Val Arg Arg Ser Gly Arg Asp
1               5                   10                  15

Leu Asp Leu Met Leu Thr Leu Ile Arg Gly Leu Asp Lys Arg Leu Gly
            20                  25                  30

<210> SEQ ID NO 23
<211> LENGTH: 32
<212> TYPE: PRT
<213> ORGANISM: Artificial Sequence
<220> FEATURE:
<223> OTHER INFORMATION: synthetic construct

<400> SEQUENCE: 23

Met Arg Leu Phe Gly Leu Leu Leu Ala Val Arg Arg Ser Gly Arg Asp
1               5                   10                  15

Leu Ser Leu Met Leu Asp Leu Ile Arg Gly Leu Asp Lys Arg Leu Gly
            20                  25                  30

<210> SEQ ID NO 24
<211> LENGTH: 32
<212> TYPE: PRT
<213> ORGANISM: Artificial Sequence
<220> FEATURE:
<223> OTHER INFORMATION: synthetic construct

<400> SEQUENCE: 24

Met Arg Leu Phe Gly Leu Leu Leu Ala Val Arg Arg Ser Gly Arg Ser
1               5                   10                  15

Leu Asp Leu Met Leu Asp Leu Ile Arg Gly Leu Asp Lys Arg Leu Gly
            20                  25                  30

<210> SEQ ID NO 25
<211> LENGTH: 32
<212> TYPE: PRT
<213> ORGANISM: Artificial Sequence
<220> FEATURE:
<223> OTHER INFORMATION: synthetic construct

<400> SEQUENCE: 25

Met Arg Leu Phe Gly Leu Leu Leu Ala Val Arg Arg Asp Gly Arg Asp
1               5                   10                  15

Leu Ser Leu Met Leu Thr Leu Ile Arg Gly Leu Ser Lys Arg Leu Gly
            20                  25                  30

<210> SEQ ID NO 26
<211> LENGTH: 32
<212> TYPE: PRT
```

<213> ORGANISM: Artificial Sequence
<220> FEATURE:
<223> OTHER INFORMATION: synthetic construct

<400> SEQUENCE: 26

Met Arg Leu Phe Gly Leu Leu Leu Ala Val Arg Arg Asp Gly Arg Ser
1               5                   10                  15

Leu Asp Leu Met Leu Thr Leu Ile Arg Gly Leu Ser Lys Arg Leu Gly
            20                  25                  30

<210> SEQ ID NO 27
<211> LENGTH: 32
<212> TYPE: PRT
<213> ORGANISM: Artificial Sequence
<220> FEATURE:
<223> OTHER INFORMATION: synthetic construct

<400> SEQUENCE: 27

Met Arg Leu Phe Gly Leu Leu Leu Ala Val Arg Arg Asp Gly Arg Ser
1               5                   10                  15

Leu Ser Leu Met Leu Asp Leu Ile Arg Gly Leu Ser Lys Arg Leu Gly
            20                  25                  30

<210> SEQ ID NO 28
<211> LENGTH: 32
<212> TYPE: PRT
<213> ORGANISM: Artificial Sequence
<220> FEATURE:
<223> OTHER INFORMATION: synthetic construct

<400> SEQUENCE: 28

Met Arg Leu Phe Gly Leu Leu Leu Ala Val Arg Arg Asp Gly Arg Ser
1               5                   10                  15

Leu Ser Leu Met Leu Thr Leu Ile Arg Gly Leu Asp Lys Arg Leu Gly
            20                  25                  30

<210> SEQ ID NO 29
<211> LENGTH: 32
<212> TYPE: PRT
<213> ORGANISM: Artificial Sequence
<220> FEATURE:
<223> OTHER INFORMATION: synthetic construct

<400> SEQUENCE: 29

Met Arg Leu Phe Gly Leu Leu Leu Ala Val Arg Arg Ser Gly Arg Asp
1               5                   10                  15

Leu Asp Leu Met Leu Thr Leu Ile Arg Gly Leu Ser Lys Arg Leu Gly
            20                  25                  30

<210> SEQ ID NO 30
<211> LENGTH: 32
<212> TYPE: PRT
<213> ORGANISM: Artificial Sequence
<220> FEATURE:
<223> OTHER INFORMATION: synthetic construct

<400> SEQUENCE: 30

Met Arg Leu Phe Gly Leu Leu Leu Ala Val Arg Arg Ser Gly Arg Asp
1               5                   10                  15

Leu Ser Leu Met Leu Asp Leu Ile Arg Gly Leu Ser Lys Arg Leu Gly
            20                  25                  30

<210> SEQ ID NO 31
<211> LENGTH: 32

<212> TYPE: PRT
<213> ORGANISM: Artificial Sequence
<220> FEATURE:
<223> OTHER INFORMATION: synthetic construct

<400> SEQUENCE: 31

Met Arg Leu Phe Gly Leu Leu Leu Ala Val Arg Arg Ser Gly Arg Asp
1               5                   10                  15

Leu Ser Leu Met Leu Thr Leu Ile Arg Gly Leu Asp Lys Arg Leu Gly
            20                  25                  30

<210> SEQ ID NO 32
<211> LENGTH: 32
<212> TYPE: PRT
<213> ORGANISM: Artificial Sequence
<220> FEATURE:
<223> OTHER INFORMATION: synthetic construct

<400> SEQUENCE: 32

Met Arg Leu Phe Gly Leu Leu Leu Ala Val Arg Arg Ser Gly Arg Ser
1               5                   10                  15

Leu Asp Leu Met Leu Asp Leu Ile Arg Gly Leu Ser Lys Arg Leu Gly
            20                  25                  30

<210> SEQ ID NO 33
<211> LENGTH: 32
<212> TYPE: PRT
<213> ORGANISM: Artificial Sequence
<220> FEATURE:
<223> OTHER INFORMATION: synthetic construct

<400> SEQUENCE: 33

Met Arg Leu Phe Gly Leu Leu Leu Ala Val Arg Arg Ser Gly Arg Ser
1               5                   10                  15

Leu Asp Leu Met Leu Thr Leu Ile Arg Gly Leu Asp Lys Arg Leu Gly
            20                  25                  30

<210> SEQ ID NO 34
<211> LENGTH: 32
<212> TYPE: PRT
<213> ORGANISM: Artificial Sequence
<220> FEATURE:
<223> OTHER INFORMATION: synthetic construct

<400> SEQUENCE: 34

Met Arg Leu Phe Gly Leu Leu Leu Ala Val Arg Arg Ser Gly Arg Ser
1               5                   10                  15

Leu Ser Leu Met Leu Asp Leu Ile Arg Gly Leu Asp Lys Arg Leu Gly
            20                  25                  30

<210> SEQ ID NO 35
<211> LENGTH: 32
<212> TYPE: PRT
<213> ORGANISM: Artificial Sequence
<220> FEATURE:
<223> OTHER INFORMATION: synthetic construct

<400> SEQUENCE: 35

Ala Arg Leu Phe Gly Leu Leu Leu Ala Val Arg Arg Ser Gly Arg Ser
1               5                   10                  15

Leu Ser Leu Met Leu Thr Leu Ile Arg Gly Leu Ser Lys Arg Leu Gly
            20                  25                  30

<210> SEQ ID NO 36

```
<211> LENGTH: 32
<212> TYPE: PRT
<213> ORGANISM: Artificial Sequence
<220> FEATURE:
<223> OTHER INFORMATION: synthetic construct

<400> SEQUENCE: 36

Met Ala Leu Phe Gly Leu Leu Leu Ala Val Arg Arg Ser Gly Arg Ser
1               5                   10                  15

Leu Ser Leu Met Leu Thr Leu Ile Arg Gly Leu Ser Lys Arg Leu Gly
            20                  25                  30

<210> SEQ ID NO 37
<211> LENGTH: 32
<212> TYPE: PRT
<213> ORGANISM: Artificial Sequence
<220> FEATURE:
<223> OTHER INFORMATION: synthetic construct

<400> SEQUENCE: 37

Met Arg Ala Phe Gly Leu Leu Leu Ala Val Arg Arg Ser Gly Arg Ser
1               5                   10                  15

Leu Ser Leu Met Leu Thr Leu Ile Arg Gly Leu Ser Lys Arg Leu Gly
            20                  25                  30

<210> SEQ ID NO 38
<211> LENGTH: 32
<212> TYPE: PRT
<213> ORGANISM: Artificial Sequence
<220> FEATURE:
<223> OTHER INFORMATION: synthetic construct

<400> SEQUENCE: 38

Met Arg Leu Ala Gly Leu Leu Leu Ala Val Arg Arg Ser Gly Arg Ser
1               5                   10                  15

Leu Ser Leu Met Leu Thr Leu Ile Arg Gly Leu Ser Lys Arg Leu Gly
            20                  25                  30

<210> SEQ ID NO 39
<211> LENGTH: 32
<212> TYPE: PRT
<213> ORGANISM: Artificial Sequence
<220> FEATURE:
<223> OTHER INFORMATION: synthetic construct

<400> SEQUENCE: 39

Met Arg Leu Phe Ala Leu Leu Leu Ala Val Arg Arg Ser Gly Arg Ser
1               5                   10                  15

Leu Ser Leu Met Leu Thr Leu Ile Arg Gly Leu Ser Lys Arg Leu Gly
            20                  25                  30

<210> SEQ ID NO 40
<211> LENGTH: 32
<212> TYPE: PRT
<213> ORGANISM: Artificial Sequence
<220> FEATURE:
<223> OTHER INFORMATION: synthetic construct

<400> SEQUENCE: 40

Met Arg Leu Phe Gly Ala Leu Leu Ala Val Arg Arg Ser Gly Arg Ser
1               5                   10                  15

Leu Ser Leu Met Leu Thr Leu Ile Arg Gly Leu Ser Lys Arg Leu Gly
            20                  25                  30
```

```
<210> SEQ ID NO 41
<211> LENGTH: 32
<212> TYPE: PRT
<213> ORGANISM: Artificial Sequence
<220> FEATURE:
<223> OTHER INFORMATION: synthetic construct

<400> SEQUENCE: 41

Met Arg Leu Phe Gly Leu Ala Leu Ala Val Arg Arg Ser Gly Arg Ser
1               5                   10                  15

Leu Ser Leu Met Leu Thr Leu Ile Arg Gly Leu Ser Lys Arg Leu Gly
            20                  25                  30

<210> SEQ ID NO 42
<211> LENGTH: 32
<212> TYPE: PRT
<213> ORGANISM: Artificial Sequence
<220> FEATURE:
<223> OTHER INFORMATION: synthetic construct

<400> SEQUENCE: 42

Met Arg Leu Phe Gly Leu Leu Ala Ala Val Arg Arg Ser Gly Arg Ser
1               5                   10                  15

Leu Ser Leu Met Leu Thr Leu Ile Arg Gly Leu Ser Lys Arg Leu Gly
            20                  25                  30

<210> SEQ ID NO 43
<211> LENGTH: 32
<212> TYPE: PRT
<213> ORGANISM: Artificial Sequence
<220> FEATURE:
<223> OTHER INFORMATION: synthetic construct

<400> SEQUENCE: 43

Met Arg Leu Phe Gly Leu Leu Leu Ala Ala Arg Arg Ser Gly Arg Ser
1               5                   10                  15

Leu Ser Leu Met Leu Thr Leu Ile Arg Gly Leu Ser Lys Arg Leu Gly
            20                  25                  30

<210> SEQ ID NO 44
<211> LENGTH: 32
<212> TYPE: PRT
<213> ORGANISM: Artificial Sequence
<220> FEATURE:
<223> OTHER INFORMATION: synthetic construct

<400> SEQUENCE: 44

Met Arg Leu Phe Gly Leu Leu Leu Ala Val Ala Arg Ser Gly Arg Ser
1               5                   10                  15

Leu Ser Leu Met Leu Thr Leu Ile Arg Gly Leu Ser Lys Arg Leu Gly
            20                  25                  30

<210> SEQ ID NO 45
<211> LENGTH: 32
<212> TYPE: PRT
<213> ORGANISM: Artificial Sequence
<220> FEATURE:
<223> OTHER INFORMATION: synthetic construct

<400> SEQUENCE: 45

Met Arg Leu Phe Gly Leu Leu Leu Ala Val Arg Ala Ser Gly Arg Ser
1               5                   10                  15

Leu Ser Leu Met Leu Thr Leu Ile Arg Gly Leu Ser Lys Arg Leu Gly
            20                  25                  30
```

-continued

```
<210> SEQ ID NO 46
<211> LENGTH: 32
<212> TYPE: PRT
<213> ORGANISM: Artificial Sequence
<220> FEATURE:
<223> OTHER INFORMATION: synthetic construct

<400> SEQUENCE: 46

Met Arg Leu Phe Gly Leu Leu Leu Ala Val Arg Arg Ala Gly Arg Ser
1               5                   10                  15

Leu Ser Leu Met Leu Thr Leu Ile Arg Gly Leu Ser Lys Arg Leu Gly
            20                  25                  30

<210> SEQ ID NO 47
<211> LENGTH: 32
<212> TYPE: PRT
<213> ORGANISM: Artificial Sequence
<220> FEATURE:
<223> OTHER INFORMATION: synthetic construct

<400> SEQUENCE: 47

Met Arg Leu Phe Gly Leu Leu Leu Ala Val Arg Arg Ser Ala Arg Ser
1               5                   10                  15

Leu Ser Leu Met Leu Thr Leu Ile Arg Gly Leu Ser Lys Arg Leu Gly
            20                  25                  30

<210> SEQ ID NO 48
<211> LENGTH: 32
<212> TYPE: PRT
<213> ORGANISM: Artificial Sequence
<220> FEATURE:
<223> OTHER INFORMATION: synthetic construct

<400> SEQUENCE: 48

Met Arg Leu Phe Gly Leu Leu Leu Ala Val Arg Arg Ser Gly Ala Ser
1               5                   10                  15

Leu Ser Leu Met Leu Thr Leu Ile Arg Gly Leu Ser Lys Arg Leu Gly
            20                  25                  30

<210> SEQ ID NO 49
<211> LENGTH: 32
<212> TYPE: PRT
<213> ORGANISM: Artificial Sequence
<220> FEATURE:
<223> OTHER INFORMATION: synthetic construct

<400> SEQUENCE: 49

Met Arg Leu Phe Gly Leu Leu Leu Ala Val Arg Arg Ser Gly Arg Ala
1               5                   10                  15

Leu Ser Leu Met Leu Thr Leu Ile Arg Gly Leu Ser Lys Arg Leu Gly
            20                  25                  30

<210> SEQ ID NO 50
<211> LENGTH: 32
<212> TYPE: PRT
<213> ORGANISM: Artificial Sequence
<220> FEATURE:
<223> OTHER INFORMATION: synthetic construct

<400> SEQUENCE: 50

Met Arg Leu Phe Gly Leu Leu Leu Ala Val Arg Arg Ser Gly Arg Ser
1               5                   10                  15

Ala Ser Leu Met Leu Thr Leu Ile Arg Gly Leu Ser Lys Arg Leu Gly
            20                  25                  30
```

```
<210> SEQ ID NO 51
<211> LENGTH: 32
<212> TYPE: PRT
<213> ORGANISM: Artificial Sequence
<220> FEATURE:
<223> OTHER INFORMATION: synthetic construct

<400> SEQUENCE: 51

Met Arg Leu Phe Gly Leu Leu Leu Ala Val Arg Arg Ser Gly Arg Ser
1               5                   10                  15

Leu Ala Leu Met Leu Thr Leu Ile Arg Gly Leu Ser Lys Arg Leu Gly
            20                  25                  30

<210> SEQ ID NO 52
<211> LENGTH: 32
<212> TYPE: PRT
<213> ORGANISM: Artificial Sequence
<220> FEATURE:
<223> OTHER INFORMATION: synthetic construct

<400> SEQUENCE: 52

Met Arg Leu Phe Gly Leu Leu Leu Ala Val Arg Arg Ser Gly Arg Ser
1               5                   10                  15

Leu Ser Ala Met Leu Thr Leu Ile Arg Gly Leu Ser Lys Arg Leu Gly
            20                  25                  30

<210> SEQ ID NO 53
<211> LENGTH: 32
<212> TYPE: PRT
<213> ORGANISM: Artificial Sequence
<220> FEATURE:
<223> OTHER INFORMATION: synthetic construct

<400> SEQUENCE: 53

Met Arg Leu Phe Gly Leu Leu Leu Ala Val Arg Arg Ser Gly Arg Ser
1               5                   10                  15

Leu Ser Leu Ala Leu Thr Leu Ile Arg Gly Leu Ser Lys Arg Leu Gly
            20                  25                  30

<210> SEQ ID NO 54
<211> LENGTH: 32
<212> TYPE: PRT
<213> ORGANISM: Artificial Sequence
<220> FEATURE:
<223> OTHER INFORMATION: synthetic construct

<400> SEQUENCE: 54

Met Arg Leu Phe Gly Leu Leu Leu Ala Val Arg Arg Ser Gly Arg Ser
1               5                   10                  15

Leu Ser Leu Met Ala Thr Leu Ile Arg Gly Leu Ser Lys Arg Leu Gly
            20                  25                  30

<210> SEQ ID NO 55
<211> LENGTH: 32
<212> TYPE: PRT
<213> ORGANISM: Artificial Sequence
<220> FEATURE:
<223> OTHER INFORMATION: synthetic construct

<400> SEQUENCE: 55

Met Arg Leu Phe Gly Leu Leu Leu Ala Val Arg Arg Ser Gly Arg Ser
1               5                   10                  15

Leu Ser Leu Met Leu Ala Leu Ile Arg Gly Leu Ser Lys Arg Leu Gly
```

-continued

```
              20              25              30

<210> SEQ ID NO 56
<211> LENGTH: 32
<212> TYPE: PRT
<213> ORGANISM: Artificial Sequence
<220> FEATURE:
<223> OTHER INFORMATION: synthetic construct

<400> SEQUENCE: 56

Met Arg Leu Phe Gly Leu Leu Leu Ala Val Arg Arg Ser Gly Arg Ser
1               5                   10                  15

Leu Ser Leu Met Leu Thr Ala Ile Arg Gly Leu Ser Lys Arg Leu Gly
            20              25              30

<210> SEQ ID NO 57
<211> LENGTH: 32
<212> TYPE: PRT
<213> ORGANISM: Artificial Sequence
<220> FEATURE:
<223> OTHER INFORMATION: synthetic construct

<400> SEQUENCE: 57

Met Arg Leu Phe Gly Leu Leu Leu Ala Val Arg Arg Ser Gly Arg Ser
1               5                   10                  15

Leu Ser Leu Met Leu Thr Leu Ala Arg Gly Leu Ser Lys Arg Leu Gly
            20              25              30

<210> SEQ ID NO 58
<211> LENGTH: 32
<212> TYPE: PRT
<213> ORGANISM: Artificial Sequence
<220> FEATURE:
<223> OTHER INFORMATION: synthetic construct

<400> SEQUENCE: 58

Met Arg Leu Phe Gly Leu Leu Leu Ala Val Arg Arg Ser Gly Arg Ser
1               5                   10                  15

Leu Ser Leu Met Leu Thr Leu Ile Ala Gly Leu Ser Lys Arg Leu Gly
            20              25              30

<210> SEQ ID NO 59
<211> LENGTH: 32
<212> TYPE: PRT
<213> ORGANISM: Artificial Sequence
<220> FEATURE:
<223> OTHER INFORMATION: synthetic construct

<400> SEQUENCE: 59

Met Arg Leu Phe Gly Leu Leu Leu Ala Val Arg Arg Ser Gly Arg Ser
1               5                   10                  15

Leu Ser Leu Met Leu Thr Leu Ile Arg Ala Leu Ser Lys Arg Leu Gly
            20              25              30

<210> SEQ ID NO 60
<211> LENGTH: 32
<212> TYPE: PRT
<213> ORGANISM: Artificial Sequence
<220> FEATURE:
<223> OTHER INFORMATION: synthetic construct

<400> SEQUENCE: 60

Met Arg Leu Phe Gly Leu Leu Leu Ala Val Arg Arg Ser Gly Arg Ser
1               5                   10                  15
```

```
Leu Ser Leu Met Leu Thr Leu Ile Arg Gly Ala Ser Lys Arg Leu Gly
            20                  25                  30

<210> SEQ ID NO 61
<211> LENGTH: 32
<212> TYPE: PRT
<213> ORGANISM: Artificial Sequence
<220> FEATURE:
<223> OTHER INFORMATION: synthetic construct

<400> SEQUENCE: 61

Met Arg Leu Phe Gly Leu Leu Leu Ala Val Arg Arg Ser Gly Arg Ser
1               5                   10                  15

Leu Ser Leu Met Leu Thr Leu Ile Arg Gly Leu Ala Lys Arg Leu Gly
            20                  25                  30

<210> SEQ ID NO 62
<211> LENGTH: 32
<212> TYPE: PRT
<213> ORGANISM: Artificial Sequence
<220> FEATURE:
<223> OTHER INFORMATION: synthetic construct

<400> SEQUENCE: 62

Met Arg Leu Phe Gly Leu Leu Leu Ala Val Arg Arg Ser Gly Arg Ser
1               5                   10                  15

Leu Ser Leu Met Leu Thr Leu Ile Arg Gly Leu Ser Ala Arg Leu Gly
            20                  25                  30

<210> SEQ ID NO 63
<211> LENGTH: 32
<212> TYPE: PRT
<213> ORGANISM: Artificial Sequence
<220> FEATURE:
<223> OTHER INFORMATION: synthetic construct

<400> SEQUENCE: 63

Met Arg Leu Phe Gly Leu Leu Leu Ala Val Arg Arg Ser Gly Arg Ser
1               5                   10                  15

Leu Ser Leu Met Leu Thr Leu Ile Arg Gly Leu Ser Lys Ala Leu Gly
            20                  25                  30

<210> SEQ ID NO 64
<211> LENGTH: 32
<212> TYPE: PRT
<213> ORGANISM: Artificial Sequence
<220> FEATURE:
<223> OTHER INFORMATION: synthetic construct

<400> SEQUENCE: 64

Met Arg Leu Phe Gly Leu Leu Leu Ala Val Arg Arg Ser Gly Arg Ser
1               5                   10                  15

Leu Ser Leu Met Leu Thr Leu Ile Arg Gly Leu Ser Lys Arg Ala Gly
            20                  25                  30

<210> SEQ ID NO 65
<211> LENGTH: 32
<212> TYPE: PRT
<213> ORGANISM: Artificial Sequence
<220> FEATURE:
<223> OTHER INFORMATION: synthetic construct

<400> SEQUENCE: 65

Met Arg Leu Phe Gly Leu Leu Leu Ala Val Arg Arg Ser Gly Arg Ser
1               5                   10                  15
```

Leu Ser Leu Met Leu Thr Leu Ile Arg Gly Leu Ser Lys Arg Leu Ala
                20                  25                  30

<210> SEQ ID NO 66
<211> LENGTH: 28
<212> TYPE: PRT
<213> ORGANISM: Artificial Sequence
<220> FEATURE:
<223> OTHER INFORMATION: synthetic construct

<400> SEQUENCE: 66

Arg Leu Phe Gly Leu Leu Leu Ala Val Gly Gly Ser Gly Gly Ser Leu
1               5                   10                  15

Ser Leu Met Leu Thr Leu Ile Arg Gly Leu Ser Lys
            20                  25

<210> SEQ ID NO 67
<211> LENGTH: 24
<212> TYPE: PRT
<213> ORGANISM: Artificial Sequence
<220> FEATURE:
<223> OTHER INFORMATION: synthetic construct

<400> SEQUENCE: 67

Arg Leu Phe Gly Leu Leu Leu Ala Val Gly Gly Leu Ser Leu Met Leu
1               5                   10                  15

Thr Leu Ile Arg Gly Leu Ser Lys
            20

<210> SEQ ID NO 68
<211> LENGTH: 30
<212> TYPE: PRT
<213> ORGANISM: Artificial Sequence
<220> FEATURE:
<223> OTHER INFORMATION: synthetic construct

<400> SEQUENCE: 68

Arg Leu Phe Gly Leu Leu Leu Ala Val Gly Gly Ser Gly Gly Ser Gly
1               5                   10                  15

Gly Leu Ser Leu Met Leu Thr Leu Ile Arg Gly Leu Ser Lys
            20                  25                  30

<210> SEQ ID NO 69
<211> LENGTH: 16
<212> TYPE: PRT
<213> ORGANISM: Artificial Sequence
<220> FEATURE:
<223> OTHER INFORMATION: synthetic construct

<400> SEQUENCE: 69

Met Arg Leu Phe Gly Leu Leu Leu Ala Val Gly Gly Ser Gly Gly Ser
1               5                   10                  15

<210> SEQ ID NO 70
<211> LENGTH: 22
<212> TYPE: PRT
<213> ORGANISM: Artificial Sequence
<220> FEATURE:
<223> OTHER INFORMATION: synthetic construct

<400> SEQUENCE: 70

Gly Gly Ser Gly Gly Ser Leu Ser Leu Met Leu Thr Leu Ile Arg Gly
1               5                   10                  15

Leu Ser Lys Arg Leu Gly

```
         20

<210> SEQ ID NO 71
<211> LENGTH: 17
<212> TYPE: PRT
<213> ORGANISM: Artificial Sequence
<220> FEATURE:
<223> OTHER INFORMATION: synthetic construct

<400> SEQUENCE: 71

Leu Leu Ala Val Gly Gly Ser Gly Gly Ser Leu Ser Leu Met Leu Thr
1               5                   10                  15

Leu

<210> SEQ ID NO 72
<211> LENGTH: 24
<212> TYPE: PRT
<213> ORGANISM: Artificial Sequence
<220> FEATURE:
<223> OTHER INFORMATION: synthetic construct

<400> SEQUENCE: 72

Leu Leu Leu Ala Val Gly Gly Ser Gly Gly Ser Leu Ser Leu Met Leu
1               5                   10                  15

Thr Leu Ile Arg Gly Leu Ser Lys
            20

<210> SEQ ID NO 73
<211> LENGTH: 32
<212> TYPE: PRT
<213> ORGANISM: Artificial Sequence
<220> FEATURE:
<223> OTHER INFORMATION: synthetic construct

<400> SEQUENCE: 73

Met Arg Leu Phe Gly Leu Leu Leu Ala Val Pro Gly Ser Gly Gly Ser
1               5                   10                  15

Leu Ser Leu Met Leu Thr Leu Ile Arg Gly Leu Ser Lys Arg Leu Gly
            20                  25                  30

<210> SEQ ID NO 74
<211> LENGTH: 32
<212> TYPE: PRT
<213> ORGANISM: Artificial Sequence
<220> FEATURE:
<223> OTHER INFORMATION: synthetic construct

<400> SEQUENCE: 74

Met Arg Leu Phe Gly Leu Leu Leu Ala Val Pro Gly Ser Gly Pro Ser
1               5                   10                  15

Leu Ser Leu Met Leu Thr Leu Ile Arg Gly Leu Ser Lys Arg Leu Gly
            20                  25                  30

<210> SEQ ID NO 75
<211> LENGTH: 32
<212> TYPE: PRT
<213> ORGANISM: Artificial Sequence
<220> FEATURE:
<223> OTHER INFORMATION: synthetic construct

<400> SEQUENCE: 75

Met Arg Leu Phe Gly Leu Leu Leu Ala Val Arg Arg Ser Gly Gly Ser
1               5                   10                  15

Leu Ser Leu Met Leu Thr Leu Ile Arg Gly Leu Ser Lys Arg Leu Gly
```

-continued

```
                    20              25              30

<210> SEQ ID NO 76
<211> LENGTH: 24
<212> TYPE: PRT
<213> ORGANISM: Artificial Sequence
<220> FEATURE:
<223> OTHER INFORMATION: synthetic construct

<400> SEQUENCE: 76

Leu Leu Leu Ala Val Gly Gly Ser Gly Gly Asp Leu Asp Leu Met Leu
1               5                   10                  15

Thr Leu Ile Arg Gly Leu Asp Lys
            20

<210> SEQ ID NO 77
<211> LENGTH: 32
<212> TYPE: PRT
<213> ORGANISM: Artificial Sequence
<220> FEATURE:
<223> OTHER INFORMATION: synthetic construct

<400> SEQUENCE: 77

Met Pro Leu Phe Gly Leu Leu Leu Ala Val Arg Arg Ser Gly Arg Ser
1               5                   10                  15

Leu Ser Leu Met Leu Thr Leu Ile Arg Gly Leu Ser Lys Arg Leu Gly
            20              25              30

<210> SEQ ID NO 78
<211> LENGTH: 32
<212> TYPE: PRT
<213> ORGANISM: Artificial Sequence
<220> FEATURE:
<223> OTHER INFORMATION: synthetic construct

<400> SEQUENCE: 78

Met Arg Pro Phe Gly Leu Leu Leu Ala Val Arg Arg Ser Gly Arg Ser
1               5                   10                  15

Leu Ser Leu Met Leu Thr Leu Ile Arg Gly Leu Ser Lys Arg Leu Gly
            20              25              30

<210> SEQ ID NO 79
<211> LENGTH: 32
<212> TYPE: PRT
<213> ORGANISM: Artificial Sequence
<220> FEATURE:
<223> OTHER INFORMATION: synthetic construct

<400> SEQUENCE: 79

Met Arg Leu Pro Gly Leu Leu Leu Ala Val Arg Arg Ser Gly Arg Ser
1               5                   10                  15

Leu Ser Leu Met Leu Thr Leu Ile Arg Gly Leu Ser Lys Arg Leu Gly
            20              25              30

<210> SEQ ID NO 80
<211> LENGTH: 32
<212> TYPE: PRT
<213> ORGANISM: Artificial Sequence
<220> FEATURE:
<223> OTHER INFORMATION: synthetic construct

<400> SEQUENCE: 80

Met Arg Leu Phe Pro Leu Leu Leu Ala Val Arg Arg Ser Gly Arg Ser
1               5                   10                  15
```

-continued

```
Leu Ser Leu Met Leu Thr Leu Ile Arg Gly Leu Ser Lys Arg Leu Gly
            20                  25                  30

<210> SEQ ID NO 81
<211> LENGTH: 32
<212> TYPE: PRT
<213> ORGANISM: Artificial Sequence
<220> FEATURE:
<223> OTHER INFORMATION: synthetic construct

<400> SEQUENCE: 81

Met Arg Leu Phe Gly Pro Leu Leu Ala Val Arg Arg Ser Gly Arg Ser
1               5                   10                  15

Leu Ser Leu Met Leu Thr Leu Ile Arg Gly Leu Ser Lys Arg Leu Gly
            20                  25                  30

<210> SEQ ID NO 82
<211> LENGTH: 32
<212> TYPE: PRT
<213> ORGANISM: Artificial Sequence
<220> FEATURE:
<223> OTHER INFORMATION: synthetic construct

<400> SEQUENCE: 82

Met Arg Leu Phe Gly Leu Pro Leu Ala Val Arg Arg Ser Gly Arg Ser
1               5                   10                  15

Leu Ser Leu Met Leu Thr Leu Ile Arg Gly Leu Ser Lys Arg Leu Gly
            20                  25                  30

<210> SEQ ID NO 83
<211> LENGTH: 32
<212> TYPE: PRT
<213> ORGANISM: Artificial Sequence
<220> FEATURE:
<223> OTHER INFORMATION: synthetic construct

<400> SEQUENCE: 83

Met Arg Leu Phe Gly Leu Leu Pro Ala Val Arg Arg Ser Gly Arg Ser
1               5                   10                  15

Leu Ser Leu Met Leu Thr Leu Ile Arg Gly Leu Ser Lys Arg Leu Gly
            20                  25                  30

<210> SEQ ID NO 84
<211> LENGTH: 32
<212> TYPE: PRT
<213> ORGANISM: Artificial Sequence
<220> FEATURE:
<223> OTHER INFORMATION: synthetic construct

<400> SEQUENCE: 84

Met Arg Leu Phe Gly Leu Leu Leu Pro Val Arg Arg Ser Gly Arg Ser
1               5                   10                  15

Leu Ser Leu Met Leu Thr Leu Ile Arg Gly Leu Ser Lys Arg Leu Gly
            20                  25                  30

<210> SEQ ID NO 85
<211> LENGTH: 32
<212> TYPE: PRT
<213> ORGANISM: Artificial Sequence
<220> FEATURE:
<223> OTHER INFORMATION: synthetic construct

<400> SEQUENCE: 85

Met Arg Leu Phe Gly Leu Leu Leu Ala Pro Arg Arg Ser Gly Arg Ser
1               5                   10                  15
```

```
Leu Ser Leu Met Leu Thr Leu Ile Arg Gly Leu Ser Lys Arg Leu Gly
        20                  25                  30

<210> SEQ ID NO 86
<211> LENGTH: 32
<212> TYPE: PRT
<213> ORGANISM: Artificial Sequence
<220> FEATURE:
<223> OTHER INFORMATION: synthetic construct

<400> SEQUENCE: 86

Met Arg Leu Phe Gly Leu Leu Leu Ala Val Pro Arg Ser Gly Arg Ser
1               5                   10                  15

Leu Ser Leu Met Leu Thr Leu Ile Arg Gly Leu Ser Lys Arg Leu Gly
        20                  25                  30

<210> SEQ ID NO 87
<211> LENGTH: 32
<212> TYPE: PRT
<213> ORGANISM: Artificial Sequence
<220> FEATURE:
<223> OTHER INFORMATION: synthetic construct

<400> SEQUENCE: 87

Met Arg Leu Phe Gly Leu Leu Leu Ala Val Arg Pro Ser Gly Arg Ser
1               5                   10                  15

Leu Ser Leu Met Leu Thr Leu Ile Arg Gly Leu Ser Lys Arg Leu Gly
        20                  25                  30

<210> SEQ ID NO 88
<211> LENGTH: 32
<212> TYPE: PRT
<213> ORGANISM: Artificial Sequence
<220> FEATURE:
<223> OTHER INFORMATION: synthetic construct

<400> SEQUENCE: 88

Met Arg Leu Phe Gly Leu Leu Leu Ala Val Arg Arg Pro Gly Arg Ser
1               5                   10                  15

Leu Ser Leu Met Leu Thr Leu Ile Arg Gly Leu Ser Lys Arg Leu Gly
        20                  25                  30

<210> SEQ ID NO 89
<211> LENGTH: 32
<212> TYPE: PRT
<213> ORGANISM: Artificial Sequence
<220> FEATURE:
<223> OTHER INFORMATION: synthetic construct

<400> SEQUENCE: 89

Met Arg Leu Phe Gly Leu Leu Leu Ala Val Arg Arg Ser Pro Arg Ser
1               5                   10                  15

Leu Ser Leu Met Leu Thr Leu Ile Arg Gly Leu Ser Lys Arg Leu Gly
        20                  25                  30

<210> SEQ ID NO 90
<211> LENGTH: 32
<212> TYPE: PRT
<213> ORGANISM: Artificial Sequence
<220> FEATURE:
<223> OTHER INFORMATION: synthetic construct

<400> SEQUENCE: 90

Met Arg Leu Phe Gly Leu Leu Leu Ala Val Arg Arg Ser Gly Pro Ser
```

-continued

```
1               5               10              15

Leu Ser Leu Met Leu Thr Leu Ile Arg Gly Leu Ser Lys Arg Leu Gly
            20              25              30

<210> SEQ ID NO 91
<211> LENGTH: 32
<212> TYPE: PRT
<213> ORGANISM: Artificial Sequence
<220> FEATURE:
<223> OTHER INFORMATION: synthetic construct

<400> SEQUENCE: 91

Met Arg Leu Phe Gly Leu Leu Leu Ala Val Arg Arg Ser Gly Arg Pro
1               5               10              15

Leu Ser Leu Met Leu Thr Leu Ile Arg Gly Leu Ser Lys Arg Leu Gly
            20              25              30

<210> SEQ ID NO 92
<211> LENGTH: 32
<212> TYPE: PRT
<213> ORGANISM: Artificial Sequence
<220> FEATURE:
<223> OTHER INFORMATION: synthetic construct

<400> SEQUENCE: 92

Met Arg Leu Phe Gly Leu Leu Leu Ala Val Arg Arg Ser Gly Arg Ser
1               5               10              15

Pro Ser Leu Met Leu Thr Leu Ile Arg Gly Leu Ser Lys Arg Leu Gly
            20              25              30

<210> SEQ ID NO 93
<211> LENGTH: 32
<212> TYPE: PRT
<213> ORGANISM: Artificial Sequence
<220> FEATURE:
<223> OTHER INFORMATION: synthetic construct

<400> SEQUENCE: 93

Met Arg Leu Phe Gly Leu Leu Leu Ala Val Arg Arg Ser Gly Arg Ser
1               5               10              15

Leu Pro Leu Met Leu Thr Leu Ile Arg Gly Leu Ser Lys Arg Leu Gly
            20              25              30

<210> SEQ ID NO 94
<211> LENGTH: 32
<212> TYPE: PRT
<213> ORGANISM: Artificial Sequence
<220> FEATURE:
<223> OTHER INFORMATION: synthetic construct

<400> SEQUENCE: 94

Met Arg Leu Phe Gly Leu Leu Leu Ala Val Arg Arg Ser Gly Arg Ser
1               5               10              15

Leu Ser Pro Met Leu Thr Leu Ile Arg Gly Leu Ser Lys Arg Leu Gly
            20              25              30

<210> SEQ ID NO 95
<211> LENGTH: 32
<212> TYPE: PRT
<213> ORGANISM: Artificial Sequence
<220> FEATURE:
<223> OTHER INFORMATION: synthetic construct

<400> SEQUENCE: 95
```

```
Met Arg Leu Phe Gly Leu Leu Leu Ala Val Arg Arg Ser Gly Arg Ser
1               5                   10                  15

Leu Ser Leu Pro Leu Thr Leu Ile Arg Gly Leu Ser Lys Arg Leu Gly
            20                  25                  30

<210> SEQ ID NO 96
<211> LENGTH: 32
<212> TYPE: PRT
<213> ORGANISM: Artificial Sequence
<220> FEATURE:
<223> OTHER INFORMATION: synthetic construct

<400> SEQUENCE: 96

Met Arg Leu Phe Gly Leu Leu Leu Ala Val Arg Arg Ser Gly Arg Ser
1               5                   10                  15

Leu Ser Leu Met Pro Thr Leu Ile Arg Gly Leu Ser Lys Arg Leu Gly
            20                  25                  30

<210> SEQ ID NO 97
<211> LENGTH: 32
<212> TYPE: PRT
<213> ORGANISM: Artificial Sequence
<220> FEATURE:
<223> OTHER INFORMATION: synthetic construct

<400> SEQUENCE: 97

Met Arg Leu Phe Gly Leu Leu Leu Ala Val Arg Arg Ser Gly Arg Ser
1               5                   10                  15

Leu Ser Leu Met Leu Pro Leu Ile Arg Gly Leu Ser Lys Arg Leu Gly
            20                  25                  30

<210> SEQ ID NO 98
<211> LENGTH: 32
<212> TYPE: PRT
<213> ORGANISM: Artificial Sequence
<220> FEATURE:
<223> OTHER INFORMATION: synthetic construct

<400> SEQUENCE: 98

Met Arg Leu Phe Gly Leu Leu Leu Ala Val Arg Arg Ser Gly Arg Ser
1               5                   10                  15

Leu Ser Leu Met Leu Thr Pro Ile Arg Gly Leu Ser Lys Arg Leu Gly
            20                  25                  30

<210> SEQ ID NO 99
<211> LENGTH: 32
<212> TYPE: PRT
<213> ORGANISM: Artificial Sequence
<220> FEATURE:
<223> OTHER INFORMATION: synthetic construct

<400> SEQUENCE: 99

Met Arg Leu Phe Gly Leu Leu Leu Ala Val Arg Arg Ser Gly Arg Ser
1               5                   10                  15

Leu Ser Leu Met Leu Thr Leu Pro Arg Gly Leu Ser Lys Arg Leu Gly
            20                  25                  30

<210> SEQ ID NO 100
<211> LENGTH: 32
<212> TYPE: PRT
<213> ORGANISM: Artificial Sequence
<220> FEATURE:
<223> OTHER INFORMATION: synthetic construct

<400> SEQUENCE: 100
```

-continued

```
Met Arg Leu Phe Gly Leu Leu Leu Ala Val Arg Arg Ser Gly Arg Ser
1               5                   10                  15

Leu Ser Leu Met Leu Thr Leu Ile Pro Gly Leu Ser Lys Arg Leu Gly
            20                  25                  30
```

<210> SEQ ID NO 101
<211> LENGTH: 32
<212> TYPE: PRT
<213> ORGANISM: Artificial Sequence
<220> FEATURE:
<223> OTHER INFORMATION: synthetic construct

<400> SEQUENCE: 101

```
Met Arg Leu Phe Gly Leu Leu Leu Ala Val Arg Arg Ser Gly Arg Ser
1               5                   10                  15

Leu Ser Leu Met Leu Thr Leu Ile Arg Pro Leu Ser Lys Arg Leu Gly
            20                  25                  30
```

<210> SEQ ID NO 102
<211> LENGTH: 32
<212> TYPE: PRT
<213> ORGANISM: Artificial Sequence
<220> FEATURE:
<223> OTHER INFORMATION: synthetic construct

<400> SEQUENCE: 102

```
Met Arg Leu Phe Gly Leu Leu Leu Ala Val Arg Arg Ser Gly Arg Ser
1               5                   10                  15

Leu Ser Leu Met Leu Thr Leu Ile Arg Gly Pro Ser Lys Arg Leu Gly
            20                  25                  30
```

<210> SEQ ID NO 103
<211> LENGTH: 32
<212> TYPE: PRT
<213> ORGANISM: Artificial Sequence
<220> FEATURE:
<223> OTHER INFORMATION: synthetic construct

<400> SEQUENCE: 103

```
Met Arg Leu Phe Gly Leu Leu Leu Ala Val Arg Arg Ser Gly Arg Ser
1               5                   10                  15

Leu Ser Leu Met Leu Thr Leu Ile Arg Gly Leu Pro Lys Arg Leu Gly
            20                  25                  30
```

<210> SEQ ID NO 104
<211> LENGTH: 32
<212> TYPE: PRT
<213> ORGANISM: Artificial Sequence
<220> FEATURE:
<223> OTHER INFORMATION: synthetic construct

<400> SEQUENCE: 104

```
Met Arg Leu Phe Gly Leu Leu Leu Ala Val Arg Arg Ser Gly Arg Ser
1               5                   10                  15

Leu Ser Leu Met Leu Thr Leu Ile Arg Gly Leu Ser Pro Arg Leu Gly
            20                  25                  30
```

<210> SEQ ID NO 105
<211> LENGTH: 32
<212> TYPE: PRT
<213> ORGANISM: Artificial Sequence
<220> FEATURE:
<223> OTHER INFORMATION: synthetic construct -continued

```
<400> SEQUENCE: 105

Met Arg Leu Phe Gly Leu Leu Leu Ala Val Arg Arg Ser Gly Arg Ser
1               5                   10                  15

Leu Ser Leu Met Leu Thr Leu Ile Arg Gly Leu Ser Lys Pro Leu Gly
            20                  25                  30

<210> SEQ ID NO 106
<211> LENGTH: 32
<212> TYPE: PRT
<213> ORGANISM: Artificial Sequence
<220> FEATURE:
<223> OTHER INFORMATION: synthetic construct

<400> SEQUENCE: 106

Met Arg Leu Phe Gly Leu Leu Leu Ala Val Arg Arg Ser Gly Arg Ser
1               5                   10                  15

Leu Ser Leu Met Leu Thr Leu Ile Arg Gly Leu Ser Lys Arg Pro Gly
            20                  25                  30

<210> SEQ ID NO 107
<211> LENGTH: 32
<212> TYPE: PRT
<213> ORGANISM: Artificial Sequence
<220> FEATURE:
<223> OTHER INFORMATION: synthetic construct

<400> SEQUENCE: 107

Met Arg Leu Phe Gly Leu Leu Leu Ala Val Arg Arg Ser Gly Arg Ser
1               5                   10                  15

Leu Ser Leu Met Leu Thr Leu Ile Arg Gly Leu Ser Lys Arg Leu Pro
            20                  25                  30

<210> SEQ ID NO 108
<211> LENGTH: 32
<212> TYPE: PRT
<213> ORGANISM: Artificial Sequence
<220> FEATURE:
<223> OTHER INFORMATION: synthetic construct

<400> SEQUENCE: 108

Met Arg Leu Ala Ala Leu Leu Leu Ala Ala Arg Arg Ser Gly Arg Ser
1               5                   10                  15

Leu Ser Leu Met Leu Thr Leu Ile Arg Gly Leu Ser Lys Arg Leu Gly
            20                  25                  30

<210> SEQ ID NO 109
<211> LENGTH: 32
<212> TYPE: PRT
<213> ORGANISM: Artificial Sequence
<220> FEATURE:
<223> OTHER INFORMATION: synthetic construct

<400> SEQUENCE: 109

Met Arg Leu Phe Ala Leu Leu Leu Ala Ala Arg Arg Ser Gly Arg Ser
1               5                   10                  15

Leu Ser Leu Met Leu Thr Leu Ile Arg Gly Leu Ser Lys Arg Leu Gly
            20                  25                  30

<210> SEQ ID NO 110
<211> LENGTH: 32
<212> TYPE: PRT
<213> ORGANISM: Artificial Sequence
<220> FEATURE:
<223> OTHER INFORMATION: synthetic construct
```

-continued

```
<400> SEQUENCE: 110

Met Arg Leu Ala Gly Leu Leu Leu Ala Ala Arg Arg Ser Gly Arg Ser
1               5                   10                  15

Leu Ser Leu Met Leu Thr Leu Ile Arg Gly Leu Ser Lys Arg Leu Gly
            20                  25                  30

<210> SEQ ID NO 111
<211> LENGTH: 32
<212> TYPE: PRT
<213> ORGANISM: Artificial Sequence
<220> FEATURE:
<223> OTHER INFORMATION: synthetic construct

<400> SEQUENCE: 111

Met Arg Leu Ala Ala Leu Leu Leu Ala Val Arg Arg Ser Gly Arg Ser
1               5                   10                  15

Leu Ser Leu Met Leu Thr Leu Ile Arg Gly Leu Ser Lys Arg Leu Gly
            20                  25                  30

<210> SEQ ID NO 112
<211> LENGTH: 32
<212> TYPE: PRT
<213> ORGANISM: Artificial Sequence
<220> FEATURE:
<223> OTHER INFORMATION: synthetic construct

<400> SEQUENCE: 112

Met Arg Leu Phe Gly Leu Leu Leu Ala Val Arg Arg Ser Gly Arg Ser
1               5                   10                  15

Pro Ser Pro Met Pro Thr Pro Ile Pro Gly Pro Ser Lys Pro Pro Gly
            20                  25                  30

<210> SEQ ID NO 113
<211> LENGTH: 32
<212> TYPE: PRT
<213> ORGANISM: Artificial Sequence
<220> FEATURE:
<223> OTHER INFORMATION: synthetic construct

<400> SEQUENCE: 113

Met Arg Leu Phe Gly Leu Leu Leu Ala Val Arg Arg Ser Gly Arg Ser
1               5                   10                  15

Pro Ser Leu Met Pro Thr Pro Ile Pro Gly Pro Ser Lys Pro Pro Gly
            20                  25                  30

<210> SEQ ID NO 114
<211> LENGTH: 32
<212> TYPE: PRT
<213> ORGANISM: Artificial Sequence
<220> FEATURE:
<223> OTHER INFORMATION: synthetic construct

<400> SEQUENCE: 114

Met Arg Leu Phe Gly Leu Leu Leu Ala Val Arg Arg Ser Gly Arg Ser
1               5                   10                  15

Pro Ser Leu Met Pro Thr Leu Ile Pro Gly Pro Ser Lys Pro Pro Gly
            20                  25                  30

<210> SEQ ID NO 115
<211> LENGTH: 32
<212> TYPE: PRT
<213> ORGANISM: Artificial Sequence
<220> FEATURE:
```

```
<223> OTHER INFORMATION: synthetic construct

<400> SEQUENCE: 115

Met Arg Leu Phe Gly Leu Leu Leu Ala Val Arg Arg Ser Gly Arg Ser
1               5                   10                  15

Pro Ser Leu Met Pro Thr Leu Ile Pro Gly Leu Ser Lys Pro Pro Gly
            20                  25                  30

<210> SEQ ID NO 116
<211> LENGTH: 32
<212> TYPE: PRT
<213> ORGANISM: Artificial Sequence
<220> FEATURE:
<223> OTHER INFORMATION: synthetic construct

<400> SEQUENCE: 116

Met Arg Leu Phe Gly Leu Leu Leu Ala Val Arg Arg Ser Gly Arg Ser
1               5                   10                  15

Pro Ser Leu Met Pro Thr Leu Ile Pro Gly Leu Ser Lys Pro Leu Gly
            20                  25                  30

<210> SEQ ID NO 117
<211> LENGTH: 32
<212> TYPE: PRT
<213> ORGANISM: Artificial Sequence
<220> FEATURE:
<223> OTHER INFORMATION: synthetic construct

<400> SEQUENCE: 117

Met Arg Leu Phe Gly Leu Leu Leu Ala Val Arg Arg Ser Gly Arg Ser
1               5                   10                  15

Leu Ser Leu Met Pro Thr Leu Ile Pro Gly Leu Ser Lys Pro Leu Gly
            20                  25                  30

<210> SEQ ID NO 118
<211> LENGTH: 32
<212> TYPE: PRT
<213> ORGANISM: Artificial Sequence
<220> FEATURE:
<223> OTHER INFORMATION: synthetic construct

<400> SEQUENCE: 118

Met Arg Leu Phe Gly Leu Leu Leu Ala Val Arg Arg Ser Gly Arg Ser
1               5                   10                  15

Leu Ser Leu Met Pro Thr Leu Ile Pro Gly Leu Ser Lys Arg Leu Gly
            20                  25                  30

<210> SEQ ID NO 119
<211> LENGTH: 32
<212> TYPE: PRT
<213> ORGANISM: Artificial Sequence
<220> FEATURE:
<223> OTHER INFORMATION: synthetic construct

<400> SEQUENCE: 119

Met Arg Leu Phe Gly Leu Leu Leu Ala Val Arg Arg Ser Gly Arg Ser
1               5                   10                  15

Leu Ser Leu Met Leu Thr Leu Ile Pro Gly Leu Ser Lys Arg Leu Gly
            20                  25                  30

<210> SEQ ID NO 120
<211> LENGTH: 32
<212> TYPE: PRT
<213> ORGANISM: Artificial Sequence
```

```
<220> FEATURE:
<223> OTHER INFORMATION: synthetic construct

<400> SEQUENCE: 120

Met Arg Leu Ala Ala Leu Leu Leu Ala Ala Arg Arg Ser Gly Arg Ser
1               5                   10                  15

Pro Ser Pro Met Pro Thr Pro Ile Pro Gly Pro Ser Lys Pro Pro Gly
            20                  25                  30

<210> SEQ ID NO 121
<211> LENGTH: 32
<212> TYPE: PRT
<213> ORGANISM: Artificial Sequence
<220> FEATURE:
<223> OTHER INFORMATION: synthetic construct

<400> SEQUENCE: 121

Met Arg Leu Ala Ala Leu Leu Leu Ala Ala Arg Arg Ser Gly Arg Ser
1               5                   10                  15

Pro Ser Leu Met Pro Thr Pro Ile Pro Gly Pro Ser Lys Pro Pro Gly
            20                  25                  30

<210> SEQ ID NO 122
<211> LENGTH: 32
<212> TYPE: PRT
<213> ORGANISM: Artificial Sequence
<220> FEATURE:
<223> OTHER INFORMATION: synthetic construct

<400> SEQUENCE: 122

Met Arg Leu Ala Ala Leu Leu Leu Ala Ala Arg Arg Ser Gly Arg Ser
1               5                   10                  15

Pro Ser Leu Met Pro Thr Leu Ile Pro Gly Pro Ser Lys Pro Pro Gly
            20                  25                  30

<210> SEQ ID NO 123
<211> LENGTH: 32
<212> TYPE: PRT
<213> ORGANISM: Artificial Sequence
<220> FEATURE:
<223> OTHER INFORMATION: synthetic construct

<400> SEQUENCE: 123

Met Arg Leu Ala Ala Leu Leu Leu Ala Ala Arg Arg Ser Gly Arg Ser
1               5                   10                  15

Pro Ser Leu Met Pro Thr Leu Ile Pro Gly Leu Ser Lys Pro Pro Gly
            20                  25                  30

<210> SEQ ID NO 124
<211> LENGTH: 32
<212> TYPE: PRT
<213> ORGANISM: Artificial Sequence
<220> FEATURE:
<223> OTHER INFORMATION: synthetic construct

<400> SEQUENCE: 124

Met Arg Leu Ala Ala Leu Leu Leu Ala Ala Arg Arg Ser Gly Arg Ser
1               5                   10                  15

Pro Ser Leu Met Pro Thr Leu Ile Pro Gly Leu Ser Lys Pro Leu Gly
            20                  25                  30

<210> SEQ ID NO 125
<211> LENGTH: 32
<212> TYPE: PRT
```

-continued

```
<213> ORGANISM: Artificial Sequence
<220> FEATURE:
<223> OTHER INFORMATION: synthetic construct

<400> SEQUENCE: 125

Met Arg Leu Ala Ala Leu Leu Leu Ala Ala Arg Arg Ser Gly Arg Ser
1               5                   10                  15

Leu Ser Leu Met Pro Thr Leu Ile Pro Gly Leu Ser Lys Pro Leu Gly
            20                  25                  30

<210> SEQ ID NO 126
<211> LENGTH: 32
<212> TYPE: PRT
<213> ORGANISM: Artificial Sequence
<220> FEATURE:
<223> OTHER INFORMATION: synthetic construct

<400> SEQUENCE: 126

Met Arg Leu Ala Ala Leu Leu Leu Ala Ala Arg Arg Ser Gly Arg Ser
1               5                   10                  15

Leu Ser Leu Met Pro Thr Leu Ile Pro Gly Leu Ser Lys Arg Leu Gly
            20                  25                  30

<210> SEQ ID NO 127
<211> LENGTH: 32
<212> TYPE: PRT
<213> ORGANISM: Artificial Sequence
<220> FEATURE:
<223> OTHER INFORMATION: synthetic construct

<400> SEQUENCE: 127

Met Arg Leu Ala Ala Leu Leu Leu Ala Ala Arg Arg Ser Gly Arg Ser
1               5                   10                  15

Leu Ser Leu Met Leu Thr Leu Ile Pro Gly Leu Ser Lys Arg Leu Gly
            20                  25                  30

<210> SEQ ID NO 128
<211> LENGTH: 32
<212> TYPE: PRT
<213> ORGANISM: Artificial Sequence
<220> FEATURE:
<223> OTHER INFORMATION: synthetic construct

<400> SEQUENCE: 128

Met Arg Leu Phe Ala Leu Leu Leu Ala Ala Arg Arg Ser Gly Arg Ser
1               5                   10                  15

Pro Ser Pro Met Pro Thr Pro Ile Pro Gly Pro Ser Lys Pro Pro Gly
            20                  25                  30

<210> SEQ ID NO 129
<211> LENGTH: 32
<212> TYPE: PRT
<213> ORGANISM: Artificial Sequence
<220> FEATURE:
<223> OTHER INFORMATION: synthetic construct

<400> SEQUENCE: 129

Met Arg Leu Phe Ala Leu Leu Leu Ala Ala Arg Arg Ser Gly Arg Ser
1               5                   10                  15

Pro Ser Leu Met Pro Thr Pro Ile Pro Gly Pro Ser Lys Pro Pro Gly
            20                  25                  30

<210> SEQ ID NO 130
<211> LENGTH: 32
```

```
<212> TYPE: PRT
<213> ORGANISM: Artificial Sequence
<220> FEATURE:
<223> OTHER INFORMATION: synthetic construct

<400> SEQUENCE: 130

Met Arg Leu Phe Ala Leu Leu Leu Ala Ala Arg Arg Ser Gly Arg Ser
1               5                   10                  15

Pro Ser Leu Met Pro Thr Leu Ile Pro Gly Pro Ser Lys Pro Pro Gly
            20                  25                  30

<210> SEQ ID NO 131
<211> LENGTH: 32
<212> TYPE: PRT
<213> ORGANISM: Artificial Sequence
<220> FEATURE:
<223> OTHER INFORMATION: synthetic construct

<400> SEQUENCE: 131

Met Arg Leu Phe Ala Leu Leu Leu Ala Ala Arg Arg Ser Gly Arg Ser
1               5                   10                  15

Pro Ser Leu Met Pro Thr Leu Ile Pro Gly Leu Ser Lys Pro Pro Gly
            20                  25                  30

<210> SEQ ID NO 132
<211> LENGTH: 32
<212> TYPE: PRT
<213> ORGANISM: Artificial Sequence
<220> FEATURE:
<223> OTHER INFORMATION: synthetic construct

<400> SEQUENCE: 132

Met Arg Leu Phe Ala Leu Leu Leu Ala Ala Arg Arg Ser Gly Arg Ser
1               5                   10                  15

Pro Ser Leu Met Pro Thr Leu Ile Pro Gly Leu Ser Lys Pro Leu Gly
            20                  25                  30

<210> SEQ ID NO 133
<211> LENGTH: 32
<212> TYPE: PRT
<213> ORGANISM: Artificial Sequence
<220> FEATURE:
<223> OTHER INFORMATION: synthetic construct

<400> SEQUENCE: 133

Met Arg Leu Phe Ala Leu Leu Leu Ala Ala Arg Arg Ser Gly Arg Ser
1               5                   10                  15

Leu Ser Leu Met Pro Thr Leu Ile Pro Gly Leu Ser Lys Pro Leu Gly
            20                  25                  30

<210> SEQ ID NO 134
<211> LENGTH: 32
<212> TYPE: PRT
<213> ORGANISM: Artificial Sequence
<220> FEATURE:
<223> OTHER INFORMATION: synthetic construct

<400> SEQUENCE: 134

Met Arg Leu Phe Ala Leu Leu Leu Ala Ala Arg Arg Ser Gly Arg Ser
1               5                   10                  15

Leu Ser Leu Met Pro Thr Leu Ile Pro Gly Leu Ser Lys Arg Leu Gly
            20                  25                  30

<210> SEQ ID NO 135
```

<211> LENGTH: 32
<212> TYPE: PRT
<213> ORGANISM: Artificial Sequence
<220> FEATURE:
<223> OTHER INFORMATION: synthetic construct

<400> SEQUENCE: 135

Met Arg Leu Phe Ala Leu Leu Leu Ala Ala Arg Arg Ser Gly Arg Ser
1               5                   10                  15

Leu Ser Leu Met Leu Thr Leu Ile Pro Gly Leu Ser Lys Arg Leu Gly
            20                  25                  30

<210> SEQ ID NO 136
<211> LENGTH: 32
<212> TYPE: PRT
<213> ORGANISM: Artificial Sequence
<220> FEATURE:
<223> OTHER INFORMATION: synthetic construct

<400> SEQUENCE: 136

Met Arg Leu Ala Gly Leu Leu Leu Ala Ala Arg Arg Ser Gly Arg Ser
1               5                   10                  15

Pro Ser Pro Met Pro Thr Pro Ile Pro Gly Pro Ser Lys Pro Pro Gly
            20                  25                  30

<210> SEQ ID NO 137
<211> LENGTH: 32
<212> TYPE: PRT
<213> ORGANISM: Artificial Sequence
<220> FEATURE:
<223> OTHER INFORMATION: synthetic construct

<400> SEQUENCE: 137

Met Arg Leu Ala Gly Leu Leu Leu Ala Ala Arg Arg Ser Gly Arg Ser
1               5                   10                  15

Pro Ser Leu Met Pro Thr Pro Ile Pro Gly Pro Ser Lys Pro Pro Gly
            20                  25                  30

<210> SEQ ID NO 138
<211> LENGTH: 32
<212> TYPE: PRT
<213> ORGANISM: Artificial Sequence
<220> FEATURE:
<223> OTHER INFORMATION: synthetic construct

<400> SEQUENCE: 138

Met Arg Leu Ala Gly Leu Leu Leu Ala Ala Arg Arg Ser Gly Arg Ser
1               5                   10                  15

Pro Ser Leu Met Pro Thr Leu Ile Pro Gly Pro Ser Lys Pro Pro Gly
            20                  25                  30

<210> SEQ ID NO 139
<211> LENGTH: 32
<212> TYPE: PRT
<213> ORGANISM: Artificial Sequence
<220> FEATURE:
<223> OTHER INFORMATION: synthetic construct

<400> SEQUENCE: 139

Met Arg Leu Ala Gly Leu Leu Leu Ala Ala Arg Arg Ser Gly Arg Ser
1               5                   10                  15

Pro Ser Leu Met Pro Thr Leu Ile Pro Gly Leu Ser Lys Pro Pro Gly
            20                  25                  30

```
<210> SEQ ID NO 140
<211> LENGTH: 32
<212> TYPE: PRT
<213> ORGANISM: Artificial Sequence
<220> FEATURE:
<223> OTHER INFORMATION: synthetic construct

<400> SEQUENCE: 140

Met Arg Leu Ala Gly Leu Leu Leu Ala Ala Arg Arg Ser Gly Arg Ser
1               5                   10                  15

Pro Ser Leu Met Pro Thr Leu Ile Pro Gly Leu Ser Lys Pro Leu Gly
            20                  25                  30

<210> SEQ ID NO 141
<211> LENGTH: 32
<212> TYPE: PRT
<213> ORGANISM: Artificial Sequence
<220> FEATURE:
<223> OTHER INFORMATION: synthetic construct

<400> SEQUENCE: 141

Met Arg Leu Ala Gly Leu Leu Leu Ala Ala Arg Arg Ser Gly Arg Ser
1               5                   10                  15

Leu Ser Leu Met Pro Thr Leu Ile Pro Gly Leu Ser Lys Pro Leu Gly
            20                  25                  30

<210> SEQ ID NO 142
<211> LENGTH: 32
<212> TYPE: PRT
<213> ORGANISM: Artificial Sequence
<220> FEATURE:
<223> OTHER INFORMATION: synthetic construct

<400> SEQUENCE: 142

Met Arg Leu Ala Gly Leu Leu Leu Ala Ala Arg Arg Ser Gly Arg Ser
1               5                   10                  15

Leu Ser Leu Met Pro Thr Leu Ile Pro Gly Leu Ser Lys Arg Leu Gly
            20                  25                  30

<210> SEQ ID NO 143
<211> LENGTH: 32
<212> TYPE: PRT
<213> ORGANISM: Artificial Sequence
<220> FEATURE:
<223> OTHER INFORMATION: synthetic construct

<400> SEQUENCE: 143

Met Arg Leu Ala Gly Leu Leu Leu Ala Ala Arg Arg Ser Gly Arg Ser
1               5                   10                  15

Leu Ser Leu Met Leu Thr Leu Ile Pro Gly Leu Ser Lys Arg Leu Gly
            20                  25                  30

<210> SEQ ID NO 144
<211> LENGTH: 32
<212> TYPE: PRT
<213> ORGANISM: Artificial Sequence
<220> FEATURE:
<223> OTHER INFORMATION: synthetic construct

<400> SEQUENCE: 144

Met Arg Leu Ala Ala Leu Leu Leu Ala Val Arg Arg Ser Gly Arg Ser
1               5                   10                  15

Pro Ser Pro Met Pro Thr Pro Ile Pro Gly Pro Ser Lys Pro Pro Gly
            20                  25                  30
```

-continued

```
<210> SEQ ID NO 145
<211> LENGTH: 32
<212> TYPE: PRT
<213> ORGANISM: Artificial Sequence
<220> FEATURE:
<223> OTHER INFORMATION: synthetic construct

<400> SEQUENCE: 145

Met Arg Leu Ala Ala Leu Leu Leu Ala Val Arg Arg Ser Gly Arg Ser
1               5                   10                  15

Pro Ser Leu Met Pro Thr Pro Ile Pro Gly Pro Ser Lys Pro Pro Gly
            20                  25                  30

<210> SEQ ID NO 146
<211> LENGTH: 32
<212> TYPE: PRT
<213> ORGANISM: Artificial Sequence
<220> FEATURE:
<223> OTHER INFORMATION: synthetic construct

<400> SEQUENCE: 146

Met Arg Leu Ala Ala Leu Leu Leu Ala Val Arg Arg Ser Gly Arg Ser
1               5                   10                  15

Pro Ser Leu Met Pro Thr Leu Ile Pro Gly Pro Ser Lys Pro Pro Gly
            20                  25                  30

<210> SEQ ID NO 147
<211> LENGTH: 32
<212> TYPE: PRT
<213> ORGANISM: Artificial Sequence
<220> FEATURE:
<223> OTHER INFORMATION: synthetic construct

<400> SEQUENCE: 147

Met Arg Leu Ala Ala Leu Leu Leu Ala Val Arg Arg Ser Gly Arg Ser
1               5                   10                  15

Pro Ser Leu Met Pro Thr Leu Ile Pro Gly Leu Ser Lys Pro Pro Gly
            20                  25                  30

<210> SEQ ID NO 148
<211> LENGTH: 32
<212> TYPE: PRT
<213> ORGANISM: Artificial Sequence
<220> FEATURE:
<223> OTHER INFORMATION: synthetic construct

<400> SEQUENCE: 148

Met Arg Leu Ala Ala Leu Leu Leu Ala Val Arg Arg Ser Gly Arg Ser
1               5                   10                  15

Pro Ser Leu Met Pro Thr Leu Ile Pro Gly Leu Ser Lys Pro Leu Gly
            20                  25                  30

<210> SEQ ID NO 149
<211> LENGTH: 32
<212> TYPE: PRT
<213> ORGANISM: Artificial Sequence
<220> FEATURE:
<223> OTHER INFORMATION: synthetic construct

<400> SEQUENCE: 149

Met Arg Leu Ala Ala Leu Leu Leu Ala Val Arg Arg Ser Gly Arg Ser
1               5                   10                  15

Leu Ser Leu Met Pro Thr Leu Ile Pro Gly Leu Ser Lys Pro Leu Gly
            20                  25                  30
```

```
<210> SEQ ID NO 150
<211> LENGTH: 32
<212> TYPE: PRT
<213> ORGANISM: Artificial Sequence
<220> FEATURE:
<223> OTHER INFORMATION: synthetic construct

<400> SEQUENCE: 150

Met Arg Leu Ala Ala Leu Leu Leu Ala Val Arg Arg Ser Gly Arg Ser
1               5                   10                  15

Leu Ser Leu Met Pro Thr Leu Ile Pro Gly Leu Ser Lys Arg Leu Gly
            20                  25                  30

<210> SEQ ID NO 151
<211> LENGTH: 32
<212> TYPE: PRT
<213> ORGANISM: Artificial Sequence
<220> FEATURE:
<223> OTHER INFORMATION: synthetic construct

<400> SEQUENCE: 151

Met Arg Leu Ala Ala Leu Leu Leu Ala Val Arg Arg Ser Gly Arg Ser
1               5                   10                  15

Leu Ser Leu Met Leu Thr Leu Ile Pro Gly Leu Ser Lys Arg Leu Gly
            20                  25                  30

<210> SEQ ID NO 152
<211> LENGTH: 32
<212> TYPE: PRT
<213> ORGANISM: Artificial Sequence
<220> FEATURE:
<223> OTHER INFORMATION: synthetic construct

<400> SEQUENCE: 152

Met Pro Leu Phe Gly Leu Leu Leu Pro Val Pro Pro Ser Gly Arg Ser
1               5                   10                  15

Leu Ser Leu Met Leu Thr Leu Ile Arg Gly Leu Ser Lys Arg Leu Gly
            20                  25                  30

<210> SEQ ID NO 153
<211> LENGTH: 32
<212> TYPE: PRT
<213> ORGANISM: Artificial Sequence
<220> FEATURE:
<223> OTHER INFORMATION: synthetic construct

<400> SEQUENCE: 153

Met Pro Leu Phe Gly Leu Leu Leu Pro Val Pro Arg Ser Gly Arg Ser
1               5                   10                  15

Leu Ser Leu Met Leu Thr Leu Ile Arg Gly Leu Ser Lys Arg Leu Gly
            20                  25                  30

<210> SEQ ID NO 154
<211> LENGTH: 32
<212> TYPE: PRT
<213> ORGANISM: Artificial Sequence
<220> FEATURE:
<223> OTHER INFORMATION: synthetic construct

<400> SEQUENCE: 154

Met Pro Leu Phe Gly Leu Leu Leu Pro Val Arg Arg Ser Gly Arg Ser
1               5                   10                  15

Leu Ser Leu Met Leu Thr Leu Ile Arg Gly Leu Ser Lys Arg Leu Gly
```

```
                 20              25              30

<210> SEQ ID NO 155
<211> LENGTH: 32
<212> TYPE: PRT
<213> ORGANISM: Artificial Sequence
<220> FEATURE:
<223> OTHER INFORMATION: synthetic construct

<400> SEQUENCE: 155

Met Arg Leu Phe Gly Leu Leu Leu Ala Val Arg Arg Ser Gly Arg Ser
1               5                   10                  15

Leu Ser Leu Met Leu Ala Leu Ile Arg Ala Leu Ser Lys Arg Leu Ala
            20                  25                  30

<210> SEQ ID NO 156
<211> LENGTH: 32
<212> TYPE: PRT
<213> ORGANISM: Artificial Sequence
<220> FEATURE:
<223> OTHER INFORMATION: synthetic construct

<400> SEQUENCE: 156

Met Arg Leu Phe Gly Leu Leu Leu Ala Val Arg Arg Ser Gly Arg Ser
1               5                   10                  15

Leu Ser Leu Met Leu Thr Leu Ile Arg Ala Leu Ser Lys Arg Leu Ala
            20                  25                  30

<210> SEQ ID NO 157
<211> LENGTH: 32
<212> TYPE: PRT
<213> ORGANISM: Artificial Sequence
<220> FEATURE:
<223> OTHER INFORMATION: synthetic construct

<400> SEQUENCE: 157

Met Arg Leu Phe Gly Leu Leu Leu Ala Val Arg Arg Ser Gly Arg Ser
1               5                   10                  15

Leu Ser Leu Met Leu Ala Leu Ile Arg Ala Leu Ser Lys Arg Leu Gly
            20                  25                  30

<210> SEQ ID NO 158
<211> LENGTH: 32
<212> TYPE: PRT
<213> ORGANISM: Artificial Sequence
<220> FEATURE:
<223> OTHER INFORMATION: synthetic construct

<400> SEQUENCE: 158

Met Arg Leu Phe Gly Leu Leu Leu Ala Val Arg Arg Ser Gly Arg Ser
1               5                   10                  15

Leu Ser Leu Met Leu Ala Leu Ile Arg Gly Leu Ser Lys Arg Leu Ala
            20                  25                  30

<210> SEQ ID NO 159
<211> LENGTH: 32
<212> TYPE: PRT
<213> ORGANISM: Artificial Sequence
<220> FEATURE:
<223> OTHER INFORMATION: synthetic construct

<400> SEQUENCE: 159

Met Pro Leu Phe Gly Leu Leu Leu Pro Val Pro Pro Ser Gly Arg Ser
1               5                   10                  15
```

-continued

---

Leu Ser Leu Met Leu Ala Leu Ile Arg Ala Leu Ser Lys Arg Leu Ala
            20                  25                  30

<210> SEQ ID NO 160
<211> LENGTH: 32
<212> TYPE: PRT
<213> ORGANISM: Artificial Sequence
<220> FEATURE:
<223> OTHER INFORMATION: synthetic construct

<400> SEQUENCE: 160

Met Pro Leu Phe Gly Leu Leu Leu Pro Val Pro Pro Ser Gly Arg Ser
1               5                   10                  15

Leu Ser Leu Met Leu Thr Leu Ile Arg Ala Leu Ser Lys Arg Leu Ala
            20                  25                  30

<210> SEQ ID NO 161
<211> LENGTH: 32
<212> TYPE: PRT
<213> ORGANISM: Artificial Sequence
<220> FEATURE:
<223> OTHER INFORMATION: synthetic construct

<400> SEQUENCE: 161

Met Pro Leu Phe Gly Leu Leu Leu Pro Val Pro Pro Ser Gly Arg Ser
1               5                   10                  15

Leu Ser Leu Met Leu Ala Leu Ile Arg Ala Leu Ser Lys Arg Leu Gly
            20                  25                  30

<210> SEQ ID NO 162
<211> LENGTH: 32
<212> TYPE: PRT
<213> ORGANISM: Artificial Sequence
<220> FEATURE:
<223> OTHER INFORMATION: synthetic construct

<400> SEQUENCE: 162

Met Pro Leu Phe Gly Leu Leu Leu Pro Val Pro Pro Ser Gly Arg Ser
1               5                   10                  15

Leu Ser Leu Met Leu Ala Leu Ile Arg Gly Leu Ser Lys Arg Leu Ala
            20                  25                  30

<210> SEQ ID NO 163
<211> LENGTH: 32
<212> TYPE: PRT
<213> ORGANISM: Artificial Sequence
<220> FEATURE:
<223> OTHER INFORMATION: synthetic construct

<400> SEQUENCE: 163

Met Pro Leu Phe Gly Leu Leu Leu Pro Val Pro Arg Ser Gly Arg Ser
1               5                   10                  15

Leu Ser Leu Met Leu Ala Leu Ile Arg Ala Leu Ser Lys Arg Leu Ala
            20                  25                  30

<210> SEQ ID NO 164
<211> LENGTH: 32
<212> TYPE: PRT
<213> ORGANISM: Artificial Sequence
<220> FEATURE:
<223> OTHER INFORMATION: synthetic construct

<400> SEQUENCE: 164

Met Pro Leu Phe Gly Leu Leu Leu Pro Val Pro Arg Ser Gly Arg Ser
1               5                   10                  15

```
Leu Ser Leu Met Leu Thr Leu Ile Arg Ala Leu Ser Lys Arg Leu Ala
            20                  25                  30

<210> SEQ ID NO 165
<211> LENGTH: 32
<212> TYPE: PRT
<213> ORGANISM: Artificial Sequence
<220> FEATURE:
<223> OTHER INFORMATION: synthetic construct

<400> SEQUENCE: 165

Met Pro Leu Phe Gly Leu Leu Leu Pro Val Pro Arg Ser Gly Arg Ser
1               5                   10                  15

Leu Ser Leu Met Leu Ala Leu Ile Arg Ala Leu Ser Lys Arg Leu Gly
            20                  25                  30

<210> SEQ ID NO 166
<211> LENGTH: 32
<212> TYPE: PRT
<213> ORGANISM: Artificial Sequence
<220> FEATURE:
<223> OTHER INFORMATION: synthetic construct

<400> SEQUENCE: 166

Met Pro Leu Phe Gly Leu Leu Leu Pro Val Pro Arg Ser Gly Arg Ser
1               5                   10                  15

Leu Ser Leu Met Leu Ala Leu Ile Arg Gly Leu Ser Lys Arg Leu Ala
            20                  25                  30

<210> SEQ ID NO 167
<211> LENGTH: 32
<212> TYPE: PRT
<213> ORGANISM: Artificial Sequence
<220> FEATURE:
<223> OTHER INFORMATION: synthetic construct

<400> SEQUENCE: 167

Met Pro Leu Phe Gly Leu Leu Leu Pro Val Arg Arg Ser Gly Arg Ser
1               5                   10                  15

Leu Ser Leu Met Leu Ala Leu Ile Arg Ala Leu Ser Lys Arg Leu Ala
            20                  25                  30

<210> SEQ ID NO 168
<211> LENGTH: 32
<212> TYPE: PRT
<213> ORGANISM: Artificial Sequence
<220> FEATURE:
<223> OTHER INFORMATION: synthetic construct

<400> SEQUENCE: 168

Met Pro Leu Phe Gly Leu Leu Leu Pro Val Arg Arg Ser Gly Arg Ser
1               5                   10                  15

Leu Ser Leu Met Leu Thr Leu Ile Arg Ala Leu Ser Lys Arg Leu Ala
            20                  25                  30

<210> SEQ ID NO 169
<211> LENGTH: 32
<212> TYPE: PRT
<213> ORGANISM: Artificial Sequence
<220> FEATURE:
<223> OTHER INFORMATION: synthetic construct

<400> SEQUENCE: 169

Met Pro Leu Phe Gly Leu Leu Leu Pro Val Arg Arg Ser Gly Arg Ser
```

-continued

```
1               5                    10                  15

Leu Ser Leu Met Leu Ala Leu Ile Arg Ala Leu Ser Lys Arg Leu Gly
            20                  25                  30

<210> SEQ ID NO 170
<211> LENGTH: 32
<212> TYPE: PRT
<213> ORGANISM: Artificial Sequence
<220> FEATURE:
<223> OTHER INFORMATION: synthetic construct

<400> SEQUENCE: 170

Met Pro Leu Phe Gly Leu Leu Leu Pro Val Arg Arg Ser Gly Arg Ser
1               5                    10                  15

Leu Ser Leu Met Leu Ala Leu Ile Arg Gly Leu Ser Lys Arg Leu Ala
            20                  25                  30

<210> SEQ ID NO 171
<211> LENGTH: 32
<212> TYPE: PRT
<213> ORGANISM: Artificial Sequence
<220> FEATURE:
<223> OTHER INFORMATION: synthetic construct

<400> SEQUENCE: 171

Met Pro Leu Phe Gly Leu Leu Leu Pro Val Pro Pro Ser Gly Arg Ser
1               5                    10                  15

Pro Ser Pro Met Pro Thr Pro Ile Pro Gly Pro Ser Lys Pro Pro Gly
            20                  25                  30

<210> SEQ ID NO 172
<211> LENGTH: 32
<212> TYPE: PRT
<213> ORGANISM: Artificial Sequence
<220> FEATURE:
<223> OTHER INFORMATION: synthetic construct

<400> SEQUENCE: 172

Met Pro Leu Phe Gly Leu Leu Leu Pro Val Pro Pro Ser Gly Arg Ser
1               5                    10                  15

Pro Ser Leu Met Pro Thr Pro Ile Pro Gly Pro Ser Lys Pro Pro Gly
            20                  25                  30

<210> SEQ ID NO 173
<211> LENGTH: 32
<212> TYPE: PRT
<213> ORGANISM: Artificial Sequence
<220> FEATURE:
<223> OTHER INFORMATION: synthetic construct

<400> SEQUENCE: 173

Met Pro Leu Phe Gly Leu Leu Leu Pro Val Pro Pro Ser Gly Arg Ser
1               5                    10                  15

Pro Ser Leu Met Pro Thr Leu Ile Pro Gly Pro Ser Lys Pro Pro Gly
            20                  25                  30

<210> SEQ ID NO 174
<211> LENGTH: 32
<212> TYPE: PRT
<213> ORGANISM: Artificial Sequence
<220> FEATURE:
<223> OTHER INFORMATION: synthetic construct

<400> SEQUENCE: 174
```

-continued

```
Met Pro Leu Phe Gly Leu Leu Leu Pro Val Pro Pro Ser Gly Arg Ser
1               5                   10                  15

Pro Ser Leu Met Pro Thr Leu Ile Pro Gly Leu Ser Lys Pro Pro Gly
            20                  25                  30

<210> SEQ ID NO 175
<211> LENGTH: 32
<212> TYPE: PRT
<213> ORGANISM: Artificial Sequence
<220> FEATURE:
<223> OTHER INFORMATION: synthetic construct

<400> SEQUENCE: 175

Met Pro Leu Phe Gly Leu Leu Leu Pro Val Pro Pro Ser Gly Arg Ser
1               5                   10                  15

Pro Ser Leu Met Pro Thr Leu Ile Pro Gly Leu Ser Lys Pro Leu Gly
            20                  25                  30

<210> SEQ ID NO 176
<211> LENGTH: 32
<212> TYPE: PRT
<213> ORGANISM: Artificial Sequence
<220> FEATURE:
<223> OTHER INFORMATION: synthetic construct

<400> SEQUENCE: 176

Met Pro Leu Phe Gly Leu Leu Leu Pro Val Pro Pro Ser Gly Arg Ser
1               5                   10                  15

Leu Ser Leu Met Pro Thr Leu Ile Pro Gly Leu Ser Lys Pro Leu Gly
            20                  25                  30

<210> SEQ ID NO 177
<211> LENGTH: 32
<212> TYPE: PRT
<213> ORGANISM: Artificial Sequence
<220> FEATURE:
<223> OTHER INFORMATION: synthetic construct

<400> SEQUENCE: 177

Met Pro Leu Phe Gly Leu Leu Leu Pro Val Pro Pro Ser Gly Arg Ser
1               5                   10                  15

Leu Ser Leu Met Pro Thr Leu Ile Pro Gly Leu Ser Lys Arg Leu Gly
            20                  25                  30

<210> SEQ ID NO 178
<211> LENGTH: 32
<212> TYPE: PRT
<213> ORGANISM: Artificial Sequence
<220> FEATURE:
<223> OTHER INFORMATION: synthetic construct

<400> SEQUENCE: 178

Met Pro Leu Phe Gly Leu Leu Leu Pro Val Pro Pro Ser Gly Arg Ser
1               5                   10                  15

Leu Ser Leu Met Leu Thr Leu Ile Pro Gly Leu Ser Lys Arg Leu Gly
            20                  25                  30

<210> SEQ ID NO 179
<211> LENGTH: 32
<212> TYPE: PRT
<213> ORGANISM: Artificial Sequence
<220> FEATURE:
<223> OTHER INFORMATION: synthetic construct

<400> SEQUENCE: 179
```

-continued

```
Met Pro Leu Phe Gly Leu Leu Leu Pro Val Pro Arg Ser Gly Arg Ser
1               5                   10                  15

Pro Ser Pro Met Pro Thr Pro Ile Pro Gly Pro Ser Lys Pro Pro Gly
            20                  25                  30
```

<210> SEQ ID NO 180
<211> LENGTH: 32
<212> TYPE: PRT
<213> ORGANISM: Artificial Sequence
<220> FEATURE:
<223> OTHER INFORMATION: synthetic construct

<400> SEQUENCE: 180

```
Met Pro Leu Phe Gly Leu Leu Leu Pro Val Pro Arg Ser Gly Arg Ser
1               5                   10                  15

Pro Ser Leu Met Pro Thr Pro Ile Pro Gly Pro Ser Lys Pro Pro Gly
            20                  25                  30
```

<210> SEQ ID NO 181
<211> LENGTH: 32
<212> TYPE: PRT
<213> ORGANISM: Artificial Sequence
<220> FEATURE:
<223> OTHER INFORMATION: synthetic construct

<400> SEQUENCE: 181

```
Met Pro Leu Phe Gly Leu Leu Leu Pro Val Pro Arg Ser Gly Arg Ser
1               5                   10                  15

Pro Ser Leu Met Pro Thr Leu Ile Pro Gly Pro Ser Lys Pro Pro Gly
            20                  25                  30
```

<210> SEQ ID NO 182
<211> LENGTH: 32
<212> TYPE: PRT
<213> ORGANISM: Artificial Sequence
<220> FEATURE:
<223> OTHER INFORMATION: synthetic construct

<400> SEQUENCE: 182

```
Met Pro Leu Phe Gly Leu Leu Leu Pro Val Pro Arg Ser Gly Arg Ser
1               5                   10                  15

Pro Ser Leu Met Pro Thr Leu Ile Pro Gly Leu Ser Lys Pro Pro Gly
            20                  25                  30
```

<210> SEQ ID NO 183
<211> LENGTH: 32
<212> TYPE: PRT
<213> ORGANISM: Artificial Sequence
<220> FEATURE:
<223> OTHER INFORMATION: synthetic construct

<400> SEQUENCE: 183

```
Met Pro Leu Phe Gly Leu Leu Leu Pro Val Pro Arg Ser Gly Arg Ser
1               5                   10                  15

Pro Ser Leu Met Pro Thr Leu Ile Pro Gly Leu Ser Lys Pro Leu Gly
            20                  25                  30
```

<210> SEQ ID NO 184
<211> LENGTH: 32
<212> TYPE: PRT
<213> ORGANISM: Artificial Sequence
<220> FEATURE:
<223> OTHER INFORMATION: synthetic construct

```
<400> SEQUENCE: 184

Met Pro Leu Phe Gly Leu Leu Leu Pro Val Pro Arg Ser Gly Arg Ser
1               5                   10                  15

Leu Ser Leu Met Pro Thr Leu Ile Pro Gly Leu Ser Lys Pro Leu Gly
            20                  25                  30

<210> SEQ ID NO 185
<211> LENGTH: 32
<212> TYPE: PRT
<213> ORGANISM: Artificial Sequence
<220> FEATURE:
<223> OTHER INFORMATION: synthetic construct

<400> SEQUENCE: 185

Met Pro Leu Phe Gly Leu Leu Leu Pro Val Pro Arg Ser Gly Arg Ser
1               5                   10                  15

Leu Ser Leu Met Pro Thr Leu Ile Pro Gly Leu Ser Lys Arg Leu Gly
            20                  25                  30

<210> SEQ ID NO 186
<211> LENGTH: 32
<212> TYPE: PRT
<213> ORGANISM: Artificial Sequence
<220> FEATURE:
<223> OTHER INFORMATION: synthetic construct

<400> SEQUENCE: 186

Met Pro Leu Phe Gly Leu Leu Leu Pro Val Pro Arg Ser Gly Arg Ser
1               5                   10                  15

Leu Ser Leu Met Leu Thr Leu Ile Pro Gly Leu Ser Lys Arg Leu Gly
            20                  25                  30

<210> SEQ ID NO 187
<211> LENGTH: 32
<212> TYPE: PRT
<213> ORGANISM: Artificial Sequence
<220> FEATURE:
<223> OTHER INFORMATION: synthetic construct

<400> SEQUENCE: 187

Met Pro Leu Phe Gly Leu Leu Leu Pro Val Arg Arg Ser Gly Arg Ser
1               5                   10                  15

Pro Ser Pro Met Pro Thr Pro Ile Pro Gly Pro Ser Lys Pro Pro Gly
            20                  25                  30

<210> SEQ ID NO 188
<211> LENGTH: 32
<212> TYPE: PRT
<213> ORGANISM: Artificial Sequence
<220> FEATURE:
<223> OTHER INFORMATION: synthetic construct

<400> SEQUENCE: 188

Met Pro Leu Phe Gly Leu Leu Leu Pro Val Arg Arg Ser Gly Arg Ser
1               5                   10                  15

Pro Ser Leu Met Pro Thr Pro Ile Pro Gly Pro Ser Lys Pro Pro Gly
            20                  25                  30

<210> SEQ ID NO 189
<211> LENGTH: 32
<212> TYPE: PRT
<213> ORGANISM: Artificial Sequence
<220> FEATURE:
<223> OTHER INFORMATION: synthetic construct
```

```
<400> SEQUENCE: 189

Met Pro Leu Phe Gly Leu Leu Leu Pro Val Arg Arg Ser Gly Arg Ser
1               5                   10                  15

Pro Ser Leu Met Pro Thr Leu Ile Pro Gly Pro Ser Lys Pro Pro Gly
            20                  25                  30

<210> SEQ ID NO 190
<211> LENGTH: 32
<212> TYPE: PRT
<213> ORGANISM: Artificial Sequence
<220> FEATURE:
<223> OTHER INFORMATION: synthetic construct

<400> SEQUENCE: 190

Met Pro Leu Phe Gly Leu Leu Leu Pro Val Arg Arg Ser Gly Arg Ser
1               5                   10                  15

Pro Ser Leu Met Pro Thr Leu Ile Pro Gly Leu Ser Lys Pro Pro Gly
            20                  25                  30

<210> SEQ ID NO 191
<211> LENGTH: 32
<212> TYPE: PRT
<213> ORGANISM: Artificial Sequence
<220> FEATURE:
<223> OTHER INFORMATION: synthetic construct

<400> SEQUENCE: 191

Met Pro Leu Phe Gly Leu Leu Leu Pro Val Arg Arg Ser Gly Arg Ser
1               5                   10                  15

Pro Ser Leu Met Pro Thr Leu Ile Pro Gly Leu Ser Lys Pro Leu Gly
            20                  25                  30

<210> SEQ ID NO 192
<211> LENGTH: 32
<212> TYPE: PRT
<213> ORGANISM: Artificial Sequence
<220> FEATURE:
<223> OTHER INFORMATION: synthetic construct

<400> SEQUENCE: 192

Met Pro Leu Phe Gly Leu Leu Leu Pro Val Arg Arg Ser Gly Arg Ser
1               5                   10                  15

Leu Ser Leu Met Pro Thr Leu Ile Pro Gly Leu Ser Lys Pro Leu Gly
            20                  25                  30

<210> SEQ ID NO 193
<211> LENGTH: 32
<212> TYPE: PRT
<213> ORGANISM: Artificial Sequence
<220> FEATURE:
<223> OTHER INFORMATION: synthetic construct

<400> SEQUENCE: 193

Met Pro Leu Phe Gly Leu Leu Leu Pro Val Arg Arg Ser Gly Arg Ser
1               5                   10                  15

Leu Ser Leu Met Pro Thr Leu Ile Pro Gly Leu Ser Lys Arg Leu Gly
            20                  25                  30

<210> SEQ ID NO 194
<211> LENGTH: 32
<212> TYPE: PRT
<213> ORGANISM: Artificial Sequence
<220> FEATURE:
```

<223> OTHER INFORMATION: synthetic construct

<400> SEQUENCE: 194

Met Pro Leu Phe Gly Leu Leu Leu Pro Val Arg Arg Ser Gly Arg Ser
1               5                   10                  15

Leu Ser Leu Met Leu Thr Leu Ile Pro Gly Leu Ser Lys Arg Leu Gly
            20                  25                  30

<210> SEQ ID NO 195
<211> LENGTH: 32
<212> TYPE: PRT
<213> ORGANISM: Artificial Sequence
<220> FEATURE:
<223> OTHER INFORMATION: synthetic construct

<400> SEQUENCE: 195

Met Arg Leu Ala Ala Leu Leu Leu Ala Ala Arg Arg Ser Gly Arg Ser
1               5                   10                  15

Leu Ser Leu Met Leu Ala Leu Ile Arg Ala Leu Ser Lys Arg Leu Ala
            20                  25                  30

<210> SEQ ID NO 196
<211> LENGTH: 32
<212> TYPE: PRT
<213> ORGANISM: Artificial Sequence
<220> FEATURE:
<223> OTHER INFORMATION: synthetic construct

<400> SEQUENCE: 196

Met Arg Leu Ala Ala Leu Leu Leu Ala Ala Arg Arg Ser Gly Arg Ser
1               5                   10                  15

Leu Ser Leu Met Leu Thr Leu Ile Arg Ala Leu Ser Lys Arg Leu Ala
            20                  25                  30

<210> SEQ ID NO 197
<211> LENGTH: 32
<212> TYPE: PRT
<213> ORGANISM: Artificial Sequence
<220> FEATURE:
<223> OTHER INFORMATION: synthetic construct

<400> SEQUENCE: 197

Met Arg Leu Ala Ala Leu Leu Leu Ala Ala Arg Arg Ser Gly Arg Ser
1               5                   10                  15

Leu Ser Leu Met Leu Ala Leu Ile Arg Ala Leu Ser Lys Arg Leu Gly
            20                  25                  30

<210> SEQ ID NO 198
<211> LENGTH: 32
<212> TYPE: PRT
<213> ORGANISM: Artificial Sequence
<220> FEATURE:
<223> OTHER INFORMATION: synthetic construct

<400> SEQUENCE: 198

Met Arg Leu Ala Ala Leu Leu Leu Ala Ala Arg Arg Ser Gly Arg Ser
1               5                   10                  15

Leu Ser Leu Met Leu Ala Leu Ile Arg Gly Leu Ser Lys Arg Leu Ala
            20                  25                  30

<210> SEQ ID NO 199
<211> LENGTH: 32
<212> TYPE: PRT
<213> ORGANISM: Artificial Sequence -continued

```
<220> FEATURE:
<223> OTHER INFORMATION: synthetic construct

<400> SEQUENCE: 199

Met Arg Leu Phe Ala Leu Leu Leu Ala Ala Arg Arg Ser Gly Arg Ser
1               5                   10                  15

Leu Ser Leu Met Leu Ala Leu Ile Arg Ala Leu Ser Lys Arg Leu Ala
            20                  25                  30

<210> SEQ ID NO 200
<211> LENGTH: 32
<212> TYPE: PRT
<213> ORGANISM: Artificial Sequence
<220> FEATURE:
<223> OTHER INFORMATION: synthetic construct

<400> SEQUENCE: 200

Met Arg Leu Phe Ala Leu Leu Leu Ala Ala Arg Arg Ser Gly Arg Ser
1               5                   10                  15

Leu Ser Leu Met Leu Thr Leu Ile Arg Ala Leu Ser Lys Arg Leu Ala
            20                  25                  30

<210> SEQ ID NO 201
<211> LENGTH: 32
<212> TYPE: PRT
<213> ORGANISM: Artificial Sequence
<220> FEATURE:
<223> OTHER INFORMATION: synthetic construct

<400> SEQUENCE: 201

Met Arg Leu Phe Ala Leu Leu Leu Ala Ala Arg Arg Ser Gly Arg Ser
1               5                   10                  15

Leu Ser Leu Met Leu Ala Leu Ile Arg Ala Leu Ser Lys Arg Leu Gly
            20                  25                  30

<210> SEQ ID NO 202
<211> LENGTH: 32
<212> TYPE: PRT
<213> ORGANISM: Artificial Sequence
<220> FEATURE:
<223> OTHER INFORMATION: synthetic construct

<400> SEQUENCE: 202

Met Arg Leu Phe Ala Leu Leu Leu Ala Ala Arg Arg Ser Gly Arg Ser
1               5                   10                  15

Leu Ser Leu Met Leu Ala Leu Ile Arg Gly Leu Ser Lys Arg Leu Ala
            20                  25                  30

<210> SEQ ID NO 203
<211> LENGTH: 32
<212> TYPE: PRT
<213> ORGANISM: Artificial Sequence
<220> FEATURE:
<223> OTHER INFORMATION: synthetic construct

<400> SEQUENCE: 203

Met Arg Leu Ala Gly Leu Leu Leu Ala Ala Arg Arg Ser Gly Arg Ser
1               5                   10                  15

Leu Ser Leu Met Leu Ala Leu Ile Arg Ala Leu Ser Lys Arg Leu Ala
            20                  25                  30

<210> SEQ ID NO 204
<211> LENGTH: 32
<212> TYPE: PRT
```

-continued

<213> ORGANISM: Artificial Sequence
<220> FEATURE:
<223> OTHER INFORMATION: synthetic construct

<400> SEQUENCE: 204

Met Arg Leu Ala Gly Leu Leu Leu Ala Ala Arg Arg Ser Gly Arg Ser
1               5                   10                  15

Leu Ser Leu Met Leu Thr Leu Ile Arg Ala Leu Ser Lys Arg Leu Ala
            20                  25                  30

<210> SEQ ID NO 205
<211> LENGTH: 32
<212> TYPE: PRT
<213> ORGANISM: Artificial Sequence
<220> FEATURE:
<223> OTHER INFORMATION: synthetic construct

<400> SEQUENCE: 205

Met Arg Leu Ala Gly Leu Leu Leu Ala Ala Arg Arg Ser Gly Arg Ser
1               5                   10                  15

Leu Ser Leu Met Leu Ala Leu Ile Arg Ala Leu Ser Lys Arg Leu Gly
            20                  25                  30

<210> SEQ ID NO 206
<211> LENGTH: 32
<212> TYPE: PRT
<213> ORGANISM: Artificial Sequence
<220> FEATURE:
<223> OTHER INFORMATION: synthetic construct

<400> SEQUENCE: 206

Met Arg Leu Ala Gly Leu Leu Leu Ala Ala Arg Arg Ser Gly Arg Ser
1               5                   10                  15

Leu Ser Leu Met Leu Ala Leu Ile Arg Gly Leu Ser Lys Arg Leu Ala
            20                  25                  30

<210> SEQ ID NO 207
<211> LENGTH: 32
<212> TYPE: PRT
<213> ORGANISM: Artificial Sequence
<220> FEATURE:
<223> OTHER INFORMATION: synthetic construct

<400> SEQUENCE: 207

Met Arg Leu Ala Ala Leu Leu Leu Ala Val Arg Arg Ser Gly Arg Ser
1               5                   10                  15

Leu Ser Leu Met Leu Ala Leu Ile Arg Ala Leu Ser Lys Arg Leu Ala
            20                  25                  30

<210> SEQ ID NO 208
<211> LENGTH: 32
<212> TYPE: PRT
<213> ORGANISM: Artificial Sequence
<220> FEATURE:
<223> OTHER INFORMATION: synthetic construct

<400> SEQUENCE: 208

Met Arg Leu Ala Ala Leu Leu Leu Ala Val Arg Arg Ser Gly Arg Ser
1               5                   10                  15

Leu Ser Leu Met Leu Thr Leu Ile Arg Ala Leu Ser Lys Arg Leu Ala
            20                  25                  30

<210> SEQ ID NO 209
<211> LENGTH: 32

```
<212> TYPE: PRT
<213> ORGANISM: Artificial Sequence
<220> FEATURE:
<223> OTHER INFORMATION: synthetic construct

<400> SEQUENCE: 209

Met Arg Leu Ala Ala Leu Leu Leu Ala Val Arg Arg Ser Gly Arg Ser
1               5                   10                  15

Leu Ser Leu Met Leu Ala Leu Ile Arg Ala Leu Ser Lys Arg Leu Gly
            20                  25                  30

<210> SEQ ID NO 210
<211> LENGTH: 32
<212> TYPE: PRT
<213> ORGANISM: Artificial Sequence
<220> FEATURE:
<223> OTHER INFORMATION: synthetic construct

<400> SEQUENCE: 210

Met Arg Leu Ala Ala Leu Leu Leu Ala Val Arg Arg Ser Gly Arg Ser
1               5                   10                  15

Leu Ser Leu Met Leu Ala Leu Ile Arg Gly Leu Ser Lys Arg Leu Ala
            20                  25                  30

<210> SEQ ID NO 211
<211> LENGTH: 32
<212> TYPE: PRT
<213> ORGANISM: Artificial Sequence
<220> FEATURE:
<223> OTHER INFORMATION: synthetic construct

<400> SEQUENCE: 211

Met Arg Leu Phe Gly Leu Leu Leu Ala Val Arg Arg Ser Gly Arg Ser
1               5                   10                  15

Leu Ser Leu Met Leu Asp Leu Ile Arg Gly Leu Ser Lys Arg Leu Gly
            20                  25                  30

<210> SEQ ID NO 212
<211> LENGTH: 32
<212> TYPE: PRT
<213> ORGANISM: Artificial Sequence
<220> FEATURE:
<223> OTHER INFORMATION: synthetic construct

<400> SEQUENCE: 212

Met Arg Leu Phe Gly Leu Leu Leu Ala Val Arg Arg Ser Gly Arg Ser
1               5                   10                  15

Leu Ser Leu Met Leu Arg Leu Ile Arg Gly Leu Ser Lys Arg Leu Gly
            20                  25                  30

<210> SEQ ID NO 213
<211> LENGTH: 32
<212> TYPE: PRT
<213> ORGANISM: Artificial Sequence
<220> FEATURE:
<223> OTHER INFORMATION: synthetic construct

<400> SEQUENCE: 213

Met Arg Leu Phe Gly Leu Leu Leu Ala Val Arg Arg Ser Gly Arg Ser
1               5                   10                  15

Leu Ser Leu Met Leu Trp Leu Ile Arg Gly Leu Ser Lys Arg Leu Gly
            20                  25                  30

<210> SEQ ID NO 214
```

-continued

```
<211> LENGTH: 32
<212> TYPE: PRT
<213> ORGANISM: Artificial Sequence
<220> FEATURE:
<223> OTHER INFORMATION: synthetic construct

<400> SEQUENCE: 214

Met Arg Leu Phe Gly Leu Leu Leu Ala Val Arg Arg Ser Gly Arg Ser
1               5                   10                  15

Leu Ser Leu Met Leu Lys Leu Ile Arg Gly Leu Ser Lys Arg Leu Gly
            20                  25                  30

<210> SEQ ID NO 215
<211> LENGTH: 32
<212> TYPE: PRT
<213> ORGANISM: Homo sapiens

<400> SEQUENCE: 215

Met Arg Leu Phe Gly Leu Leu Leu Ala Val Arg Arg Ser Gly Arg Ser
1               5                   10                  15

Leu Ser Leu Met Leu Thr Leu Ile Arg Gly Leu Ser Lys Arg Leu Gly
            20                  25                  30
```